(12) United States Patent
Foster

(10) Patent No.: US 11,732,270 B2
(45) Date of Patent: Aug. 22, 2023

(54) COMPOSITIONS AND METHODS FOR MANIPULATING THE DEVELOPMENT OF PLANTS

(71) Applicant: The New Zealand Institute for Plant and Food Research Limited, Auckland (NZ)

(72) Inventor: Toshi Marie Foster, Ashhurst (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 145 days.

(21) Appl. No.: 17/124,378

(22) Filed: Dec. 16, 2020

(65) Prior Publication Data

US 2021/0102217 A1    Apr. 8, 2021

Related U.S. Application Data

(63) Continuation of application No. 16/062,597, filed as application No. PCT/IB2016/057631 on Dec. 14, 2016, now abandoned.

(30) Foreign Application Priority Data

Dec. 16, 2015   (NZ) .................................. 714988

(51) Int. Cl.
| | | |
|---|---|---|
| C12N 15/82 | (2006.01) | |
| C12N 15/67 | (2006.01) | |
| C12Q 1/68 | (2018.01) | |
| C07K 14/415 | (2006.01) | |
| A01H 6/74 | (2018.01) | |
| C12Q 1/6895 | (2018.01) | |

(52) U.S. Cl.
CPC ....... *C12N 15/8241* (2013.01); *A01H 6/7418* (2018.05); *C07K 14/415* (2013.01); *C12N 15/67* (2013.01); *C12N 15/827* (2013.01); *C12N 15/8223* (2013.01); *C12N 15/8261* (2013.01); *C12N 15/8294* (2013.01); *C12Q 1/68* (2013.01); *C12Q 1/6895* (2013.01); *Y02A 40/146* (2018.01)

(58) Field of Classification Search
None
See application file for complete search history.

(56) References Cited

U.S. PATENT DOCUMENTS

| | | |
|---|---|---|
| 4,795,855 A | 1/1989 | Fillatti et al. |
| 4,943,674 A | 7/1990 | Houck et al. |
| 5,004,863 A | 4/1991 | Umbeck |
| 5,086,169 A | 2/1992 | Mascarenhas |
| 5,159,135 A | 10/1992 | Umbeck |
| 5,177,010 A | 1/1993 | Goldman et al. |
| 5,187,073 A | 2/1993 | Goldman et al. |
| 5,188,958 A | 2/1993 | Moloney et al. |
| 5,412,085 A | 5/1995 | Allen et al. |
| 5,416,011 A | 5/1995 | Hinchee et al. |
| 5,463,174 A | 10/1995 | Moloney et al. |
| 5,536,653 A | 7/1996 | Barry et al. |
| 5,545,546 A | 8/1996 | Allen et al. |
| 5,563,055 A | 10/1996 | Townsend et al. |
| 5,569,834 A | 10/1996 | Hinchee et al. |
| 5,591,616 A | 1/1997 | Hiei et al. |
| 5,608,150 A | 3/1997 | Conner |
| 5,639,952 A | 6/1997 | Quail et al. |
| 5,656,496 A | 8/1997 | Quail et al. |
| 5,750,385 A | 5/1998 | Shewmaker et al. |
| 5,750,871 A | 5/1998 | Moloney et al. |
| 5,792,935 A | 8/1998 | Arntzen et al. |
| 5,824,877 A | 10/1998 | Hinchee et al. |
| 5,837,848 A | 11/1998 | Ely et al. |
| 5,846,797 A | 12/1998 | Strickland |
| 5,952,543 A | 9/1999 | Firoozabady et al. |
| 5,968,830 A | 10/1999 | Dan et al. |
| 5,981,840 A | 11/1999 | Zhao et al. |
| 6,020,539 A | 2/2000 | Goldman et al. |
| 6,037,522 A | 3/2000 | Dong et al. |
| 6,074,877 A | 6/2000 | D'Halluin et al. |
| 6,127,179 A | 10/2000 | Dellapenna et al. |
| 6,184,443 B1 | 2/2001 | Pedersen et al. |

(Continued)

FOREIGN PATENT DOCUMENTS

| | | |
|---|---|---|
| CN | 104178495 A | 12/2014 |
| WO | WO 2002/000894 A2 | 1/2002 |

(Continued)

OTHER PUBLICATIONS

Farrell. The Regulation of Gene Expression in Plants and Animals. Chapter 1 pp. 1-38 In Regulation of Gene Expression in Plants, Edited by Carole L. Bassett., 2007, Springer. (Year: 2007).*

(Continued)

*Primary Examiner* — Cynthia E Collins
(74) *Attorney, Agent, or Firm* — Leydig, Voit & Mayer, Ltd.

(57) ABSTRACT

The invention provides a methods and materials for producing and selecting plants with at least one dwarfing-associated phenotype. The methods and materials relate to altering the expression, or activity, of an ARF3 polypeptide in the plant, and selecting plants with altered the expression, or activity, of an ARF3 polypeptide. The invention also provides plants produced or selected by the methods. The methods also involve crossing plants of the invention with other plants to produce further plants with at least one dwarfing-associated phenotype.

10 Claims, 28 Drawing Sheets

Specification includes a Sequence Listing.

(56) References Cited

U.S. PATENT DOCUMENTS

| | | | |
|---|---|---|---|
| 6,228,643 | B1 | 5/2001 | Greenland et al. |
| 6,229,067 | B1 | 5/2001 | Sonnewald et al. |
| 6,342,657 | B1 | 1/2002 | Thomas et al. |
| 7,081,565 | B2 | 7/2006 | Ohlrogge et al. |
| 7,141,424 | B2 | 11/2006 | Shin et al. |
| 7,153,953 | B2 | 12/2006 | Marraccini et al. |
| 7,371,928 | B2 | 5/2008 | Suh et al. |
| 7,405,345 | B2 | 7/2008 | Ohlrogge et al. |
| 7,629,454 | B2 | 12/2009 | Chan et al. |
| 7,642,346 | B2 | 1/2010 | Chaudhary et al. |
| 7,667,097 | B2 | 2/2010 | Scheirlinck et al. |
| 7,745,697 | B2 | 6/2010 | Perez et al. |
| 2001/0047525 | A1 | 11/2001 | Bruce et al. |
| 2004/0067506 | A1 | 4/2004 | Scheres et al. |
| 2010/0240061 | A1 | 9/2010 | Butruille et al. |
| 2015/0007360 | A1* | 1/2015 | Paul .................. A01H 6/46 800/290 |
| 2015/0143581 | A1 | 5/2015 | Liu et al. |
| 2018/0371481 | A1 | 12/2018 | Foster |

FOREIGN PATENT DOCUMENTS

| | | |
|---|---|---|
| WO | WO 2011/053169 A1 | 5/2011 |
| WO | WO 2013/034722 A1 | 3/2013 |

OTHER PUBLICATIONS

Fahlgren et al. Regulation of Auxin Response Factors by TAS3 ta-siRNA Affects Developmental Timing and Patterning in *Arabidopsis*. Curr. Biol. May 9, 2006;16(9):939-44. (Year: 2006).*

Alam et al., "Transgenic insect-resistant maintainer line (IR68899B) for improvement of hybrid rice," Plant Cell Rep., 18:572-575 (1999).

Allan et al. "Malus x domestica ARF domain class transcription factor (ARF3) mRNA," XP-002790323, NCBI Database Accession No. HM122438 (2010) 2 pages.

Altpeter et al., "Comparison of Transgene Expression Stability after Agrobacterium-mediated or Biolistic Gene Transfer into Perennial Ryegrass," Developments in Plant Breeding, 11(7):255-260 (2004).

Altschul et al. "Gapped BLAST and PSI-BLAST: a new generation of protein database search programs," Nucleic Acids Res., 25(17):3389-3402 (1997).

Aronesty, "ea-utils: Command-line tools for processing biological sequencing data," Durham, NC: Expression Analysis (2011).

Bairoch et al., "PROSITE: recent developments," Nucleic Acids Res., 22(17):3583-3589 (1994).

Bennett et al., "The *Arabidopsis* MAX Pathway Controls Shoot Branching by Regulating Auxin Transport," Current Biology, 16(6):553-563 (2006).

Birch, "Plant Transfomation: Problems and Strategies for Practical Application," Ann. Rev. Plant Phys. Plant Mol. Biol., 48:297-326 (1997).

Böhlenius et al., "CO/FT Regulatory Module Controls Timing of Flowering and Seasonal Growth Cessation in Trees," Science, 312(5776): 1040-1043 (2006).

Bolton et al., "A General Method for the Isolation of RNA Complementary to DNA", PNAS, 48(8):1390-1397 (1962).

Bortesi et al. "The CRISPR/CAS9 system for plant genome editing and beyond," Biotechnology Advances, 33:41-52 (2015).

Bowie et al., "Deciphering the Message in Protein Sequences: Tolerance to Amino Acid Substitutions," Science, 247(4948) 1306-1310 (1990).

Cardoza et al., "Canola (*Brassica napus* L.)," Agrobacterium Protocols 2nd Ed., 343(1):257-266 (2006).

Carrière et al., "Un nouveau sujet pour greffer les pommes," Revue Horticole, pp. 436-437 (1897). (French language).

Celton et al. "Construction of a dense genetic linkage map for apple rootstocks using SSRs developed from Malus ESTs and Pyrus genomic sequences," Tree Genetics & Genomes, 5(1): 93-107 (2009).

Celton et al. "Construction of a 1-15 Dense Genetic Linkage Map for Apple Rootstocks Using SSRs Developed from Malus ESTs and Pyrus Genomic Sequences," Tree Genetics & Genomes (2009) 5(1):93-107.

Cermak et al., "Efficient design and assembly of custom TALEN and other TAL effector-based constructs for DNA targeting," Nucleic Acids Res., 39(12):e82, pp. 1-11 (2011).

Chagné et al., "Development of a set of SNP markers present in expressed genes of the apple," Genomics, 92(5): 353-358 (2008).

Chinese First Search dated Mar. 17, 2021 in corresponding application No. CN 201680080119.

Chinese First Office Acted dated Mar. 30, 2021 in corresponding application No. CN 201680080119.

Christou et al., "Production of transgenic rice (*Oryza sativa* L.) Plants from Agronomically Important Indica and Japonica Varieties via Electric Discharge Particle Acceleration of Exogenous DNA into Immature Zygotic Embryos," Nature Biotech.,9:957-962 (1991).

Collard et al., "Marker-assisted selection: an approach for precision plant breeding in the twenty-first century," Philosophical Transactions of the Royal Society B-Biological Sciences, 363(1491): 557-572. (2008).

Costes et al., "Modelling Branching Patterns on 1-year-old Trunks of Six Apple Cultivars," Annals of Botany, 89(5): 513-524 (2002).

Costes et al., "Modelling the Sylleptic Branching of One-year-old Trunks of Apple Cultivars," J. of American Society for Horticultural Science, 122(1):53-62 (1997).

Crasweller, "Grafting and propagating fruit trees," Pennsylvania State University (2005).

Curtin et al., "Targeted Mutagenesis of Duplicated Genes in Soybean with Zinc-Finger Nucleases," Plant Physiol., 156(2):466-473 (2011).

Dan et al., "MicroTom—a high-throughput model transformation system for functional genomics," Plant Cell Reports, 25:432-441 (2006).

Ellerstrom et al., "Functional dissection of napin gene promoter: identification of promoter elements required for embryo and endosperm-specific transcription," Plant Molecular Biology, 32(6)1019-1027 (1996).

Espley et al., "Red colouration in apple fruit is due to the activity of the MYB transcription factor, MdMYB10", The Plant Journal, 49:414-427 (2007).

European Extended Search Report, dated Apr. 24, 2019, corresponding to European Application No. 16875016.4, parent of the present application, 11 pp.

Fahlgren et al. "Regulation of Auxin Response FACTOR3 by TAS3 ta-siRNA Affects Developmental Timing and Patterning in *Arabidopsis*," Current Biology, 16(9): 939-944 (2006).

Falquet et al., "The PROSITE database, its status in 2002," Nucleic Acids Res., 30(1): 235-238 (2002).

Farrell (2007) "The Regulation of Gene Expression in Plants and Animals," Chapter 1 pp. 1-38 in Regulation of Gene Expression in Plants, Edited by Carole L. Bassett., 2007, Springer.

Fazio et al. (2014). "Dw2, a New Dwarfing Locus in Apple Rootstocks and is Relationship to Induction of Early Bearing in Apple Scions," J. of the Amer. Soc. for Horticultural Sci., 139(2): 87-98.

Feng et al., "Progressive Sequence alignment as a Prerequisite to Correct Phylogenetic trees", J. Mol. Evol., 25(4):351-360 (1985).

Folta et al., "Characterization of LF9, an octoploid strawberry genotype selected for rapid regeneration and transformation", Planta, 224(5): 1058-1067 (2006).

Foster et al., "Two quantitative trait loci, Dw1 and Dw2, are primarily responsible for rootstock-induced dwarfing in apple", Hotric. Res., 2:15001 (2015).

Frohman, "Rapid Amplification of Complementary DNA Ends for Generation of Full-Length Complementary DNAs: Thermal RACE," Methods Enzymol., 218:340-356 (1993).

Fulford, "The Morphogenesis of Apple Buds: II. The Development of the Bud," Annals of Botany, 30(117): 25-38 (1966).

Gardiner et al. "A detailed linkage map around an apple scab resistance gene demonstrates that two disease resistance classes both carry the Vf gene," Theor. and Appl. Genetics, 93(4): 485-493 (1996).

(56) References Cited

OTHER PUBLICATIONS

Giesen et al., "A formula for thermal stability (Tm) prediction of PnA/DNA duplexes," Nucleic Acids Res., 26(21): 5004-5006 (1998).
Graham et al., "Agrobacterium-Medicated Transformation of Soft Fruit Rubus, Ribes, and Fragaria," Methods Mol. Biol., 44:129-33 (1995).
Gregory et al., "Feeding nine billion: the challenge to sustainable crop production," J. of Experimental Botany, 62(15): 5233-5239 (2011).
Guilfoyle et al. (2007) "Auxin response factors," Curr Opin Plant Biol. 10(5):453-60. Epub Sep. 27, 2007. Review.
Han et al. "Strategies for Map-Based Cloning in Apple," Critical Reviews in Plant Sciences (2010) 29(5):265-284.
Hatton, "'Paradise' apple socks," J. of the Royal Horticultural Society, 42: 361-399 (1917).
Hayden et al., "Multiplex-Ready PCR: A new method for multiplexed SSR and SNP genotyping," BMC Genomics, 9(1): 80 (2008).
Hellens et al., "PGreen: A versatile and flexible binary Ti vector for Agrobacterium-mediated plant transformation," Plant Mol. Biol., 42:819-832 (2000).
Herrera-Estrella et al., "Expression of chimaeric genes transferred into plant cells using a Ti-plasmid-derived vector," Nature 303:213 209 (1993).
Hirst et al., "Rootstock Effects on the Flowering of 'Delicious' Apple. I. Bud Development," J. of the Amer. Soc. for Horticultural Sci., 120(6): 1010-1017 (1995).
Hofmann et al., "The PROSITE database, its status in 1999," Nucleic Acids Res., 27(1):215-219(1999).
Hooijdonk et al., "Initial alteration of scion architecture by dwarfing apple rootstocks may involve shoot-root-shoot signalling by auxin, gibberellin, and cytokinin," J. of Horticultural Science & Biotechnology, 85(1): 59-65 (2010).
Hooijdonk et al., "Rootstocks Modify Scion Architecture, Endogenous Hormones, and Root Growth of Newly Grafted 'Royal Gala' Apple Trees," J. of the Amer. Soc. for Horticultural Sci., 136(2): 93-102 (2011).
Horsch et al., "A Simple and General-Method for Transferring Genes Into Plants," Science, 227(4691): 1229-1231 (1985).
Hsu et al., "Flowering Locus T duplication coordinates reproductive and vegetative growth in perennial poplar," PNAS, 108(26): 10756-10761 (2011).
Hsu et al., "Poplar FT2 Shortens the Juvenile Phase and Promotes Seasonal Flowering," The Plant Cell, 18(8): 1846-1861 (2006).
Huang, "On global sequence alignment," Computer Applications in the Biosciences, 10(3):227-235 (1994).
Huijser et al., "The control of developmental phase transitions in plants," Development, 138(19): 4117-4129 (2011).
Hunter et al., "Trans-acting siRNA-mediated repression of ETTIN and ARF4 regulates heteroblasty in *Arabidopsis*," Development, 133(15): 2973-2981 (2006).
Imamura et al., "The Gentian Orthologs of the FT/TFL1 Gene Family Control Floral Initiation in Gentiana," Plant and Cell Physiology, 52(6): 1031-1041 (2011).
International Search Report & Written Opinion, dated Feb. 15, 2017, corresponding to International Application No. PCT/IB2016/057631, parent of the present application, 15 pp.
International Preliminary Report on Patentability, dated Apr. 5, 2018, corresponding to International Application No. PCT/IB2016/057631, parent of the present application, 6 pp.
Izhakia et al., "KANADI and Class III HD-Zip Gene Families Regulate Embryo Patterning and Modulate Auxin Flow during Embryogenesis in 45 *Arabidopsis*," The Plant Cell, 19: 495-508 (2007).
Jang et al., "Functional Classification, Genomic Organization, Putatively cis-Acting Regulatory Elements, and Relationship to Quantitative Trait Loci, of Sorghum Genes with Rhizome-Enriched Expression," Plant Physiol., 142:1148-1159 (2006).
Janssen et al., "Global gene expression analysis of apple fruit development from the floral bud to ripe fruit," BMC Plant Biol., 17;8:16 (2008).
Jeanmougin et al., "Multiple sequence alignment with Clustal X," Trends Biochem. Sci., 23:403-405 (1998).
Josefsson et al., "Structure of Gene Encoding the 1.7 S Storage Protein, Napin, from *Brassica napus*," J. Biol. Chem., 262(25):12196-12201 (1987).
Kelley et al., "ETTIN (ARF3) physically interacts with KANADI proteins to form a functional complex essential for integument development and polarity determination in *Arabidopsis*," Development, 139(6): 1105-1109 (2012).
Kotoda et al., "MdTFL1, a TFL1-like gene of apple, retards the transition from the vegetative to reproductive phase in transgenic *Arabidopsis*," Plant Science, 168(1): 95-104 (2005).
Krens et al., "Transgenic caraway, *Carum carvi* L.: a model species from metabolic engineering," Plant Cell Rep., 17:39-43 (1997).
Kumar et al., "Potato plants expressing antisense and sense S-adenosylmethionine decarboxylase (SAMDC) transgenes show altered levels of polyamines and ethylene: antisense plants display abnormal phenotypes," Plant J. 9(2): 147-158 (1996).
Langmead et al., "Fast gapped-read alignment with Bowtie 2," Nat. Methods, 9(4): 357-359. (2012).
Li et al., "Genetic transformation of cassava (*Manihot esculenta* Crantz)," Nat. Biotechnology, 14:736-740 (1996).
Li et al., "High-efficiency TALEN-based gene editing produces disease-resistant rice," Nat. Biotechnol., 30:390-392 (2012).
Li et al., "The Sequence Alignment/Map format and SAMtools", Bioinformatics, 25(16): 2078-2079 (2009).
Li et al., "Transgenic rose lines harboring an antimicrobial protein gene, Ace-AMP1, demonstrate enhanced resistance to powdery mildew (*Sphaerotheca pannosa*)," Planta, 218:226-232 (2003).
Liebhard et al., "Development and characterisation of 140 new microsatellites in apple (*Malus x domestica* Borkh.)," Molecular Breeding, 10(4): 217-241 (2002).
Liu et al., "Auxin Response FACTOR3 integrates the functions of AGAMOUS and APETALA2 in floral meristem determinacy," Plant Journal, 80(4): 629-641 (2014).
Liung et al. "Sites and Regulation of Auxin Biosynthesis in *Arabidopsis* Roots," The Plant Cell, 17(4): 1090-1104 (2005).
Luo et al., "Genomewide identification and expression analysis of the ARF gene family in apple," J. of Genetics, 93(3):785-797 (2014).
Mahfouz et al., "De novo-engineered transcription activator-like effector (TALE) hybrid nuclease with novel DNA binding specificity creates double-strand breaks," PNAS, 108(6):2623-2628 (2011).
Martin et al., "Transient expression in *Nicotiana benthamiana* fluorescent marker lines provides enhanced definition of protein localization, movement and interactions in planta," Plant J., 59(1): 150-162 (2009).
Matsuda et al., "Development of an Agrobacterium-mediated transformation method for pear (*Pyrus communis* L.) with leaf-section and axillary shootmeristem explants," Plant Cell Rep., 24(1):45-51 (2005).
Michelmore et al., "Transformation of lettuce (*Lactuca sativa*) mediated by Agrobacterium tumefaciens," Plant Cell Rep., 6:439-442 (1987).
Napoli et al. "Reevaluating Concepts of Apical Dominance and the Control of Axillary Bud Outgrowth," Current Topics in Dev. Biol., 44: 127-169 (1998).
Needleman et al., "A General Method Applicable to the Search for Similarities in the Amino Acid Sequence of Two Proteins," J. Mol. Biol., 48:443-453 (1970).
Newcomb et al. "Analyses of Expressed Sequence Tags from Apple," Plant Physiology, 141(1): 147-166 (2006).
Nielsen et al., "Sequence-Selective Recognition of DNA by Strand Displacement with a Thymine-Substituted Polyamide," Science, 254(5037):1497-1500 (1991).
Niu et al., "Transgenic peppermint (*Mentha x piperita* L.) plants obtained by cocultivation with Agrobacterium tumefaciens," Plant Cell Rep., 17:165-171 (1998).
Notredame et al., "T-Coffee: A Novel Method for Fast and Accurate Multiple Sequence Alignment," J. Mol. Biol., 302: 205-217 (2000).

(56) References Cited

OTHER PUBLICATIONS

Oosumi et al., "High-efficiency transformation of the diploid strawberry (*Fragaria vesca*) for functional genomics," Planta, 223(6):1219-1230 (2006).
Orlikowska et al., "Factors influencing Agrobacterium tumefaciens-mediated transformation and regeneration of the safflower cultivar 'centennial'," Plant cell Tissue and Organ Culture, 40:85-91 (1995).
Ortiz et al., "Hygromycin resistance as an efficient selectable marker for wheat stable transformation," Plant Cell Rep., 15:877-881 (1996).
Otto et al. "The Columnar Mutation ("Co Gene") of Apple (*Malus x domestica*) is Associated with an Integration of a Gypsy-Like Retrotransposon," Molecular Breeding (2014) 33(4):863-880.
Padilla et al., "Early antibiotic selection and efficient rooting and acclimatization improve the production of transgenic plum plants (*Prunus domestica* L.)," Plant Cell Rep., 22(1):38-45 (2003).
Pekker et al., "Auxin Response Factors Mediate *Arabidopsis* Organ Asymmetry via Modulation of KANADI Activity," The Plant Cell, 17(11):2899-2910 (2005).
Pena et al., "High efficiency Agrobacterium-mediated transformation and regeneration of citrus," Plant Sci., 104:183-191 (1995).
Pilcher et al., "Genetic Markers Linked to the Dwarfing Trait of Apple Rootstock 'Malling 9'," J. of Amer. Soc. for Horticultural Sci., 133(1): 100-106 (2008).
Potrykus et al., "Gene Transfer to Plants," Springer-Verlag, Berlin. p. 51 (1995).
Quinlan et al., "BEDtools: a flexible suite of utilities for comparing genomic features," Bioinformatics, 26(6): 841-842 (2010).
Ramesh et al., "Improved methods in Agrobacterium-mediated transformation of almond using positive (mannose/pmi) or negative (kanamycin resistance) Selection-based protocols," Plant Cell Rep., 25(8):821-8 (2006).
Rice et al., "EMBOSS: The European Molecular Biology Open Software Suite," Trends in Genetics, 16(6):276-277 (2000).
Sander, et al., "Selection-Free Zinc-Finger Nuclease Engineering by Context-Dependent Assembly (CoDA)," Nat. Methods, 8(1): 67-69 (2011).
Schenk et al., "Promoter for pregenomic RNA of banana streak badnavirus are active for transgene expression in monocot and dicot plants," Plant Molecular Biology, 47:399-412 (2001).
Schuelke, "An economic method for the fluorescent labeling of PCR fragments," Nature Biotechnology, 18(2):233-234 (2000).
Seleznyova et al., "Apple Dwarfing Rootstocks and Interstocks Affect the Type of Growth Units Produced During the Annual Growth Cycle: Precocious Transition to Flowering Affects the Composition and Vigour of Annual Shoots," Annals of Botany, 101(5): 679-687 (2008).
Seleznyova et al., "Application of Architectural Analysis and AMAPmod Methodology to Study Dwarfing Phenomenon: The Branch Structure of 'Royal Gala' Apple Grafted on Dwarfing and Non-Dwarfing Rootstock/Interstock Combinations," Annals of Botany, 91: 665-672 (2003).
Sessions et al., "*Arabidopsis gynoecium* structure in the wild and in ettin mutants," Development, 121(5): 1519-1532 (1995).
Sessions et al., "ETTIN patterns the *Arabidopsis* floral meristem and reproductive organs," Development, 124(22): 4481-4491 (1997).
Shimizu-Sato et al., "Control of Outgrowth and Dormancy in Axillary Buds," Plant Physiology, 127(4): 1405-1413 (2001).
Silfverberg-Dilworth et al., "Microsatellite Markers Spanning the Apple (*Malus x domestica* Borkh.) Genome," Tree Genetics & Genomes, 2(4): 202-224 (2006).
Smeets et al., "Developmental Regulation of Lectin and Allinase Synthesis in Garlic Bulbs and Leaves," Plant Physiol., 113:765-771 (1997).
Smyth, "Limma: Linear Models for Microarray Data", Bioinformatics and Computing Biology Solutions, pp. 397-420 (2005).

Song et al., "Transformation of Montmorency sour cherry (*Prunus cerasus* L.) and Gisela 6 (*P. cerasus* x *P. canescens*) cherry rootstock mediated by Agrobacterium tumefaciens," Plant Cell Rep., 25(2):117-123 (2006).
Soumelidou et al., "Auxin transport capacity in relation to the dwarfing effect of apple rootstocks," J. of Horticultural Science, 69(4): 719-725 (1994).
Stoltz et al., "Reproducing Fruit Trees by Grafting: Budding and Grafting," Univ. of Kentucky, (1982).
Sussex et al., "The evolution of plant architecture." Current Opinion in Plant Biology, 4(1): 33-37 (2001).
Tatusova et al., "Blast 2 Sequences—a new tool for comparing protein and nucleotide sequences," FEMS Microbiol Lett., 174: 247-250 (1999).
Thompson et al., "CLUSTALW: improving the sensitivity of progressive multiple sequence alignment through sequence weighting, positions-specific gap penalties and weight matrix choice," Nucleic Acids Research, 22(22): 4673-4680 (1994).
Trapnell et al., "Transcript assembly and quantification by RNA sequence reveals thousands of new transcripts and switching among isoforms", Nat. Biotechnol., 28(5): 511-515 (2010).
Triglia et al., "A Procedure for in vitro amplification of DNA segments that lie outside the boundaries of known sequences," Nucleic Acids Res., 16(16): 8186 (1988).
Tzfira et al., "Genome modification in plant cells by custom-made restriction enzymes," Plant Biotechnol. J., 10:373-389 (2012).
Ulmasov et al., "Aux/IAA Proteins Repress Expression of Reporter Genes Containing Natural and Highly Active Synthetic Auxin Response Elements," The Plant Cell, 9(11): 1963-1971 (1997).
Velasco et al. "The genome of the domesticated apple (*Malus x domestica* Borkh.)," Nat. Genet., 42(100): 833-839 (2010).
Wang et al., "Handbook of Maize," pp. 609-639 (2009).
Wang et al., "Transformation of Actindia eriantha: A potential species for functional genomics studies in Actinidia," Plant Cell Rep., 25(5): 425-431 (2006).
Webster et al., "Apple Rootstocks," Apples: Botany, Production and Uses. D. C. Ferree and I. J. Warrington. Wallingford, UK, CABI Publishing, CAB International. (2003).
Webster, "Rootstock and interstock effects on deciduous fruit tree vigour, precocity and yield productivity," New Zealand J. of Crop and Horticultural Sci., 23(4): 373-382 (1995).
Willmann, "The effect of the floral repressor FLC on the timing and progression of vegetative phase change in *Arabidopsis*." Development, 138(4): 677-685 (2011).
Yao et al., "Regeneration of transgenic plants from the commercial apple cultivar Royal gala," Plant Cell Rep., 14: 407-412 (1995).
Daccord et al., (2017) "High-quality de novo assembly of the apple genome and methylome dynamics of early fruit development" Nature Genetics 49(7), 1099-1108.
Database EMBL [online] Aug. 16, 2010 (Aug. 16, 2010), "Malus x domestica ARF domain class transcription factor (ARF3) mRNA, complete cds.", XP002790323, retrieved from EBI accession No. EM_HTC:HM122438 Database accession No. HM122438.
Mimida et al., (2011) "Apple Flowering Locus T proteins interact with transcription factors implicated in cell growth and organ development" Tree Physiology 31, 555-566.
Nishimura et al., (2005) "The *Arabidopsis* STV1 Protein, Responsible for Translation Reinitiation, is Required for Auxin-Mediated Gynoecium Patterning," The Plant Cell, vol. 17, 2940-2953.
Okushima et al., (2005) "Functional Genomic Analysis of the Auxin Response Factor Gene Family Members in *Arabidopsis thaliana*: Unique and Overlapping Functions of ARF7 and ARF19," The Plant Cell, 17, 444-463.
Yang et al., (2020) "Development and validation of functional markers from Dw1 and Dw2 loci to accurately predict apple rootstock dwarfing ability" Research Square, 27 pp, doi. org/10.21203/rs.2.24669/v4.
Zhang et al., (2019) "A high-quality apple genome assembly reveals the association of a retrotransposon and red fruit colour" Nature Communications 10:1494, 13 pp.

* cited by examiner

FIGURE 3

|  | Arab ARF3 | tomato ARF3 | Citrus | VvARF | bean ARF3 | popARF | Prunus | strawbARF3 | Pear ARF3 | wt MdARF3 | M9 ARF3 |
|---|---|---|---|---|---|---|---|---|---|---|---|
| Arab ARF3 |  | 42.2% | 46.9% | 44.5% | 46.9% | 48.0% | 47.2% | 45.4% | 45.5% | 46.7% | 46.7% |
| tomato ARF3 | 42.2% |  | 50.9% | 55.6% | 55.1% | 50.7% | 53.3% | 49.1% | 50.8% | 53.1% | 53.0% |
| Citrus | 46.9% | 50.9% |  | 64.0% | 66.6% | 61.9% | 64.1% | 59.5% | 60.0% | 60.7% | 60.6% |
| VvARF | 44.5% | 55.6% | 64.0% |  | 64.7% | 60.0% | 63.4% | 58.3% | 59.1% | 58.8% | 58.7% |
| bean ARF3 | 46.9% | 55.1% | 66.6% | 64.7% |  | 68.6% | 63.3% | 58.8% | 59.0% | 62.1% | 62.1% |
| popARF | 48.0% | 50.7% | 61.9% | 60.0% | 68.6% |  | 59.8% | 57.3% | 58.0% | 58.9% | 58.9% |
| Prunus | 47.2% | 53.3% | 64.1% | 63.4% | 63.3% | 59.8% |  | 72.7% | 77.6% | 81.1% | 80.9% |
| strawbARF3 | 45.4% | 49.1% | 59.5% | 58.3% | 58.8% | 57.3% | 72.7% |  | 68.3% | 69.5% | 69.3% |
| Pear ARF3 | 45.5% | 50.8% | 60.0% | 59.1% | 59.0% | 58.0% | 77.6% | 68.3% |  | 89.2% | 89.1% |
| wt MdARF3 | 46.7% | 53.1% | 60.7% | 58.8% | 62.1% | 58.9% | 81.1% | 69.5% | 89.2% |  | 99.1% |
| M9 ARF3 | 46.7% | 53.0% | 60.6% | 58.7% | 62.1% | 58.9% | 80.9% | 69.3% | 89.1% | 99.1% |  |

FIGURE 9

```
                              SEQUENCE LISTING

<160> NUMBER OF SEQ ID NOS: 34

<210> SEQ ID NO 1
<211> LENGTH: 708
<212> TYPE: PRT
<213> ORGANISM: Malus domestica
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (403)..(403)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid

<400> SEQUENCE: 1

Met Ala Gly Leu Ile Asp Leu Asn Ser Ala Thr Glu Asp Glu Glu Thr
1               5                   10                  15

Pro Ser Ser Gly Ser Pro Ser Ser Ala Ser Ser Val Ser Asp Ala Leu
            20                  25                  30

Gly Ser Ser Ala Ser Val Cys Met Glu Leu Trp His Ala Cys Ala Gly
        35                  40                  45

Pro Leu Ile Ser Leu Pro Lys Lys Gly Ser Val Val Tyr Leu Pro
    50                  55                  60

Gln Gly His Leu Glu Gln Val Ser Asp Phe Pro Thr Ser Ala Tyr Asp
65              70                  75                  80

Leu Pro Pro His Leu Phe Cys Arg Val Val Asp Val Lys Leu His Ala
                85                  90                  95

Glu Thr Gly Thr Asp Asp Val Phe Ala Xaa Val Ser Leu Val Pro Glu
            100                 105                 110

Ser Glu Glu Ile Glu His Arg Leu Arg Glu Gly Val Thr Asp Ala Asp
        115                 120                 125

Ala Glu Glu Asp Val Glu Ala Met Gly Thr Ser Thr Thr Pro His Met
    130                 135                 140

Phe Cys Lys Thr Leu Thr Ala Ser Asp Thr Ser Thr His Gly Gly Phe
145                 150                 155                 160

Ser Val Pro Arg Arg Ala Ala Glu Asp Cys Phe Pro Pro Leu Asp Tyr
                165                 170                 175

Thr Gln Gln Arg Pro Ser Gln Glu Leu Val Ala Lys Asp Leu His Gly
            180                 185                 190
```

```
Leu Glu Trp Arg Phe Arg His Ile Tyr Arg Gly Gln Pro Arg Arg His
            195                 200                 205

Leu Leu Thr Thr Gly Trp Ser Ala Phe Val Asn Lys Lys Leu Val
    210                 215                 220

Ser Gly Asp Ala Val Leu Phe Leu Arg Gly Asp Asp Gly Glu Leu Arg
225                 230                 235                 240

Leu Gly Ile Arg Arg Ala Ala Gln Phe Lys Ser Ser Ala Thr Cys Pro
                245                 250                 255

Thr Leu Cys Ser Gln Gln Leu Asn Tyr Ser Thr Ile Thr Asp Val Val
            260                 265                 270

Asn Ala Ile Phe Ala Lys Asn Ala Phe Asn Val Tyr Tyr Asn Pro Arg
            275                 280                 285

Ser Ser Ser Ser Glu Phe Ile Ile Pro Ser His Lys Phe Leu Arg Ser
    290                 295                 300

Leu Asp His Cys Phe Cys Ala Gly Met Arg Ile Lys Met Arg Phe Glu
305                 310                 315                 320

Thr Glu Asp Ala Ala Glu Arg Arg Tyr Thr Gly Leu Ile Thr Gly Ile
                325                 330                 335

Ser Glu Leu Asp Pro Val Arg Trp Pro Gly Ser Lys Trp Arg Cys Leu
            340                 345                 350

Val Val Arg Trp Asp Asp Xaa Asp Thr Ser Lys His Gly Arg Val Ser
    355                 360                 365

Pro Trp Glu Val Glu Arg Ser Gly Val Ser Ser His Thr Leu
    370                 375                 380

Met Thr Thr Gly Leu Lys Arg Ser Arg Ile Gly Leu Ser Ala Thr Lys
385                 390                 395                 400

Pro Glu Xaa Pro Xaa Pro Ser Met Ser Cys Asn Xaa Gly Ile Gly Thr
                405                 410                 415

Ser Asp Phe Gly Glu Ser Leu Arg Phe Gln Lys Val Leu Gln Gly Gln
            420                 425                 430

Glu Ile Ser Gly Phe Asp Thr Pro Phe Ser Gly Leu Gly Gly Leu Asn
    435                 440                 445

Ser His Pro Ser Glu Ala Arg Arg Val Phe His Gly Ser Gly Gly Ser
    450                 455                 460

Gly Ile Ala Ala Xaa Gly Asn Gly Leu Arg Gln Ser Leu Val Asp Ser
465                 470                 475                 480

Glu Ile Ala Ser Lys Gly Ile Gly Phe Gly Glu Ser Phe Arg Phe His
                485                 490                 495

Lys Val Leu Gln Gly Gln Glu Ile Phe Pro Ser Ser Pro Tyr Gly Arg
            500                 505                 510

Ala Pro Ala Ser Asn Glu Ala His Glu Tyr Gly Gly Pro Gly Leu Tyr
    515                 520                 525

Asp Gly Phe Gln Val Pro Gly Phe Arg Asn Gly Xaa Ser Thr Met Met
530                 535                 540

Gln Ser Asn Asn Thr Asn Val His Ser Ser Ala Pro Ser Val Gln Val
545                 550                 555                 560

Ser Ser Pro Ser Ser Val Leu Met Phe Gln Gln Ala Met Asn Pro Val
                565                 570                 575

Ala Glu Phe Asn Ser Val Tyr Asn Gly His Asn Gln Glu Asp His Arg
            580                 585                 590

Val Asn Arg Thr Pro His Val Leu Glu His Asp Gly Gly Arg Gln Thr
    595                 600                 605
```

```
Ser Ser Ser Phe Gly Glu Arg Asn Phe Ser Arg Glu Asp Arg Gly Gly
    610                 615                 620

Thr His Ser Tyr Asn Gln His Gly Ile Ser Pro His Pro Val Ile Ser
625                 630                 635                 640

Gln Ser Thr Ile Ser Gly Ser Gln Asp Ser Val Ser Pro Ile Lys Gly
            645                 650                 655

Ser Cys Arg Leu Phe Gly Phe Ser Leu Ser Glu Asp Lys Cys Val Pro
            660                 665                 670

Asp Gln Glu Gly Asn Pro Asn Val Gly Val Gln Phe His Ser Lys Pro
            675                 680                 685

Pro Leu Met Thr Ser Thr Val Gly Ile Thr Cys Thr Lys Val Ser Asn
690                 695                 700

Leu Phe Ala Ala
705

<210> SEQ ID NO 2
<211> LENGTH: 708
<212> TYPE: PRT
<213> ORGANISM: Malus domestica
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (403)..(403)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid

<400> SEQUENCE: 2

Met Ala Gly Leu Ile Asp Leu Asn Ser Ala Thr Glu Asp Glu Glu Thr
1               5                   10                  15

Pro Ser Ser Gly Ser Pro Ser Ser Ala Ser Ser Val Ser Asp Ala Leu
            20                  25                  30

Gly Ser Ser Ala Ser Val Cys Met Glu Leu Trp His Ala Cys Ala Gly
        35                  40                  45

Pro Leu Ile Ser Leu Pro Lys Lys Gly Ser Val Val Tyr Leu Pro
    50                  55                  60

Gln Gly His Leu Glu Gln Val Leu Asp Phe Pro Thr Ser Ala Tyr Asp
65                  70                  75                  80

Leu Pro Pro His Leu Phe Cys Arg Val Val Asp Val Lys Leu His Ala
                85                  90                  95

Glu Thr Gly Thr Asp Asp Val Phe Ala Xaa Val Ser Leu Val Pro Glu
            100                 105                 110

Ser Glu Glu Ile Glu His Arg Leu Arg Glu Gly Val Thr Asp Ala Asp
```

```
            115                 120                 125
Ala Glu Glu Asp Val Glu Ala Met Gly Thr Ser Thr Thr Pro His Met
130                 135                 140

Phe Cys Lys Thr Leu Thr Ala Ser Asp Thr Ser Thr His Gly Gly Phe
145                 150                 155                 160

Ser Val Pro Arg Arg Ala Ala Glu Asp Cys Phe Pro Pro Leu Asp Tyr
                    165                 170                 175

Thr Gln Gln Arg Pro Ser Gln Glu Leu Val Ala Lys Asp Leu His Gly
                    180                 185                 190

Leu Glu Trp Arg Phe Arg His Ile Tyr Arg Gly Gln Pro Arg Arg His
            195                 200                 205

Leu Leu Thr Thr Gly Trp Ser Ala Phe Val Asn Lys Lys Lys Leu Val
210                 215                 220

Ser Gly Asp Ala Val Leu Phe Leu Arg Gly Asp Asp Gly Glu Leu Arg
225                 230                 235                 240

Leu Gly Ile Arg Arg Ala Ala Gln Phe Lys Ser Ser Ala Thr Cys Pro
                    245                 250                 255

Thr Leu Cys Ser Gln Gln Leu Asn Tyr Ser Thr Ile Thr Asp Val Val
                    260                 265                 270

Asn Ala Ile Phe Ala Lys Asn Ala Phe Asn Val Tyr Tyr Asn Pro Arg
                    275                 280                 285

Ser Ser Ser Glu Phe Ile Ile Pro Ser His Lys Phe Leu Arg Ser
290                 295                 300

Leu Asp His Cys Phe Cys Ala Gly Met Arg Ile Lys Met Arg Phe Glu
305                 310                 315                 320

Thr Glu Asp Ala Ala Glu Arg Arg Tyr Thr Gly Leu Ile Thr Gly Ile
                    325                 330                 335

Ser Glu Leu Asp Pro Val Arg Trp Pro Gly Ser Lys Trp Arg Cys Leu
                    340                 345                 350

Val Val Arg Trp Asp Asp Xaa Asp Thr Ser Lys His Gly Arg Val Ser
                    355                 360                 365

Pro Trp Glu Val Glu Arg Ser Gly Ser Val Ser Ser His Thr Leu
370                 375                 380

Met Thr Thr Gly Leu Lys Arg Ser Arg Ile Gly Leu Ser Ala Thr Lys
385                 390                 395                 400

Pro Glu Xaa Pro Xaa Pro Ser Met Ser Cys Asn Xaa Gly Ile Gly Thr
                    405                 410                 415

Ser Asp Phe Gly Glu Ser Leu Arg Phe Gln Lys Val Leu Gln Gly Gln
                    420                 425                 430

Glu Ile Ser Gly Phe Asp Thr Pro Phe Ser Gly Leu Gly Gly Leu Asn
                    435                 440                 445

Ser His Pro Ser Glu Ala Arg Arg Val Phe His Gly Ser Gly Gly Ser
                    450                 455                 460

Gly Ile Ala Ala Xaa Gly Asn Gly Leu Arg Gln Ser Leu Val Asp Ser
465                 470                 475                 480

Glu Ile Ala Ser Lys Gly Ile Gly Phe Gly Glu Ser Phe Arg Phe His
                    485                 490                 495

Lys Val Leu Gln Gly Gln Glu Ile Phe Pro Ser Ser Tyr Gly Arg
                    500                 505                 510

Ala Pro Ala Ser Asn Glu Ala His Glu Tyr Gly Gly Pro Gly Leu Tyr
                    515                 520                 525

Asp Gly Phe Gln Val Pro Gly Phe Arg Asn Gly Xaa Ser Thr Met Met
                    530                 535                 540
```

```
Gln Ser Asn Asn Thr Asn Val His Ser Ser Ala Pro Ser Val Gln Val
545                 550                 555                 560

Ser Ser Pro Ser Ser Val Leu Met Phe Gln Gln Ala Met Asn Pro Val
                565                 570                 575

Ala Glu Phe Asn Ser Val Tyr Asn Gly His Asn Gln Glu Asp His Arg
            580                 585                 590

Val Asn Arg Thr Pro His Val Leu Glu His Asp Gly Gly Arg Gln Thr
        595                 600                 605

Ser Ser Ser Phe Gly Glu Arg Asn Phe Ser Arg Glu Asp Arg Gly Gly
    610                 615                 620

Thr His Ser Tyr Asn Gln His Gly Ile Ser Pro His Pro Val Ile Ser
625                 630                 635                 640

Gln Ser Thr Ile Ser Gly Ser Gln Asp Ser Val Ser Pro Ile Lys Gly
                645                 650                 655

Ser Cys Arg Leu Phe Gly Phe Ser Leu Ser Glu Asp Lys Cys Val Pro
            660                 665                 670

Asp Gln Glu Gly Asn Pro Asn Val Gly Val Gln Phe His Ser Lys Pro
        675                 680                 685

Pro Leu Met Thr Ser Thr Val Gly Ile Thr Cys Thr Lys Val Ser Asn
    690                 695                 700

Leu Phe Ala Ala
705

<210> SEQ ID NO 3
<211> LENGTH: 608
<212> TYPE: PRT
<213> ORGANISM: Arabidopsis thaliana

<400> SEQUENCE: 3

Met Gly Gly Leu Ile Asp Leu Asn Val Met Glu Thr Glu Glu Asp Glu
1               5                   10                  15

Thr Gln Thr Gln Thr Pro Ser Ser Ala Ser Gly Ser Val Ser Pro Thr
                20                  25                  30

Ser Ser Ser Ser Ala Ser Val Ser Val Val Ser Ser Asn Ser Ala Gly
            35                  40                  45

Gly Gly Val Cys Leu Glu Leu Trp His Ala Cys Ala Gly Pro Leu Ile
        50                  55                  60

Ser Leu Pro Lys Arg Gly Ser Leu Val Leu Tyr Phe Pro Gln Gly His
65                  70                  75                  80

Leu Glu Gln Ala Pro Asp Phe Ser Ala Ala Ile Tyr Gly Leu Pro Pro
                85                  90                  95

His Val Phe Cys Arg Ile Leu Asp Val Lys Leu His Ala Glu Thr Thr
            100                 105                 110

Thr Asp Glu Val Tyr Ala Gln Val Ser Leu Leu Pro Glu Ser Glu Asp
        115                 120                 125

Ile Glu Arg Lys Val Arg Glu Gly Ile Ile Asp Val Asp Gly Gly Glu
    130                 135                 140

Glu Asp Tyr Glu Val Leu Lys Arg Ser Asn Thr Pro His Met Phe Cys
145                 150                 155                 160

Lys Thr Leu Thr Ala Ser Asp Thr Ser Thr His Gly Gly Phe Ser Val
                165                 170                 175

Pro Arg Arg Ala Ala Glu Asp Cys Phe Pro Pro Leu Asp Tyr Ser Gln
            180                 185                 190

Pro Arg Pro Ser Gln Glu Leu Leu Ala Arg Asp Leu His Gly Leu Glu
```

```
            195                 200                 205
Trp Arg Phe Arg His Ile Tyr Arg Gly Gln Pro Arg Arg His Leu Leu
210                 215                 220

Thr Thr Gly Trp Ser Ala Phe Val Asn Lys Lys Leu Val Ser Gly
225                 230                 235                 240

Asp Ala Val Leu Phe Leu Arg Gly Asp Gly Lys Leu Arg Leu Gly
                245                 250                 255

Val Arg Arg Ala Ser Gln Ile Glu Gly Thr Ala Leu Ser Ala Gln
            260                 265                 270

Tyr Asn Gln Asn Met Asn His Asn Asn Phe Ser Glu Val Ala His Ala
                275                 280                 285

Ile Ser Thr His Ser Val Phe Ser Ile Ser Tyr Asn Pro Lys Ala Ser
290                 295                 300

Trp Ser Asn Phe Ile Ile Pro Ala Pro Lys Phe Leu Lys Val Val Asp
305                 310                 315                 320

Tyr Pro Phe Cys Ile Gly Met Arg Phe Lys Ala Arg Val Glu Ser Glu
                325                 330                 335

Asp Ala Ser Glu Arg Arg Ser Pro Gly Ile Ile Ser Gly Ile Ser Asp
                340                 345                 350

Leu Asp Pro Ile Arg Trp Pro Gly Ser Lys Trp Arg Cys Leu Leu Val
                355                 360                 365

Arg Trp Asp Asp Ile Val Ala Asn Gly His Gln Gln Arg Val Ser Pro
370                 375                 380

Trp Glu Ile Glu Pro Ser Gly Ser Ile Ser Asn Ser Gly Ser Phe Val
385                 390                 395                 400

Thr Thr Gly Pro Lys Arg Ser Arg Ile Gly Phe Ser Ser Gly Lys Pro
                405                 410                 415

Asp Ile Pro Val Ser Glu Gly Ile Arg Ala Thr Asp Phe Glu Glu Ser
                420                 425                 430

Leu Arg Phe Gln Arg Val Leu Gln Gly Gln Glu Ile Phe Pro Gly Phe
            435                 440                 445

Ile Asn Thr Cys Ser Asp Gly Gly Ala Gly Ala Arg Arg Gly Arg Phe
            450                 455                 460

Lys Gly Thr Glu Phe Gly Asp Ser Tyr Gly Phe His Lys Val Leu Gln
465                 470                 475                 480

Gly Gln Glu Thr Val Pro Ala Tyr Ser Ile Thr Asp His Arg Gln Gln
                485                 490                 495

His Gly Leu Ser Gln Arg Asn Ile Trp Cys Gly Pro Phe Gln Asn Phe
                500                 505                 510

Ser Thr Arg Ile Leu Pro Pro Ser Val Ser Ser Ser Pro Ser Ser Val
            515                 520                 525

Leu Leu Thr Asn Ser Asn Ser Pro Asn Gly Arg Leu Glu Asp His His
            530                 535                 540

Gly Gly Ser Gly Arg Cys Arg Leu Phe Gly Phe Pro Leu Thr Asp Glu
545                 550                 555                 560

Thr Thr Ala Val Ala Ser Ala Thr Ala Val Pro Cys Val Glu Gly Asn
                565                 570                 575

Ser Met Lys Gly Ala Ser Ala Val Gln Ser Asn His His Ser Gln
                580                 585                 590

Gly Arg Asp Ile Tyr Ala Met Arg Asp Met Leu Leu Asp Ile Ala Leu
            595                 600                 605

<210> SEQ ID NO 4
```

<211> LENGTH: 730
<212> TYPE: PRT
<213> ORGANISM: Phaseolus vulgaris

<400> SEQUENCE: 4

```
Met Val Gly Ile Ile Asp Leu Asn Thr Thr Glu Glu Asp Lys Thr
1               5                   10                  15

Thr Pro Ser Ser Gly Ser Phe Ser Ser Pro Ser Ser Ser Ser Thr
                20                  25                  30

Ser Ala Ala Leu Ser Ala Thr Asn Leu Ser Ser Ala Pro Val Ser Gly
            35                  40                  45

Ser Val Cys Leu Glu Leu Trp His Ala Cys Ala Gly Pro Leu Ile Ser
50                  55                  60

Leu Pro Lys Lys Gly Ser Val Val Tyr Phe Pro Gln Gly His Leu
65                  70                  75                  80

Glu Gln Leu Pro Asp Leu Pro Leu Ala Val Tyr Asp Leu Pro Ser Tyr
                85                  90                  95

Ile Phe Cys Arg Val Val Asp Val Lys Leu His Ala Glu Thr Ala Asn
            100                 105                 110

Asp Glu Val Tyr Ala Gln Val Ser Leu Val Pro Asp Ser Glu Gln Ile
        115                 120                 125

Glu Gln Lys Leu Lys Gln Gly Lys Leu Glu Gly His Cys Glu Glu Glu
        130                 135                 140

Asp Val Glu Ala Val Val Lys Ser Thr Thr Thr His Met Phe Cys Lys
145                 150                 155                 160

Thr Leu Thr Ala Ser Asp Thr Ser Thr His Gly Gly Phe Ser Val Pro
                165                 170                 175

Arg Arg Ala Ala Glu Asp Cys Phe Pro Pro Leu Asp Tyr Ser Gln Gln
            180                 185                 190

Arg Pro Ser Gln Glu Leu Val Ala Lys Asp Leu His Gly Phe Glu Trp
        195                 200                 205

Lys Phe Arg His Ile Tyr Arg Gly Gln Pro Arg Arg His Leu Leu Thr
210                 215                 220

Thr Gly Trp Ser Ala Phe Val Asn Lys Lys Leu Val Ser Gly Asp
225                 230                 235                 240

Ala Val Leu Phe Leu Arg Gly Asp Gly Glu Leu Arg Leu Gly Ile
                245                 250                 255

Arg Arg Ala Ala Gln Val Lys Cys Gly Ala Ser Phe Pro Ala Leu Cys
            260                 265                 270

Ser Gln Gln Leu Asn Gln Ser Thr Leu Thr Asp Val Val His Ala Met
        275                 280                 285

Ser Met Arg Ser Leu Phe Asn Ile Cys Tyr Asn Pro Arg Ala Ser Ser
290                 295                 300

Ser Glu Phe Ile Ile Pro Leu His Lys Phe Leu Lys Ser Leu Asp Tyr
305                 310                 315                 320

Ser Phe Ser Val Gly Met Arg Phe Lys Met Arg Phe Glu Thr Glu Asp
                325                 330                 335

Ala Ala Glu Arg Arg Tyr Met Gly Leu Ile Thr Gly Ile Ser Asp Leu
            340                 345                 350

Asp Pro Ala Arg Trp Pro Gly Ser Lys Trp Arg Cys Leu Val Val Arg
        355                 360                 365

Trp Asp Asp Met Glu Thr Asn Arg His Ser Arg Val Ser Pro Trp Glu
370                 375                 380

Ile Glu Pro Ser Gly Ser Val Ser Ser Cys Asn Ser Phe Met Thr Pro
```

```
                385                 390                 395                 400
Gly Leu Lys Arg Ser Arg Ser Gly Phe Pro Ser Ser Lys Pro Glu Phe
                    405                 410                 415

Pro Val Pro Asp Gly Ile Gly Ala Ser Asp Phe Gly Glu Pro Ser Arg
                420                 425                 430

Phe Gln Lys Val Leu Gln Gly Gln Glu Ile Leu Asn Phe Asn Thr Leu
            435                 440                 445

Tyr Asp Gly Val Asp Gln Asn Arg His Pro Ser Asp Ile Arg Arg Cys
        450                 455                 460

Phe Pro Gly Ser Arg Ser Met Ile Ala Thr Thr Arg Asn Gly Ala
465                 470                 475                 480

Arg Asp Pro Val Val Asn Ser Asp Val Ser Tyr Lys Ser Ile Gly Phe
                485                 490                 495

Ser Glu Ser Leu Arg Phe His Lys Val Leu Gln Gly Gln Glu Ile Ile
                500                 505                 510

Pro Ser Ser Pro Phe Gly Arg Ala Pro Ala Ser Thr Asn Glu Ala Cys
            515                 520                 525

Glu Asn Gly Cys Phe Gly Ile Ser Asp Gly Val Gln Met Thr Ser Ser
        530                 535                 540

Arg Asn Gly Trp Ser Ser Met Met Gln Gly Tyr Asn Thr Arg Ile Arg
545                 550                 555                 560

Pro Pro Ala Gln Val Ser Ser Pro Cys Ser Val Leu Met Phe Gln Gln
                565                 570                 575

Ala Ser Asn Gln Val Ser Asn Pro Ser Pro Arg Tyr Gly Phe Asn Asp
            580                 585                 590

Leu Glu Glu Gln Gly Val Asn Thr Gln Ser Trp Phe His Asn Pro Glu
        595                 600                 605

Thr Cys Gly Glu Lys Arg Met Ser Ser Arg Ser Glu His Ile Phe
610                 615                 620

Arg Arg Asn Asn Gln Trp Gly Met Asp Ser Phe Ser Leu Ser His Glu
625                 630                 635                 640

His Ser Gln His Gly Leu Leu Gln Pro Leu Val Ala Gln Pro Pro Cys
                645                 650                 655

Lys Gly Gly Gln Asp Leu Val Ser Ser Cys Lys Ser Ser Cys Arg Leu
            660                 665                 670

Phe Gly Phe Gln Leu Thr Glu Asp Arg His Val Ala Asn Lys Asp Asp
        675                 680                 685

Ser Ser Ile Pro Met Ala Ser Leu Asn Ala Gly Ser Phe Met Pro His
690                 695                 700

Ala Gly Glu Gln Phe His Leu Lys Pro Pro Ala Ile Thr Asn Ala Val
705                 710                 715                 720

Gly Ser Ser Cys Thr Lys Val Ser Val Leu
                725                 730

<210> SEQ ID NO 5
<211> LENGTH: 747
<212> TYPE: PRT
<213> ORGANISM: Solanum lycopersicum

<400> SEQUENCE: 5

Met Met Cys Gly Leu Ile Asp Leu Asn Thr Val Asp Asn Asp Asp Ala
1               5                   10                  15

Gly Glu Glu Thr Thr Ala Pro Val Ser Leu Asp Ser Pro Ala Ser Ser
            20                  25                  30
```

```
Ser Ala Ala Ser Gly Ser Ser Asp Leu Thr Ser Ser Thr Pro Ala
         35                  40                  45
Val Ala Ser Val Cys Met Glu Leu Trp His Ala Cys Ala Gly Pro Leu
 50                  55                  60
Ile Ser Leu Pro Lys Lys Gly Ser Ala Val Val Tyr Leu Pro Gln Gly
65                   70                  75                  80
His Leu Glu His Leu Ser Glu Tyr Pro Ser Ile Ala Cys Asn Leu Pro
                 85                  90                  95
Pro His Val Phe Cys Arg Val Val Asp Val Lys Leu Gln Ala Asp Ala
            100                 105                 110
Ala Thr Asp Glu Val Tyr Ala Gln Val Ser Leu Val Pro Asp Asn Gln
        115                 120                 125
Gln Ile Glu Gln Lys Trp Lys Asp Gly Asp Ile Asp Ala Asp Ile Glu
    130                 135                 140
Glu Glu Glu Ile Glu Gly Ala Gly Lys Ser Ile Thr Pro His Met Phe
145                 150                 155                 160
Cys Lys Thr Leu Thr Ala Ser Asp Thr Ser His Gly Gly Phe Ser
                165                 170                 175
Val Pro Arg Arg Ala Ala Glu Asp Cys Phe Ala Pro Leu Asp Tyr Arg
            180                 185                 190
Gln Gln Arg Pro Ser Gln Glu Leu Val Ala Lys Asp Leu His Gly Ile
        195                 200                 205
Glu Trp Lys Phe Arg His Ile Tyr Arg Gly Gln Pro Arg Arg His Leu
    210                 215                 220
Leu Thr Thr Gly Trp Ser Ala Phe Val Asn Lys Lys Lys Leu Val Ser
225                 230                 235                 240
Gly Asp Ala Val Leu Phe Leu Arg Thr Gly Asp Gly Glu Leu Arg Leu
            245                 250                 255
Gly Val Arg Arg Ala Ala Gln Ala Lys Thr Cys Ser Ser Tyr Leu Ala
        260                 265                 270
Pro Cys Ser Lys Pro Leu Asn Val Ser Gly Ile Val Asp Ala Val Asn
    275                 280                 285
Val Ile Ser Ser Arg Asn Ala Phe Asn Ile Cys Tyr Asn Pro Arg Asp
290                 295                 300
Ser Ser Ser Asp Phe Ile Val Pro Tyr His Lys Phe Ser Lys Thr Leu
305                 310                 315                 320
Ala His Pro Phe Ser Ala Gly Met Arg Phe Lys Met Arg Val Glu Thr
            325                 330                 335
Glu Asp Ala Ala Glu Gln Arg Phe Thr Gly Leu Val Val Gly Val Ser
        340                 345                 350
Asn Val Asp Pro Val Arg Trp Pro Gly Ser Lys Trp Arg Cys Leu Leu
    355                 360                 365
Val Arg Trp Asp Asp Leu Asp Val Ser Arg His Asn Arg Val Ser Pro
370                 375                 380
Trp Glu Ile Glu Pro Ser Gly Ser Ala Pro Val Pro Ser Ser Leu Val
385                 390                 395                 400
Met Pro Ser Ala Lys Arg Thr Arg Val Gly Phe Pro Ile Ser Lys Ala
            405                 410                 415
Asp Phe Pro Ile Pro Arg Glu Gly Ile Ala Val Ser Asp Phe Gly Glu
        420                 425                 430
Pro Ser Arg Phe Gln Lys Val Leu Gln Gly Gln Glu Ile Leu Arg Met
    435                 440                 445
His Ala Pro Tyr Gly Gly Leu Asp Ala Arg Ser Pro Arg Pro Ala Gly
```

```
                    450                 455                 460

Thr Arg Cys Phe Pro Gly Phe Pro Ser Ser Gly Ile Ser Arg Met Gly
465                 470                 475                 480

Asn Ser Ile Arg Pro Leu Phe Gly Asp Thr Asp Lys Ser His Glu Ser
                485                 490                 495

Ile Gly Phe Ser Glu Ser Leu Arg Phe Asn Lys Val Leu Gln Gly Gln
            500                 505                 510

Glu Ile Phe Thr Ser Pro Pro Tyr Gly Arg Ala Gln Ala Gly Ile Gln
        515                 520                 525

Met Gln Glu Lys Ser Arg Thr Gly Ile Phe Val Gly Ile Gln Val Pro
530                 535                 540

Asn His Gly Asn Arg Trp Pro Ala Pro Asn Gln Asp Asn Asn Thr Pro
545                 550                 555                 560

Cys Lys Pro Ile Asn Pro Val Ser Ala Ser Ser Pro Pro Ser Ala Leu
                565                 570                 575

Asn Phe Gln His Pro Ser Pro Pro Ala Ser Lys Phe Gln Ala Met Phe
            580                 585                 590

Asn His Lys His Asp Leu Val Asn Gln Ala Ser Leu Asp Leu Ser Glu
        595                 600                 605

Asn Cys Cys Arg Tyr Pro Tyr Leu Ser Ser Gly Ser His Thr Glu Asp
    610                 615                 620

Ile Ser Gln Lys Glu Gly Thr Gln Gly Ile Ser Ser Phe Gly Phe Leu
625                 630                 635                 640

Lys Glu Gln Lys Gln Thr Gly Leu Ser Tyr Leu Ser Pro Gly Thr Gln
                645                 650                 655

Ser Ser Phe Lys Gly Asn Gln Asn Leu Val Ser Thr Cys Lys Thr Gly
            660                 665                 670

Cys Arg Ile Phe Gly Phe Pro Leu Thr Glu Ser Lys Ile Ser Ala Thr
        675                 680                 685

Arg Ala Asp Thr Pro Ser Glu Ala Val Tyr Ser His Gly Leu Glu Thr
    690                 695                 700

Thr Phe Leu Pro Ser Ser Asp Gly Lys Leu Gln Pro Gly Pro Pro Leu
705                 710                 715                 720

Met Thr Asn Val Val Gly Thr Asn Phe Thr Lys Val Asn Asp Leu Tyr
                725                 730                 735

Ala Ala Arg Asp Val Leu Leu Asp Ile Ala Leu
            740                 745

<210> SEQ ID NO 6
<211> LENGTH: 743
<212> TYPE: PRT
<213> ORGANISM: Citrus clemantina

<400> SEQUENCE: 6

Met Val Gly Leu Ile Asp Leu Asn Thr Thr Glu Asp Asp Glu Asn Pro
1               5                   10                  15

Ser Ser Gly Ser Leu Ser Pro Ser Ser Ser Ala Ser Ala Leu Ser
                20                  25                  30

Ala Ser Gly Phe Ala Leu Ala Pro Ala Ser Ala Ser Ala Ser Gly Val
            35                  40                  45

Ser Leu Glu Leu Trp His Ala Cys Ala Gly Pro Leu Ile Ser Leu Pro
        50                  55                  60

Lys Arg Gly Ser Val Val Val Tyr Phe Pro Gln Gly His Leu Glu His
65                  70                  75                  80
```

```
Val Ser Asp Phe Ser Ala Ala Ser Ala Ala Tyr Asp Leu Pro Pro
                85                  90                  95

His Leu Phe Cys Arg Val Ala Asp Val Lys Leu His Ala Glu Ala Ala
            100                 105                 110

Ser Asp Glu Val Tyr Ala Gln Val Ser Leu Val Pro Asp Glu Leu Ile
        115                 120                 125

Glu Gln Lys Val Arg Glu Gly Lys Ile Glu Glu Asp Gly Asp Glu Glu
    130                 135                 140

Ser Val Glu Val Val Ala Lys Ser Ser Thr Pro His Met Phe Cys Lys
145                 150                 155                 160

Thr Leu Thr Ala Ser Asp Thr Ser Thr His Gly Gly Phe Ser Val Pro
                165                 170                 175

Arg Arg Ala Ala Glu Asp Cys Phe Pro Pro Leu Asp Tyr Ser Gln Gln
            180                 185                 190

Arg Pro Ser Gln Glu Leu Val Ala Lys Asp Leu His Gly Leu Glu Trp
        195                 200                 205

Arg Phe Arg His Ile Tyr Arg Gly Gln Pro Arg Arg His Leu Leu Thr
    210                 215                 220

Thr Gly Trp Ser Ala Phe Val Asn Lys Lys Leu Val Ser Gly Asp
225                 230                 235                 240

Ala Val Leu Phe Leu Arg Gly Glu Asp Gly Glu Leu Arg Leu Gly Ile
                245                 250                 255

Arg Arg Ala Pro His Val Lys Ser Gly Ala Thr Phe Pro Ser Phe Cys
            260                 265                 270

Ser Gln Gln Ser Ser Pro Asn Ser Val Thr Glu Val Val Asp Ala Ile
        275                 280                 285

Ala Arg Lys Arg Ala Phe Ser Ile Ser Tyr Asn Pro Arg Ala Ser Ala
    290                 295                 300

Ser Glu Phe Ile Ile Pro Val Asn Lys Phe Leu Lys Ser Leu Gly His
305                 310                 315                 320

Ser Phe Ala Val Gly Met Arg Phe Lys Met Arg Phe Glu Thr Glu Asp
                325                 330                 335

Ala Ala Glu Arg Arg Tyr Thr Gly Val Ile Met Gly Val Gly Asp Met
            340                 345                 350

Asp Pro Val Arg Trp Pro Gly Ser Lys Trp Arg Cys Leu Leu Val Arg
        355                 360                 365

Trp Asp Asp Val Glu Ser Asn Arg His Thr Arg Val Ser Pro Trp Glu
    370                 375                 380

Ile Glu Pro Ser Gly Ser Val Cys Gly Ser Asn Asn Leu Ile Thr Ser
385                 390                 395                 400

Gly Leu Lys Arg Thr Arg Ile Gly Leu Pro Ser Gly Lys Pro Glu Phe
                405                 410                 415

Pro Val Pro Asp Gly Ile Gly Val Thr Asp Phe Gly Glu Ser Leu Arg
            420                 425                 430

Phe Gln Lys Val Leu Gln Gly Gln Glu Ile Leu Gly Phe Asn Thr Leu
        435                 440                 445

Tyr Asp Gly Gly Asp Cys Gln Asn Leu His Pro Ser Glu Val Arg Arg
    450                 455                 460

Gly Ile Pro Gly Ser Asn Ser Gly Ile Ala Ala Ile Gly Asp Gly
465                 470                 475                 480

Ser Arg Asn Leu Gln Val Lys Ser Asp Ile Ser Tyr Lys Gly Ile Gly
                485                 490                 495

Ile Gly Phe Gly Glu Ser Phe Arg Phe His Lys Val Leu Gln Gly Gln
```

-continued

```
                500             505             510
Glu Ile Phe Pro Lys Ser Pro Tyr Gly Arg Ala Pro Thr Asn Asn Glu
            515                 520                 525

Ala Arg Ser Ile Gly Ser Leu Gly Ile Ser Asp Gly Val Pro Val Ser
530                 535                 540

Gly Ser Arg Asn Arg Trp Ser Ala Val Val Pro Gly Tyr Asn Thr His
545                 550                 555                 560

Met Ser Pro Ser Ala Pro Pro Val Gln Val Ser Ser Pro Ser Ser Val
                565                 570                 575

Leu Met Phe Gln Leu Ala Ser Asn Pro Ile Ser Asn Tyr Asn Pro Pro
            580                 585                 590

Tyr Ser Leu Asn Asp Gln Glu Lys Glu Gln Arg Val Asn Cys Gln Ser
        595                 600                 605

Phe Phe His Asn Ser Glu Ile Tyr Gly Gly Lys His Ala Ser Ser Ser
    610                 615                 620

Phe Leu Asp His Ser Phe Val Gly Gly Asp Gln Glu Val Met Asp Ser
625                 630                 635                 640

Ile Gly Gln Ser Asn Glu His Ile Ser Pro Pro Leu Val Gly Gln Pro
                645                 650                 655

Thr Val Arg Gly Ser Gln Asp Leu Val Ser Ser Cys Lys Gly Ser Cys
            660                 665                 670

Arg Leu Phe Gly Phe Ser Leu Thr Glu Glu Arg His Val Ala Asn Ile
        675                 680                 685

Glu Asp Asn Ala Ala Pro Val Ala Ser Pro Leu Asn Pro Arg Ser Ser
    690                 695                 700

Phe Leu Ser His Val Gly Gln Gln Phe His Pro Lys Pro Val Met
705                 710                 715                 720

Ser Lys Ala Thr Gly Ser Asn Cys Thr Asn Gly Ile Met Gln His Cys
                725                 730                 735

Leu Gly Asn Tyr Asp Ile Tyr
            740

<210> SEQ ID NO 7
<211> LENGTH: 720
<212> TYPE: PRT
<213> ORGANISM: Fragaria vesca

<400> SEQUENCE: 7

Met Ala Gly Leu Ile Asp Leu Asn Ser Thr Thr Glu Glu Glu Glu Glu
1               5                   10                  15

Thr Pro Ser Ser Gly Ser Ser Ser Asn Ser Ser Gly Ser Asn Gly Leu
            20                  25                  30

Ile Ser Gly Ser Val Cys Leu Glu Leu Trp His Ala Cys Ala Gly Pro
        35                  40                  45

Leu Ile Ser Leu Pro Lys Lys Gly Ser Val Val Tyr Leu Pro Gln
    50                  55                  60

Gly His Leu Glu Gln Val Ser Asp Phe Pro Ala Ser Val Tyr Asp Leu
65                  70                  75                  80

Pro Ala His Leu Phe Cys Arg Val Leu Asp Val Lys Leu His Ala Glu
                85                  90                  95

Ser Gly Ser Asp Glu Val Tyr Ala Gln Val Gln Leu Val Pro Glu Ser
            100                 105                 110

Glu Glu Phe Glu His Lys Leu Gly Glu Arg Glu Thr Val Ala Asp Gly
        115                 120                 125
```

```
Asp Glu Asp Ala Glu Gly Ser Glu Lys Ser Thr Thr Pro His Met Phe
130                 135                 140

Cys Lys Thr Leu Thr Ala Ser Asp Thr Ser Thr His Gly Gly Phe Ser
145                 150                 155                 160

Val Pro Arg Arg Ala Ala Glu Asp Cys Phe Pro Pro Leu Asp Tyr Ser
                165                 170                 175

Gln Gln Arg Pro Ser Gln Glu Leu Val Ala Lys Asp Leu His Gly Leu
            180                 185                 190

Glu Trp Arg Phe Arg His Ile Tyr Arg Gly Gln Pro Arg Arg His Leu
        195                 200                 205

Leu Thr Thr Gly Trp Ser Ala Phe Val Asn Lys Lys Leu Val Ser
210                 215                 220

Gly Asp Ala Val Leu Phe Leu Arg Gly Glu Asp Gly Glu Leu Arg Leu
225                 230                 235                 240

Gly Val Arg Arg Ala Ala Gln Val Lys Ala Ser Ala Thr Tyr Pro Thr
                245                 250                 255

Pro Gly Ser Gln His Leu Asn Tyr Asn Ser Val Thr Glu Leu Val Asp
            260                 265                 270

Ala Ile Ser Thr Lys Thr Ala Phe Asn Ala Tyr Tyr Asn Pro Arg Ala
        275                 280                 285

Ser Ser Ser Glu Phe Ile Ile Pro Phe Arg Lys Phe Leu Arg Ser Leu
290                 295                 300

Gly His Ser Phe Cys Ala Gly Met Arg Phe Lys Met Arg Phe Glu Thr
305                 310                 315                 320

Glu Asp Ala Ala Glu Gln Arg Tyr Thr Gly Leu Val Thr Gly Ile Ser
                325                 330                 335

Glu Leu Asp Pro Leu Arg Trp Pro Gly Ser Lys Trp Lys Cys Val Ala
            340                 345                 350

Val Arg Trp Asp Asp Ile Asp Thr Ser Lys Gln His Gly Arg Val Ser
        355                 360                 365

Pro Trp Glu Ile Glu Pro Ser Gly Ser Ile Ser Asn Ser Ser Gly Leu
370                 375                 380

Met Ala Ser Gly Leu Lys Arg Ser Arg Met Gly Leu Ser Ala Glu Lys
385                 390                 395                 400

Gln Glu Phe Pro Val Pro His Gly Ile Gly Ala Ser Asp Phe Gly Glu
                405                 410                 415

Ser Leu Arg Phe Gln Lys Val Leu Gln Gly Gln Glu Val Ser Gly Phe
            420                 425                 430

Asp Thr Pro Phe Gly Ser Ile Gly Gly Gln Asn Gln His Pro Ser Glu
        435                 440                 445

Ser Arg Arg Val Phe His Gly Ser Ile Gly Ser Arg Gly Asn Asp Leu
450                 455                 460

Arg Asn Ser Phe Val Asn Ser Glu Ile Ala Ser Lys Gly Phe Gly Glu
465                 470                 475                 480

Ser Phe Arg Phe Gln Lys Val Leu Gln Gly Gln Glu Ile Phe Pro Ser
                485                 490                 495

Thr Pro Tyr Gly Arg Ala Pro Ala Thr Asn Glu Ala Arg Glu Tyr Gly
            500                 505                 510

Cys Pro Gly Ile Phe Asp Gly Phe Gln Val Pro Ser Phe Arg Asn Gly
        515                 520                 525

Trp Ser Thr Met Met Gln Gly Ser Asn Thr Pro Met His Arg Ala Ala
530                 535                 540

Pro Val Gln Val Ser Ser Pro Ser Ser Val Leu Met Phe Gln Gln Ala
```

```
            545                 550                 555                 560
        Ile Asn Ala Gly Ala Glu Phe Asn Ser Val Tyr Asn Gly His Asn Gln
                        565                 570                 575

Gln Glu Gln Arg Ile Met Gln Arg Thr His Ser Glu Ser Asp Gly Gly
                        580                 585                 590

Lys Gln Thr Ser Ala Ser Phe Cys Glu Arg Ser Phe Thr Arg Glu Gly
                        595                 600                 605

His Gly Gly Met Asn Ser Phe Asp Gln His Gly Ile Ser His Pro Pro
                        610                 615                 620

Leu Leu Ser Gln Ser Ser Leu Arg Gly Ser Gln Asp Met Val Ser Ser
        625                 630                 635                 640

Cys Lys Ser Ser Cys Arg Leu Phe Gly Phe Ser Leu Ser Glu Glu Thr
                        645                 650                 655

His Ala Pro Asn Lys Val Asp Asn Ser Thr Ser Val Thr Ser Ala Leu
                        660                 665                 670

Glu Ser Gly Ala Ser Met Phe Pro Asn Val Glu Pro Arg Phe His Ser
                        675                 680                 685

Lys Pro Pro Ser Met Ser Ala Ala Val Gly Ile Pro Cys Thr Lys Glu
                        690                 695                 700

Trp Ala Phe Asn Trp Arg Gly Glu Arg Met Glu Ser Cys Leu Gln Gly
        705                 710                 715                 720

<210> SEQ ID NO 8
<211> LENGTH: 722
<212> TYPE: PRT
<213> ORGANISM: Prunus persica

<400> SEQUENCE: 8

Met Gly Gly Leu Ile Asp Leu Asn Ser Ala Thr Glu Asp Glu Glu Thr
        1               5                   10                  15

Pro Ser Ser Gly Ser Ser Thr Ser Ser Ala Ser Asp Ala Ser Ala
                        20                  25                  30

Ser Ala Ser Ala Ser Val Cys Leu Glu Leu Trp His Ala Cys Ala Gly
                        35                  40                  45

Pro Leu Ile Ser Leu Pro Lys Lys Gly Ser Val Val Tyr Leu Pro
                50                  55                  60

Gln Gly His Leu Glu Gln Val Ser Asp Phe Pro Ala Ser Ala Tyr Asn
        65                  70                  75                  80

Leu Pro Pro His Leu Phe Cys Arg Val Val Asp Val Lys Leu His Ala
                        85                  90                  95

Glu Thr Gly Thr Asp Asp Val Tyr Ala Gln Val Ser Leu Val Pro Glu
                        100                 105                 110

Ser Glu Glu Ile Glu His Lys Leu Arg Glu Gly Glu Thr Asp Ala Tyr
                        115                 120                 125

Gly Glu Glu Glu Asp Val Glu Ala Ile Gly Lys Ser Thr Thr Pro His
        130                 135                 140

Met Phe Cys Lys Thr Leu Thr Ala Ser Asp Thr Ser Thr His Gly Gly
        145                 150                 155                 160

Phe Ser Val Pro Arg Arg Ala Ala Glu Asp Cys Phe Pro Pro Leu Asp
                        165                 170                 175

Tyr Asn Gln Gln Arg Pro Ser Gln Glu Leu Val Ala Lys Asp Leu His
                        180                 185                 190

Gly Leu Glu Trp Arg Phe Arg His Ile Tyr Arg Gly Gln Pro Arg Arg
                        195                 200                 205
```

-continued

```
His Leu Leu Thr Thr Gly Trp Ser Ala Phe Val Asn Lys Lys Leu
    210                 215                 220

Val Ser Gly Asp Ala Val Leu Phe Leu Arg Gly Asp Gly Glu Leu
225                 230                 235                 240

Arg Leu Gly Ile Arg Arg Ala Ala Gln Val Lys Gly Ser Ala Thr Tyr
                245                 250                 255

Pro Thr Leu Cys Ser Gln Gln Leu Asn Tyr Asn Thr Ile Thr Asp Val
                260                 265                 270

Val Asn Ala Ile Ser Met Lys Asn Ala Phe Asn Ile Phe Tyr Asn Pro
                275                 280                 285

Arg Ala Ser Ser Ser Glu Phe Ile Ile Pro Ser Arg Lys Phe Leu Arg
290                 295                 300

Ser Leu Asp His Ser Phe Ser Pro Gly Met Arg Phe Lys Met Arg Phe
305                 310                 315                 320

Glu Thr Glu Asp Ala Ala Glu Arg Arg Tyr Thr Gly Leu Ile Thr Gly
                325                 330                 335

Ile Ser Glu Leu Asp Pro Val Arg Trp Pro Gly Ser Lys Trp Arg Cys
                340                 345                 350

Leu Val Val Arg Trp Asp Asp Ile Asp Thr Ser Lys His Gly Arg Val
                355                 360                 365

Ser Pro Trp Glu Ile Glu Pro Ser Gly Ser Val Ser Ser Ser His Ser
    370                 375                 380

Leu Met Ala Ala Gly Leu Lys Arg Ala Arg Ser Gly Leu Ser Ala Ala
385                 390                 395                 400

Lys Thr Glu Phe Pro Val Pro Asn Gly Ile Gly Ala Ser Asp Phe Gly
                405                 410                 415

Glu Ser Leu Arg Phe Gln Lys Val Leu Gln Gly Gln Glu Ile Leu Gly
                420                 425                 430

Phe Asp Thr His Phe Gly Gly Leu Gly Gly Gln Asn Gln His Pro Ser
                435                 440                 445

Glu Pro Arg Arg Gly Phe His Gly Ser Ser Gly Ser Gly Ile Ala Ala
    450                 455                 460

Gly Gly Asn Gly Leu Arg Lys Ser Leu Ala His Ser Glu Ile Thr Ser
465                 470                 475                 480

Thr Gly Ile Gly Phe Gly Glu Ser Phe Arg Phe His Lys Val Leu Gln
                485                 490                 495

Gly Gln Glu Ile Phe Pro Ser Pro Tyr Gly Arg Ala Ser Thr Asn
                500                 505                 510

Asn Glu Ala His Glu Tyr Gly Gly Pro Gly Ile Tyr Asp Gly Phe Gln
                515                 520                 525

Val Pro Ser Phe Arg Asn Gly Trp Pro Ala Met Met Gln Ser Asn Asn
530                 535                 540

Ala His Val Arg Pro Ser Ala Ser Ser Val Gln Val Ser Ser Pro Ser
545                 550                 555                 560

Ser Val Leu Met Phe Gln Gln Ala Met Asn Pro Gly Pro Glu Phe Asn
                565                 570                 575

Ser Val Tyr Asn Gly His Asn Gln Glu Glu Gln Arg Val Ile Lys Arg
                580                 585                 590

Thr Pro Tyr Val Ser Glu Ser Asp Gly Gly Lys Gln Ala Ser Ser Ser
                595                 600                 605

Phe Cys Glu Arg Ser Phe Ser Arg Glu Asp His Gly Gly Met Asn Ser
    610                 615                 620

Tyr Asn Gln His Gly Ile Ser Asn His Pro Val Ile Ser Gln Ser Thr
```

```
                625                 630                 635                 640
        Phe Ser Gly Ser Gln Asp Ala Val Ser Pro Tyr Lys Gly Ser Cys Arg
                        645                 650                 655

Leu Phe Gly Phe Ser Leu Ser Glu Glu Lys Arg Val Pro Asp Arg Glu
                        660                 665                 670

Ser Asn Ser Thr Ser Thr Ala Ser Thr Leu Asn Pro Gly Val Gln Phe
                        675                 680                 685

His Ser Lys Pro Ala Leu Met Thr Ser Ala Val Gly Ile Thr Cys Thr
                        690                 695                 700

Lys Glu Trp Ala Phe Asp Trp Arg Gly Glu Arg Met Glu Ser Cys Leu
        705                 710                 715                 720

Gln Gly

<210> SEQ ID NO 9
<211> LENGTH: 704
<212> TYPE: PRT
<213> ORGANISM: Pyrus communis

<400> SEQUENCE: 9

Met Ala Gly Leu Ile Asp Leu Asn Ser Ala Thr Glu Asp Glu Gln Thr
1               5                   10                  15

Pro Ser Ser Gly Ser Pro Ser Ser Ala Ser Ser Val Ser Asp Ala Leu
                20                  25                  30

Gly Ser Ala Ser Val Cys Met Glu Leu Trp His Ala Cys Ala Gly
                35                  40                  45

Pro Leu Ile Ser Leu Pro Lys Lys Gly Ser Val Val Tyr Leu Pro
50                  55                  60

Gln Gly His Leu Glu Gln Val Ser Asp Phe Pro Thr Ser Ala Tyr Asp
65              70                  75                  80

Leu Pro Pro His Leu Phe Cys Arg Val Val Asp Val Lys Leu His Ala
                85                  90                  95

Glu Thr Gly Thr Asp Asp Val Phe Ala Arg Val Ser Leu Val Pro Glu
                100                 105                 110

Ser Glu Glu Ile Glu His Arg Leu Arg Glu Gly Glu Thr Asp Ala Asp
                115                 120                 125

Ala Glu Asp Asp Val Glu Ala Met Gly Thr Ser Ala Thr Pro His Met
130                 135                 140

Phe Cys Lys Thr Leu Thr Ala Ser Asp Thr Ser Thr His Gly Gly Phe
145                 150                 155                 160

Ser Val Pro Arg Arg Ala Ala Glu Asp Cys Phe Pro Pro Leu Asp Tyr
                165                 170                 175

Thr Gln Gln Arg Pro Ser Gln Glu Leu Val Ala Lys Asp Leu His Gly
                180                 185                 190

Leu Glu Trp Arg Phe Arg His Ile Tyr Arg Gly Gln Pro Arg Arg His
                195                 200                 205

Leu Leu Thr Thr Gly Trp Ser Ala Phe Val Asn Lys Lys Lys Leu Val
            210                 215                 220

Ser Gly Asp Ala Val Leu Phe Leu Arg Gly Asp Asp Gly Glu Leu Arg
225                 230                 235                 240

Leu Gly Ile Arg Arg Ala Ala Gln Phe Lys Ser Ser Ala Thr Cys Pro
                245                 250                 255

Thr Leu Cys Ser Gln Gln Leu Asn Cys Ser Ala Ile Thr Asp Val Leu
                260                 265                 270

Asn Ala Ile Phe Ala Lys Asn Ala Phe Asn Val Tyr Tyr Asn Pro Arg
```

-continued

```
                275                 280                 285
Ser Ser Ser Ser Glu Phe Ile Ile Pro Ser His Lys Phe Leu Arg Ser
    290                 295                 300
Leu Asp His Cys Phe Ser Ala Gly Met Arg Ile Lys Met Arg Phe Glu
305                 310                 315                 320
Thr Glu Asp Ala Ala Glu Arg Arg Tyr Ile Gly Phe Ile Thr Arg Ile
                325                 330                 335
Ser Glu Leu Asp Pro Val Arg Trp Pro Gly Ser Lys Trp Arg Cys Leu
            340                 345                 350
Val Val Arg Trp Asp Asp Ile Asp Thr Ser Lys His Ser Arg Val Ser
        355                 360                 365
Pro Trp Glu Val Glu Pro Ser Gly Val Ser Ser His Thr Leu
370                 375                 380
Met Ala Thr Gly Leu Lys Arg Ser Arg Ile Gly Leu Ser Ala Thr Lys
385                 390                 395                 400
Pro Glu Cys Ser Val Pro Asn Gly Gly Ile Gly Thr Ser Asp Phe Gly
                405                 410                 415
Glu Ser Leu Arg Phe Gln Lys Val Leu Gln Gly Gln Glu Ile Ser Gly
            420                 425                 430
Phe Asp Thr Pro Phe Ser Gly Leu Gly Gly Leu Asn Ser Leu Pro Ser
        435                 440                 445
Glu Ala Arg Arg Val Phe His Gly Ser Gly Gly Ser Gly Ile Ala Ala
    450                 455                 460
Gly Gly Asn Gly Leu Arg Gln Ser Leu Val Asp Ser Glu Ile Ala Ser
465                 470                 475                 480
Lys Gly Ile Gly Phe Gly Glu Ser Phe Arg Phe Arg Lys Val Leu Gln
                485                 490                 495
Gly Gln Glu Ile Leu Pro Ser Ser Pro Tyr Gly Arg Ala Pro Ala Ser
            500                 505                 510
Asn Glu Ala His Glu Tyr Gly Gly Pro Gly Ile Tyr Asp Gly Phe His
        515                 520                 525
Val Pro Gly Phe Arg Asn Gly Trp Ser Thr Met Met Gln Ser Asn Asn
    530                 535                 540
Thr His Val His Ser Ser Ala Pro Ser Val Gln Val Ser Ser Pro Ser
545                 550                 555                 560
Ser Val Leu Met Phe Gln Gln Ala Val Asn Pro Val Val Glu Phe Asn
                565                 570                 575
Ser Val Tyr Asn Gly His Asn Pro Glu Asp His Arg Val Asn Arg Thr
            580                 585                 590
Leu His Val Ser Glu His Asp Gly Gly Arg Gln Thr Ser Ser Ser Phe
        595                 600                 605
Gly Glu Leu Asn Phe Ser Arg Glu Asp Arg Gly Thr His Ser Tyr
    610                 615                 620
Asn Gln His Gly Ile Ser Pro His Pro Gly Thr Ser Gln Ser Thr Ile
625                 630                 635                 640
Ser Gly Ser Gln Asp Ser Ile Ser Pro Ile Lys Gly Ser Cys Arg Leu
                645                 650                 655
Phe Gly Phe Ser Leu Ser Glu Asp Lys Cys Val Pro Asp Gln Glu Gly
            660                 665                 670
Asn Pro Asn Val Gly Val Arg Phe His Ser Lys Pro Ser Leu Met Thr
        675                 680                 685
Ser Thr Val Gly Ile Thr Cys Thr Lys Val Ser Asn Leu Phe Ala Ala
    690                 695                 700
```

<210> SEQ ID NO 10
<211> LENGTH: 709
<212> TYPE: PRT
<213> ORGANISM: Populus tremula

<400> SEQUENCE: 10

```
Met Val Gly Met Ile Asp Leu Asn Thr Thr Glu Asp Glu Thr Thr
1               5                   10                  15

Pro Ser Ser Gly Ser Leu Ser Ser Ser Ser Ser Ala Ala Ser
            20                  25                  30

Ala Leu Ser Ala Ser Gly Ser Gly Ser Gly Thr Ser Pro Val Cys Leu
            35                  40                  45

Glu Leu Trp His Ala Cys Ala Gly Pro Leu Ile Ser Leu Pro Lys Arg
    50                  55                  60

Gly Ser Ile Val Val Tyr Val Pro Gln Gly His Leu Glu Gln Leu Pro
65                  70                  75                  80

Asp Leu Pro Leu Gly Ile Tyr Asp Leu Pro Pro His Val Phe Cys Arg
                85                  90                  95

Val Val Asp Val Lys Leu His Ala Glu Ala Ala Ser Asp Asp Val Tyr
            100                 105                 110

Ala Gln Val Ser Leu Val Pro Glu Ser Glu Glu Ile Glu Gln Lys Leu
        115                 120                 125

Arg Glu Gly Val Phe Glu Gly Asp Gly Glu Glu Asp Val Glu Ala
    130                 135                 140

Thr Val Lys Thr Thr Thr Pro His Met Phe Cys Lys Thr Leu Thr Ala
145                 150                 155                 160

Ser Asp Thr Ser Thr His Gly Gly Phe Ser Val Pro Arg Arg Ala Ala
                165                 170                 175

Glu Asp Cys Phe Pro Pro Leu Asp Tyr Thr Gln Gln Arg Pro Ser Gln
            180                 185                 190

Glu Leu Val Ala Lys Asp Leu His Gly Ser Glu Trp Lys Phe Arg His
        195                 200                 205

Ile Tyr Arg Gly Gln Pro Arg Arg His Leu Leu Thr Thr Gly Trp Ser
    210                 215                 220

Ala Phe Val Asn Lys Lys Lys Leu Val Ser Gly Asp Ala Val Leu Phe
225                 230                 235                 240

Leu Arg Gly Glu Asp Gly Glu Leu Arg Leu Gly Val Arg Arg Ala Ala
                245                 250                 255

Gln Val Lys Cys Gly Pro Thr Phe Pro Ala Leu Trp Asn Gln Gln Leu
            260                 265                 270

Asn Gln Ser Ser Leu Ala Asp Val Ala Asn Ala Ile Ser Met Arg Ser
        275                 280                 285

Ala Phe Arg Ile Tyr Tyr Asn Pro Arg Ala Ser Ser Ser Glu Phe Ile
    290                 295                 300

Ile Pro Phe Asn Lys Phe Leu Lys Ser Leu Asp Gln Ser Phe Ser Ala
305                 310                 315                 320

Gly Met Arg Val Lys Met Arg Phe Glu Thr Glu Asp Ala Ala Glu Arg
                325                 330                 335

Arg Tyr Thr Gly Leu Ile Thr Gly Ile Ser Glu Leu Asp Pro Thr Arg
            340                 345                 350

Trp Pro Gly Ser Lys Trp Lys Cys Leu Leu Val Arg Trp Asp Asp Thr
        355                 360                 365

Glu Ala Asn Arg His Ser Arg Val Ser Pro Trp Glu Val Glu Pro Ser
```

```
                370                 375                 380
Gly Ser Val Ser Gly Ser Gly Ser Ile Ser Ser Asn Asn
385                 390                 395                 400

Ser Met Ala Pro Gly Leu Lys Arg Ser Arg Ser Gly Leu Pro Ser Leu
                405                 410                 415

Lys Ala Glu Phe Pro Ile Pro Asp Gly Ile Ala Ser Asp Phe Arg
                420                 425                 430

Val Ser Ser Arg Phe Gln Glu Val Leu Gln Gly Gln Glu Ile Met Arg
            435                 440                 445

Ser Gly Ile Arg Gly Ser Ile Pro Thr Ser Glu Asn Ser Phe Lys Gly
            450                 455                 460

Ile Gly Phe Asn Glu Ser Tyr Arg Phe His Lys Val Leu Gln Gly Gln
465                 470                 475                 480

Glu Ile Phe Pro Arg Ser Pro Tyr Arg Arg Ile Pro Asn Ala Asn Lys
                485                 490                 495

Ala Arg Glu Asn Cys Gly Leu Gly Leu Ser Asp Gly Val Gln Arg Ser
                500                 505                 510

Ser Ser Arg Asn Gly Trp Ser Thr Met Met Gln Gly Tyr Asn Thr Gln
            515                 520                 525

Met Arg Pro Pro Thr Gln Val Ser Ser Pro Ser Ser Val Leu Met Phe
            530                 535                 540

Gln His Ala Ser Asn Gln Val Ser Asn Pro Thr Ser Ile Phe Asn Ser
545                 550                 555                 560

Asn Asp His Glu Glu Gln Thr Thr Asn Thr Gln Ser Trp Phe Tyr Pro
                565                 570                 575

Glu Thr His Gly Gly Lys Phe Lys Leu Ser Ser His Ser Asp Pro Gly
                580                 585                 590

Leu Arg Gly Asp Ser Gln Cys Ser Thr Asn Pro Tyr Val Leu Ser His
            595                 600                 605

Glu His Leu Gln His Gly Ile Ser Gln Pro Val Val Ala Gln Ser Ala
            610                 615                 620

Phe Arg Ser Ser Gln Asp Met Val Leu Cys Lys Ser Ser Cys Arg Leu
625                 630                 635                 640

Phe Gly Phe Ser Leu Thr Glu Asp Arg His Val Val Asn Lys Glu Asp
                645                 650                 655

Asn Ile Ala Ser Ile Thr Ser Pro Leu Asn Pro Glu Ser Ser Phe Leu
                660                 665                 670

Pro Arg Val Gly Glu Gln Leu His Pro Lys Pro Pro Ala Ile Asn Asn
            675                 680                 685

Ala Val Gly Ser Ser Cys Thr Lys Ala Ile Arg Gln His His Ala Glu
            690                 695                 700

Asn Tyr Arg Ile Tyr
705

<210> SEQ ID NO 11
<211> LENGTH: 786
<212> TYPE: PRT
<213> ORGANISM: Vitis vinifera

<400> SEQUENCE: 11

Met Val Ala Met Ile Asp Leu Asn Thr Val Asp Asp Glu Thr Pro
1               5                   10                  15

Ser Ser Gly Ser Ser Ser Ser Ser Ser Ala Ser Ala Ser Ala
                20                  25                  30
```

```
Ser Thr Val Cys Gly Ser Leu Leu Ser Ala Ala Ser Ser Val Cys Leu
         35                  40                  45

Glu Leu Trp His Ala Cys Ala Gly Pro Leu Ile Ser Leu Pro Lys Lys
 50                  55                  60

Gly Ser Leu Val Val Tyr Phe Pro Gln Gly His Leu Glu Gln Leu Ser
 65                  70                  75                  80

Asp Tyr Pro Ala Val Ala Tyr Asp Leu Pro Pro His Val Phe Cys Arg
                 85                  90                  95

Val Val Asp Val Lys Leu His Ala Glu Val Val Thr Asp Glu Val Tyr
            100                 105                 110

Ala Gln Val Ser Leu Val Pro Glu Thr Lys Gln Ile Lys Gln Lys Leu
        115                 120                 125

Gln Glu Gly Glu Ile Glu Ala Asp Gly Gly Glu Glu Asp Ile Glu
    130                 135                 140

Gly Ser Ile Lys Ser Met Thr Pro His Met Phe Cys Lys Thr Leu Thr
145                 150                 155                 160

Ala Ser Asp Thr Ser Thr His Gly Gly Phe Ser Val Pro Arg Arg Ala
                165                 170                 175

Ala Glu Asp Cys Phe Pro Pro Leu Asp Tyr Lys Gln Gln Arg Pro Ser
            180                 185                 190

Gln Glu Leu Val Ala Lys Asp Leu His Gly Phe Glu Trp Arg Phe Arg
        195                 200                 205

His Ile Tyr Arg Gly Gln Pro Arg Arg His Leu Leu Thr Thr Gly Trp
    210                 215                 220

Ser Ala Phe Val Asn Lys Lys Lys Leu Val Ser Gly Asp Ala Val Leu
225                 230                 235                 240

Phe Leu Arg Gly Gly Asp Gly Glu Leu Arg Leu Gly Ile Arg Arg Ala
                245                 250                 255

Ala Gln Ile Lys Gly Ser Ser Pro Phe Pro Ala Leu Cys Ser Gln Gln
            260                 265                 270

Leu Asn Leu Asn Thr Leu Thr Ala Val Val Asn Ala Ile Ser Thr Arg
        275                 280                 285

Ser Val Phe Asn Ile Cys Tyr Asn Pro Arg Ala Ser Ser Ser Glu Phe
    290                 295                 300

Ile Ile Pro Leu Arg Lys Phe Ser Lys Ser Ile Asp His Ser Phe Ser
305                 310                 315                 320

Ala Gly Met Arg Phe Lys Met Arg Val Glu Thr Glu Asp Ala Ala Glu
                325                 330                 335

Arg Arg Tyr Thr Gly Leu Ile Thr Gly Ile Ser Asp Met Asp Pro Val
            340                 345                 350

Arg Trp Pro Gly Ser Lys Trp Arg Cys Leu Leu Val Arg Trp Asp Asp
        355                 360                 365

Ile Glu Ala Asn Arg His Asn Arg Val Ser Pro Trp Glu Ile Glu Leu
    370                 375                 380

Ser Gly Ser Leu Ser Gly Ser Gly Ser Leu Thr Val Pro Gly Ser Lys
385                 390                 395                 400

Arg Thr Arg Ile Gly Leu Pro Gly Thr Arg Pro Asp Phe Ser Val Pro
                405                 410                 415

Asn Gly Met Gly Val Ser Asp Phe Gly Glu Ser Ser Arg Phe Gln Lys
            420                 425                 430

Val Leu Gln Gly Gln Glu Ile Phe Gly Phe Asn Thr Pro Tyr Asp Gly
        435                 440                 445

Val Asp Thr Gln Asp His His Pro Ser Glu Ile Arg Cys Phe Pro Gly
```

```
      450               455               460
Ser Ser Cys Ser Gly Ile Ala Ala Ile Gly Asn Gly Val Arg Asn Pro
465               470              475              480

Leu Gly Asn Ser Asp Ile Ser Tyr Lys Gly Ile Gly Phe Gly Glu Ser
                    485              490              495

Phe Arg Phe His Lys Val Leu Gln Gly Gln Glu Thr Phe Pro Ser Pro
                500              505              510

Pro Cys Gly Arg Ala Leu Ser Ala Asn Gln Ala His Glu Asn Gly Ser
            515              520              525

Phe Gly Ile Phe Asp Gly Val Gln Val Pro Thr Ser Arg Asn Gly Trp
        530              535              540

Pro Ala Leu Val Gln Gly Tyr Asn Ala His Thr His Leu Ser Thr Pro
545              550              555              560

Ser Val Gln Val Ser Ser Pro Ser Ser Val Leu Met Phe Gln Gln Ala
                565              570              575

Ser Thr Ala Ala Pro Asn Ile Tyr Ser Met His Ser Ala Asn Asn Gln
                580              585              590

Glu Lys Glu Gln Glu Ile Ser Asn Arg Ser Ser Phe Asp Ile Pro Glu
            595              600              605

Val Tyr Gly Glu Lys Leu Thr Pro Ser Arg Cys Glu Leu Ser Val Arg
        610              615              620

Gly Gly Gly Gln Gly Gly Met Asn Phe Phe Gly Leu Leu Asn Glu His
625              630              635              640

Asn Gln Leu Ala Val Pro His Pro Leu Val Thr Gln Ser Ala Phe Arg
                645              650              655

Gly Ser Gln Asp Leu Val Pro Thr Cys Lys Ser Ser Cys Arg Leu Phe
                660              665              670

Gly Phe Ser Leu Thr Glu Glu Arg Ser Ile Gly Asn Lys Val Asp Asn
            675              680              685

Pro Thr Pro Val Thr Ser Ser Leu Ile Pro Gly Thr Ser Phe Leu Pro
        690              695              700

Gln Gln Leu His Ser Glu Pro Pro Val Met Thr Lys Ala Ile Gly Ser
705              710              715              720

Asn Cys Thr Lys Arg Thr Ala Val Val Arg Ser Lys Leu Gln Phe His
                725              730              735

Lys Leu Gly Ser Val Val Asp Gln Ala Ile Asn Arg Trp Lys Leu Asp
                740              745              750

Arg His Asp Asp Leu Ile Cys Ala Leu Lys His Leu Phe Asp Met Glu
            755              760              765

Gly Gly Leu Leu His Gly Glu Gly Lys Leu Phe Thr Arg Ile Met Arg
        770              775              780

Met Leu
785

<210> SEQ ID NO 12
<211> LENGTH: 2127
<212> TYPE: DNA
<213> ORGANISM: Malus domestica

<400> SEQUENCE: 12
atggcgggtc taattgatct gaacagtgcg acggaggacg aggaaacgcc atcgtccggc    60
tcgccgtctt cggcttcctc tgtttccgac gctctgggtt cgtcggcgtc ggtgtgcatg   120
gagctctgga cgcctgcgc gggcccactg atttcgctgc cgaagaaagg gagtgtggtg   180
```

```
gtgtatctgc cgcagggcca cctggagcaa gtctcggatt ttccgacctc ggcttatgat    240
ctcccgcccc acctcttctg tcgggttgtc gatgtcaagc tccatgctga gactggcact    300
gacgatgtct tcgctcrggt ttcccttgtt cctgaaagtg aggaaattga gcacagattg    360
cgggaagggg taaccgatgc agatgccgag gaggacgttg aggcaatggg gacgtcaacc    420
acaccccaca tgttctgcaa aacccttact gcttctgata ctagcactca cggaggcttc    480
tctgtgcctc gtcgtgctgc cgaggattgc tttcctcccc tggattacac tcaacaaagg    540
ccttcacaag agcttgtagc aaaggatctg catggcctgg agtggaggtt ccggcatatc    600 tataggggc agccgcggag gcatttgctc accactgggt ggagtgcgtt tgtgaacaag    660
aagaagctcg tctctggaga tgcagtgctg tttcttaggg gtgacgatgg agaactgagg    720
ctaggaatta aagggcagc ccagtttaaa agttctgcta cttgtccaac tctttgtagc    780
cagcaattga actatagcac tatcactgat gtggtgaatg ctatattcgc gaagaatgct    840
tttaatgtgt actacaatcc aaggtccagc tcttctgaat tcataatacc ttcccataag    900
tttttgagga gccttgatca ttgttttgt gctggaatga ggatcaaaat gcgttttgaa    960
actgaagatg cagcagagcg aagatacact gggttgataa cggggattag tgaattggat   1020
cctgtaagat ggcctggttc aaaatggaga tgcctagttg tcaggtggga tgatrtagac   1080
acaagcaagc atggcagggt ttccccatgg gaagttgagc gatctggttc tgtttctagt   1140
tcccataccc taatgacaac tggcttgaag cggtccagga ttggcttgtc tgcaacaaaa   1200
ccagaatktc cagytcctag tatgtcctgc aatyatggga ttggaacatc agactttggg   1260
gaatctttaa ggttccagaa ggtcttgcaa ggtcaagaaa tttcggggtt tgatactcct   1320
ttcagtggtt taggtggtct gaattcgcat ccatctgaag caaggagagt cttccacggt   1380
tccggtggtt ctgggattgc tgctggrggt aatggtctca gacagtcact tgtggattct   1440
gagattgcct caaaaggcat aggctttggt gaatcattcc gattccataa ggtcttgcaa   1500
ggtcaagaaa tatttccaag ctcaccatat ggaagagctc ccgcttctaa tgaagctcat   1560
gaatatggtg gacctggact ctatgatggt tttcaggtgc ctggctttag gaatggatgs   1620
tccaccatga tgcagagcaa taatacaaat gtgcactcat ctgccccatc tgtgcaagtt   1680
tcatcacctt cgtctgtgtt aatgttccag caagcaatga atccagttgc ggaattcaac   1740
tcggtataca atggccataa ccaagaggac catagagtaa atcggactcc acatgtcttg   1800
gaacatgatg gtggaaggca acatcatccc tcattcggtg aacgtaactt cagcagggaa   1860
gatcgtggag gcacacattc ttacaatcag catggtattt cacctcatcc agttataagt   1920
caatcaacaa ttagtggcag ccaggattct gtttcaccaa tcaaaggtag ctgtagactc   1980
tttggtttct cattgtccga ggacaaatgt gtcccggatc aagagggcaa ccccaatgtt   2040
ggagtgcagt ttcattcaaa gcctcctttg atgacctcaa cagttggaat aacctgtact   2100
aaagtaagca acctctttgc tgcatga                                        2127
```

<210> SEQ ID NO 13
<211> LENGTH: 5500
<212> TYPE: DNA
<213> ORGANISM: Malus domestica

<400> SEQUENCE: 13

```
actctcccac gatacccacc tagcaaatgc taaattytct cgctcccaa atgttctgca     60 atcaggcagg cargggttta gtaattagtc gggtcaaaga ctcggataca ctaatttcaa    120
aataaagaaa tgttatagat cggagkattg tgccttggca gacaagccct ctttcaacag    180
```

```
gkttacatat gagggwtaag caatattaaa tatagattct acaaactttt gttctcaaag    240
ctgaattaac aatacaaatc aaagtcccct ggagcgctta gttacaactt ctgcctcaaa    300
attaagttac ataaatgaca gcacacacat aatcccgaag aaaacctccg cctgtcgaga    360
gttttcttca tcggtacaac gcaaaactat tgatattaca gtaacatcgc ctgccaaaag    420
cgaaattcaa acaaataaat gaccggaaca caagcatctt cttcatgttc atccggttta    480
cttaaaacga cttggaagg atatagtgcg gcgacaaaca tggccatgat gagttccatg     540
ggtagggttt ataagcggac ttcraggcat accatatgta agttttgaca atagacgggc    600
aatgaagaat gccatgtaga ttccgatgct aggttgcaaa cagaacaaaa atagrcaaat    660
acaataagta aacgtacgag gacttactag ttactgcctc ggatcatctg caacaagcac    720
aggatgatca ctatccttgt aaacagcttt ccatcctttc tccgcgccag tcaaaagccc    780
aatcctagac ataaacatcc cacttgctaa tcagataatc atttgcttcc gtcaaataga    840
agattaaata ccccagtcgt aacatttgaa aattgtattt catgcagcaa agaggttgct    900
tactttagta caggttattc caactgttga ggtcatcaaa ggaggctttg aatgaaactg    960
cactccaaca ttggggttgc cctcttgatc cgggacacat tgtcctcgg acaatgagaa     1020 accaaagagt ctacagctac ctttgattgg tgaaacagaa tcctggctgc cactaattgt    1080
tgattgactt ataactggat gaggtgaaat accatgctga ttgtaagaat gtgtgcctcc    1140
acgatcttcc ctgctgaagt tacgttcacc gaatgaggat gatgtttgcc ttccaccatc    1200
atgttccaag acatgtggag tccgattac tctatggtcc tcttggttat ggccattgta     1260
taccgagttg aattccgcaa ctggattcat tgcttgctgg aacattaaca cagacgaagg    1320
tgatgaaact tgcacagatg gggcagatga gtgcacattt gtattattgc tctgcatcat    1380
ggtggascat ccattcctaa agccaggcac ctgaaaacca tcatagagtc caggtccacc    1440
atattcatga gcttcattag aagcgggagc tcttccatat ggtgagcttg gaaatatttc    1500
ttgaccttgc aagaccttat ggaatcggaa tgattcacca aagcctatgc cttttgaggc    1560
aatctcagaa tccacaagtg actgtctgag accattaccy ccagcagcaa tcccagaacc    1620
accggaaccg tggaagactc tccttgcttc agatggatgc gaattcagac cacctaaacc    1680
actgaaagga gtatcaaacc ccgaaatttc ttgaccttgc aagaccttct ggaaccttaa    1740
agattcccca aagtctgatg ttccaatccc atctgaaaag gaaacactca ataaatcaa     1800 ttatgttgca gagaccagtg ttatgatgac atgtcgtggt acrattgcag gacatactag    1860
garctggama ttctggtttt gttgcagaca agccaatcct ggaccgcttc aagccagttg    1920
tcattagggt atgggaacta gaaacagaac cagatcgctc aacttcccat ggggaaaccc    1980
tgccatgctt gcttgtgtct ayatcatccc acctgacctg caatagcaaa agaaatgttc    2040
aaacctatat atctagtgct aatggcatga gcgaataccg gaagtcaata tggacatgct    2100
acagaataga ggaaacatag tttatgatat ttaggtaaac gactttcaag acagtgaaaa    2160
ttaactctca ctatcaagac ataattgctc ataaaccctg agtttctact ccgtaggact    2220
atgagtaggg tggcttgatc aacaattaag ataaaactgt gtagctaatg cgggagaaaa    2280
tttatgcttc cagtttaaat ttagccagaa attctaccaa attgtgacat ttcacatgac    2340
atatgaagtg tgcaattcat cctagttaga atacggtgaa gccggctaca tttttttttgt    2400 tacctttgc actctcatgc ttcaactatt gttgagaaaa gcttatcata gatttgttca     2460
tgacaatggt tttgggaatc tcaaagtaaa ataaccaata cgtatagtaa gtctcccata    2520
```

```
aagaagataa tacagaattt atggtacgct aaagataact tttggtttag tacattggca    2580
ttcaccaccc gaaccttctc aagcagatac ttataagtgc aaacaaaggg gaaaaaatag    2640
tacataaaag ttttgtgtag aaaatacgta caactaggca tctccatttt gaaccaggcc    2700
atcttacagg atccaattca ctaatccccg ttatcaaccc agtgtatctg ccaaaaagaa    2760
aaatttaata aaaattttgc acaaaactac ttcaactatt tcaaagtaa gaatgccaaa     2820 ccttcgctct gctgcatctt cagtttcaaa acgcattttg atcctcattc cagcacaaaa    2880
acaatgatca aggctcctca aaaacttatg ggaaggtatt atgaattcag aagagctgga    2940
cctacaagat catggacgat tataaggaaa aaagatgcag aaggaagaaa ggtctaaagt    3000
ctcaagcacg ataactttca acattacttt aggaacatgt taaatgatga gcaccagatt    3060
accttggatt gtagtacaca ttaaaagcat tcttcgcgaa tatagcattc accacatcag    3120
tgatagtgct atagttcaat tgctggctac aaagagttgg acaagtagca aacttttaa     3180 actgggctgc ccttctaatt cctagcctca gttctccatc gtcaccccta ttataaatac    3240
tggatgagaa ttataaataw ggggatccaa aatctcttca atcgaagggt ttatatacct    3300
aagaaacagc actgcatctc cagagacgag cttcttcttg ttcacaaacg cactccaccc    3360
agtggtgagc aaatgcctcc gcggctgccc tactcaaacc aattagaaaa aaggaataag    3420
aaacagaaaa acgttgaatc taaagcatcc aatttacaaa gttcattata aaactctaat    3480
aagattgcta ccgtatcatg gaaagataaa cccccaacta atgaagcaca aaagggatca    3540
tattttttgt attaccccta tagatatgcc ggaacctcca ctccaggcca tgcagatcct    3600
ttgctacaag ctcttgtgaa ggcctttgtt gagtgtaatc ctaaaagcac aatctattcg    3660
tctcaaaaac aaaatactaa tatgtacttg attagactaa taatttagtc tcaaaaaagt    3720
tatgcagaag ctaaamcaaa agttgggga gaacatgaac taggaatacc agggaggaa     3780 agcaatcctc ggcagcacga cgaggcacag agaagcctcc gtgagtgcta gtatcagaag    3840
cagtaagggt tttgcagaac atgtggggtg tggttgacgt ccccattgcc tcaacgtcct    3900
cctcggcatc tgcatcggtt accccttccc gcaatctgtg ctcaatttcc tacaccgatt    3960
aaagcattag tgaaatcacc tcaatgtcaa tgtttaacag acaaaaacat cacamgatca    4020
ccaggaagag caaagaaaat taaaaaacay caaccccgaa atcgaattgt ataaattata    4080
agtaactaat tcataaattt gtgaaatgac taattgtaag garacagaga tgctaacata    4140
taatcttcga taatgccaaa gtgggaaaga aagaaagtga aattctaaag cttgcgtttt    4200
taattgtttc ggtttctacg gaagggagg attttctcag aattttttta cttttcgagc     4260
attttctcag gaaccaaaca aaaatcaaa ccttgtacaa ataaaccac ctcactttca      4320 ggaacaaggg aaaccygagc gaagacatcg tcagtgccag tctcagcctg cgaccaaaaa    4380
agacctcaag aaattgagaa cccagatagc aaaacccaa aagctatcaa atttcatcaa     4440
aaatccaaaa ccccaaaagc atggagaaag agaggctcat tgtatagaga gagactgaca    4500
tggagcttga catcgacaac ccgacagaag aggtggggcg ggagatcata agccgaggtc    4560
ggaaaatccg agacttgctc caggtggccc tgcggcagat acaccaccac actcccttc     4620 ttcggcagcg aaatcagtgg gcccgcgcag gcgtgccaga gctccatgca caccgacgcc    4680
gacgaaccca gagcgtcgga aacagaggaa gccgaagacg gcgagccgga cgatggcgtt    4740
tcctcgtcct ccgtcgcact gttcagatca attagacccg ccatgtgaaa ttaaacagaa    4800
actgtaagga cccaacaagc gaaagaggaa gaagaaggag aaaagcactt tgcttttttg    4860 cttttttgctt ctgcttctgc ttaagcttgt ttataatatg gagaagagaa aaaaragagc    4920
```

| | |
|---|---:|
| agatgaggtt tcaattctcc tgcattttga gagatgggtt tgatggcatt tttgctaaaa | 4980 |
| gaagctcaga aaagcacttc tctctctttt ctgcttaatt cttaactttt atttatttt | 5040 |
| cttttggacg ggcttttggg tatcaaatca aaagctcaaa gcttttacaa tttgggagat | 5100 |
| gagaaaaga aaatgaaat taataccaaa aaaaatcaga taatttaata tgggacttct | 5160 |
| tttggtgttg aattgaatcc ctttttgggt ttaaatta caaagatta aacctttct | 5220 |
| ctctgtctgc aggctgaact gcaacactgc aattgctggg tgtgatgtgt ggcagaaaca | 5280 |
| gtgtgtcaga gagtgagaga gagaggaaga gagagagtgg aggtcttgta cggcaccccc | 5340 |
| tgtatttccg ggcggatgtc tattctgtcc ccttctactc cgtcaaatcc cactcgtatc | 5400 |
| ccccccccc tcttccttaa tcttcattct ctccttcctc ccatatttaa tttattttaa | 5460 |
| ttaaggagga tgtagttaaa ctaagatttt aaaagatttt | 5500 |

<210> SEQ ID NO 14
<211> LENGTH: 2127
<212> TYPE: DNA
<213> ORGANISM: Malus domestica

<400> SEQUENCE: 14

| | |
|---|---:|
| atggcgggtc taattgatct gaacagtgcg acggaggacg aggaaacgcc atcgtccggc | 60 |
| tcgccgtctt cggcttcctc tgtttccgac gctctgggtt cgtcggcgtc ggtgtgcatg | 120 |
| gagctctggc acgcctgcgc gggcccactg atttcgctgc gaagaaagg gagtgtggtg | 180 |
| gtgtatctgc cgcagggcca cctggagcaa gtcttggatt ttccgacctc ggcttatgat | 240 |
| ctcccgcccc acctcttctg tcgggttgtc gatgtcaagc tccatgctga gactggcact | 300 |
| gacgatgtct tcgctcrggt ttcccttgtt cctgaaagtg aggaaattga gcacagattg | 360 |
| cgggaagggg taaccgatgc agatgccgag gaggacgttg aggcaatggg gacgtcaacc | 420 |
| acaccccaca tgttctgcaa aacccttact gcttctgata ctagcactca cggaggcttc | 480 |
| tctgtgcctc gtcgtgctgc cgaggattgc tttcctcccc tggattacac tcaacaaagg | 540 |
| ccttcacaag agcttgtagc aaaggatctg catggcctgg agtggaggtt ccggcatatc | 600 |
| tataggggc agccgcggag gcatttgctc accactgggt ggagtgcgtt tgtgaacaag | 660 |
| aagaagctcg tctctggaga tgcagtgctg tttcttaggg gtgacgatgg agaactgagg | 720 |
| ctaggaatta aagggcagc ccagtttaaa agttctgcta cttgtccaac tctttgtagc | 780 |
| cagcaattga actatagcac tatcactgat gtggtgaatg ctatattcgc gaagaatgct | 840 |
| tttaatgtgt actacaatcc aaggtccagc tcttctgaat tcataatacc ttcccataag | 900 |
| ttttgagga gccttgatca ttgttttgt gctggaatga ggatcaaaat gcgttttgaa | 960 |
| actgaagatg cagcagagcg aagatacact ggggttgataa cggggattag tgaattggat | 1020 |
| cctgtaagat ggcctggttc aaaatggaga tgcctagttg tcaggtggga tgatrtagac | 1080 |
| acaagcaagc atggcagggt ttccccatgg gaagttgagc gatctggttc tgtttctagt | 1140 |
| tcccataccc taatgacaac tggcttgaag cggtccagga ttggcttgtc tgcaacaaaa | 1200 |
| ccagaatktc cagytcctag tatgtcctgc aatyatggga ttggaacatc agactttggg | 1260 |
| gaatctttaa ggttccagaa ggtcttgcaa ggtcaagaaa tttcggggtt tgatactcct | 1320 |
| ttcagtggtt taggtggtct gaattcgcat ccatctgaag caaggagagt cttccacggt | 1380 |
| tccggtggtt ctgggattgc tgctggrggt aatggtctca gacagtcact tgtggattct | 1440 |
| gagattgcct caaaaggcat aggctttggt gaatcattcc gattccataa ggtcttgcaa | 1500 |

```
ggtcaagaaa tatttccaag ctcaccatat ggaagagctc ccgcttctaa tgaagctcat    1560
gaatatggtg gacctggact ctatgatggt tttcaggtgc ctggctttag gaatggatgs    1620
tccaccatga tgcagagcaa taatacaaat gtgcactcat ctgccccatc tgtgcaagtt    1680
tcatcacctt cgtctgtgtt aatgttccag caagcaatga atccagttgc ggaattcaac    1740
tcggtataca atggccataa ccaagaggac catagagtaa atcggactcc acatgtcttg    1800
gaacatgatg gtgaaggca aacatcatcc tcattcggtg aacgtaactt cagcagggaa    1860
gatcgtggag gcacacattc ttacaatcag catggtattt caccctcatcc agttataagt    1920 caatcaacaa ttagtggcag ccaggattct gtttcaccaa tcaaaggtag ctgtagactc    1980
tttggtttct cattgtccga ggacaaatgt gtcccggatc aagagggcaa ccccaatgtt    2040
ggagtgcagt ttcattcaaa gcctcctttg atgacctcaa cagttggaat aacctgtact    2100
aaagtaagca acctctttgc tgcatga                                        2127

<210> SEQ ID NO 15
<211> LENGTH: 5500
<212> TYPE: DNA
<213> ORGANISM: Malus domestica

<400> SEQUENCE: 15
aaaatctttt aaaatcttag tttaactaca tcctccttaa ttaaaataaa ttaaatatgg      60
gaggaaggag agaatgaaga ttaaggaaga gggggggggg gatacgagtg ggatttgacg     120
gagtagaagg ggacagaata gacatccgcc cggaaataca gggggtgccg tacaagacct     180
ccactctctc tcttcctctc tctctcactc tctgacacac tgtttctgcc acacatcaca     240
cccagcaatt gcagtgttgc agttcagcct gcagacagag agaaaaggtt taatcttttg     300
taatttaaaa acccaaaaag ggattcaatt caacaccaaa agaagtccca tattaaatta     360
tctgattttt tttggtatta atttccattt tcttttttctc atctcccaaa ttgtaaaagc     420
tttgagcttt tgatttgata cccaaaagcc cgtccaaaag aaaaataaat aaaagttaag     480
aattaagcag aaaagagaga gaagtgcttt tctgagcttc ttttagcaaa aatgccatca     540
aacccatctc tcaaaatgca ggagaattga aacctcatct gctctyttt ttctcttctc     600 catattataa acaagcttaa gcagaagcag aagcaaaaag caaaaaagca aagtgctttt     660
ctccttcttc ttcctctttc gcttgttggg tccttacagt ttctgtttaa tttcacatgg     720
cgggtctaat tgatctgaac agtgcgacgg aggacgagga aacgccatcg tccggctcgc     780
cgtcttcggc ttcctctgtt tccgacgctc tgggttcgtc ggcgtcggtg tgcatggagc     840
tctggcacgc ctgcgcgggc ccactgattt cgctgccgaa gaagggagt gtggtggtgt     900 atctgccgca gggccacctg gagcaagtct tggattttcc gacctcggct tatgatctcc     960
cgccccacct cttctgtcgg gttgtcgatg tcaagctcca tgtcagtctc tctctataca    1020
atgagcctct ctttctccat gcttttgggg ttttggattt tgatgaaat ttgatagctt    1080 ttgggttttt gctatctggg ttctcaattt cttgaggtct ttttggtcg caggctgaga    1140 ctggcactga cgatgtcttc gctcrggttt cccttgttcc tgaaagtgag gtgggtttat    1200
ttgtacaagg tttgatttt tgtttggttc ctgagaaaat gctcgaaaag taaaaaaatt    1260
ctgagaaaat cctcccttc cgtagaaacc gaaacaatta aaaacgcaag ctttagaatt    1320
tcactttctt tctttcccac tttggcatta tcgaagatta tatgttagca tctctgtytc    1380
cttacaatta gtcatttcac aaatttatga attagttact tataatttat acaattcgat    1440
ttcggggttg rtgttttta attttctttg ctcttcctgg tgatcktgtg atgttttgt    1500
```

```
ctgttaaaca ttgacattga ggtgatttca ctaatgcttt aatcggtgta ggaaattgag    1560
cacagattgc gggaaggggt aaccgatgca gatgccgagg aggacgttga ggcaatgggg    1620
acgtcaacca caccccacat gttctgcaaa acccttactg cttctgatac tagcactcac    1680
ggaggcttct ctgtgcctcg tcgtgctgcc gaggattgct ttcctcccct ggtattccta    1740
gttcatgttc tcccccaact tttgktttag cttctgcata acttttttga gactaaatta    1800
ttagtctaat caagtacata ttagtatttt gttttgaga cgaatagatt gtgcttttag      1860
gattacactc aacaaaggcc ttcacaagag cttgtagcaa aggatctgca tggcctggag    1920
tggaggttcc ggcatatcta tagggtaat acaaaaaata tgatcccttt tgtgcttcat      1980
tagttggggg tttatctttc catgatacgg tagcaatctt attagagttt tataatgaac    2040
tttgtaaatt ggatgcttta gattcaacgt ttttctgttt cttattcctt ttttctaatt     2100
ggtttgagta gggcagccgc ggaggcattt gctcaccact gggtggagtg cgtttgtgaa    2160
caagaagaag ctcgtctctg gagatgcagt gctgtttctt aggtatataa acccttcgat    2220
tgaagagatt ttggatcccc wtatttataa ttctcatcca gtatttataa tagggtgac      2280 gatggagaac tgaggctagg aattagaagg gcagcccagt ttaaaagttc tgctacttgt    2340
ccaactcttt gtagccagca attgaactat agcactatca ctgatgtggt gaatgctata    2400
ttcgcgaaga atgcttttaa tgtgtactac aatccaaggt aatctggtgc tcatcattta    2460
acatgttcct aaagtaatgt tgaaagttat cgtgcttgag actttagacc tttcttcctt    2520
ctgcatcttt tttccttata atcgtccatg atcttgtagg tccagctctt ctgaattcat    2580
aataccttcc cataagtttt tgaggagcct tgatcattgt ttttgtgctg gaatgaggat    2640
caaaatgcgt tttgaaactg aagatgcagc agagcgaagg tttggcattc ttacttttga    2700
aatagttgaa gtagttttgt gcaaaatttt tattaaattt ttctttttgg cagatacact    2760
gggttgataa cggggattag tgaattggat cctgtaagat ggcctggttc aaaatggaga    2820
tgcctagttg tacgtatttt ctacacaaaa cttttatgta ctattttttc ccctttgttt    2880
gcacttataa gtatctgctt gagaaggttc gggtggtgaa tgccaatgta ctaaaccaaa    2940
agttatcttt agcgtaccat aaattctgta ttatcttctt tatgggagac ttactatacg    3000
tattggttat tttactttga gattcccaaa accattgtca tgaacaaatc tatgataagc    3060
ttttctcaac aatagttgaa gcatgagagt gcaaaaggta acaaaaaaaa tgtagccggc    3120
ttcaccgtat tctaactagg atgaattgca cacttcatat gtcatgtgaa atgtcacaat    3180
ttggtagaat ttctggctaa atttaaactg gaagcataaa ttttctcccg cattagctac    3240
acagttttat cttaattgtt gatcaagcca ccctactcat agtcctacgg agtagaaact    3300 cagggttat gagcaattat gtcttgatag tgagagttaa ttttcactgt cttgaaagtc      3360
gtttacctaa atatcataaa ctatgttttcc tctattctgt agcatgtcca tattgacttc    3420
cggtattcgc tcatgccatt agcactagat atataggttt gaacatttct tttgctattg    3480
caggtcaggt gggatgatrt agacacaagc aagcatggca gggtttcccc atgggaagtt    3540
gagcgatctg gttctgtttc tagttcccat accctaatga caactggctt gaagcggtcc    3600
aggattggct tgtctgcaac aaaaccagaa tktccagytc ctagtatgtc ctgcaatygt    3660
accacgacat gtcatcataa cactggtctc tgcaacataa ttgatttatt tgagtgtttc    3720
cttttcagat gggattggaa catcagactt tggggaatct ttaaggttcc agaaggtctt    3780
gcaaggtcaa gaaatttcgg ggtttgatac tcctttcagt ggtttaggtg gtctgaattc    3840
```

```
gcatccatct gaagcaagga gagtcttcca cggttccggt ggttctggga ttgctgctgg     3900
rggtaatggt ctcagacagt cacttgtgga ttctgagatt gcctcaaaag cataggctt      3960 tggtgaatca ttccgattcc ataaggtctt gcaaggtcaa gaaatatttc caagctcacc     4020
atatggaaga gctcccgctt ctaatgaagc tcatgaatat ggtggacctg gactctatga     4080
tggttttcag gtgcctggct ttaggaatgg atgstccacc atgatgcaga gcaataatac     4140
aaatgtgcac tcatctgccc catctgtgca agtttcatca ccttcgtctg tgttaatgtt     4200
ccagcaagca atgaatccag ttgcggaatt caactcggta tacaatggcc ataaccaaga     4260
ggaccataga gtaaatcgga ctccacatgt cttggaacat gatggtggaa ggcaaacatc     4320
atcctcattc ggtgaacgta acttcagcag ggaagatcgt ggaggcacac attcttacaa     4380
tcagcatggt atttcacctc atccagttat aagtcaatca acaattagtg gcagccagga     4440
ttctgtttca ccaatcaaag gtagctgtag actctttggt ttctcattgt ccgaggacaa     4500
atgtgtcccg gatcaagagg gcaaccccaa tgttggagtg cagtttcatt caaagcctcc     4560
tttgatgacc tcaacagttg gaataacctg tactaaagta agcaacctct ttgctgcatg     4620
aaatacaatt ttcaaatgtt acgactgggg tatttaatct tctatttgac ggaagcaaat     4680
gattatctga ttagcaagtg ggatgtttat gtctaggatt gggcttttga ctggcgcgga     4740
gaaaggatgg aaagctgttt acaaggatag tgatcatcct gtgcttgttg cagatgatcc     4800
gaggcagtaa ctagtaagtc ctcgtacgtt tacttattgt atttgyctat ttttgttctg     4860
tttgcaacct agcatcggaa tctacatggc attcttcatt gcccgtctat tgtcaaaact     4920
tacatatggt atgcctygaa gtccgcttat aaaccctacc catggaactc atcatggcca     4980
tgtttgtcgc cgcactatat ccttccaaag tcgtttttaag taaaccggat gaacatgaag     5040
aagatgcttg tgttccggtc atttatttgt ttgaatttcg cttttggcag gcgatgttac     5100
tgtaatatca atagttttgc gttgtaccga tgaagaaaac tctcgacagg cggaggtttt     5160
cttcgggatt atgtgtgtgc tgtcatttat gtaacttaat tttgaggcag aagttgtaac     5220
taagcgctcc aggggacttt gatttgtatt gttaattcag cttttgagaac aaaagtttgt     5280 agaatctata tttaatattg cttawccctc atatgtaamc ctgttgaaag agggcttgtc     5340
tgccaaggca caatmctccg atctataaca tttctttatt ttgaaattag tgtatccgag     5400
tctttgaccc gactaattac taaacccytg cctgcctgat tgcagaacat ttggggagcg     5460
agaraattta gcatttgcta ggtgggtatc gtgggagagt                           5500

<210> SEQ ID NO 16
<211> LENGTH: 2367
<212> TYPE: DNA
<213> ORGANISM: Arabidopsis thaliana

<400> SEQUENCE: 16
taatgtctct ctctccacgc acaaaaggtc taaaagccac accacacaca tcagtcacca      60
gacgtagcag agagcctcac tgttgcagag agcactcagt actgttctgt ttctctgata     120
cctctctctc tcctctctct tttaacattg tccaaattaa aaatctaaac ttttttttcta    180 gttttttttt tttctttaat agaaaagttt ttttctccca cggcttaaag actcactcat     240
cactgtgcta ctactctctc ttcttttggc tgagagggta aaagtcatga agaaactcct     300
ctgagttttt tttctttctt tcttataata aagctcttat ctttatctct gtttctctct     360
ctttaatggg tggtttaatc gatctgaacg tgatggagac ggaggaagac gaaacgcaaa     420
cgcaaacacc gtcttcagct tctgggtctg tctctcctac ttcgtcttct tcagcttctg     480
```

```
tgtctgtggt gtcttcgaat tctgctggtg gaggggtttg tttggagctg tggcatgctt    540
gtgctggacc ccttatctct ctaccaaaaa gaggaagcct tgtgttgtat ttccctcagg    600
gacatttgga acaagccccc gatttctccg ccgcgattta cgggctccct cctcacgtgt    660
tctgtcgtat tctcgatgtt aagcttcacg cagagacgac tacagatgaa gtttatgctc    720
aagtctctct tcttcctgag tcagaggaca ttgagaggaa ggtgcgtgaa ggaattatag    780
atgttgatgg tggagaggaa gattatgaag tgcttaagag gtctaatact cctcacatgt    840
tttgcaaaac ccttactgct tctgatacaa gcacccatgg tggtttctct gttcctcgcc    900
gagctgctga ggattgcttc cctcctctgg actatagcca gccccggcct tctcaggagc    960
ttcttgctag ggatcttcat ggcctggagt ggcgatttcg ccacatttat cgagggcaac   1020
ctaggaggca tttgctcact accgggtgga gtgcgtttgt gaacaagaag aagcttgtct   1080
ctggtgatgc tgtgcttttc cttagaggag atgatggcaa actgcgactg ggagttagaa   1140
gagcttctca aatcgaaggc accgctgctc tctcggctca atataatcag aatatgaacc   1200
acaacaattt ctctgaagta gctcatgcca tatcgaccca tagcgttttc agcatttcct   1260
acaaccccaa ggcaagctgg tcaaacttca taatccctgc accaaagttc ttgaaggttg   1320
ttgactatcc ctttttgcatt gggatgagat ttaaagcgag ggttgaatct gaagatgcat   1380
ctgagagaag atcccctggg attataagtg gtatcagcga cttggatcca atcaggtggc   1440
ctggttcaaa atggagatgc ctttggtaa ggtgggacga cattgtggca aatgggcatc   1500
aacagcgtgt ctcgccatgg gagatcgaac catctggttc catctccaat tcaggcagct   1560
tcgtaacaac tggtcccaag agaagcagga ttggcttttc ctcaggaaag cctgatatcc   1620
ctgtctctga ggggattcgc gccacagact tgaggaatc attgagattc cagagggtct   1680
tgcaaggtca agaaattttt ccgggtttta tcaacacttg ttcggatggt ggagccggtg   1740
ccaggagagg ccgcttcaaa ggaacagaat ttggtgactc ttatggtttc cataaggtct   1800
tgcaaggtca agaaacagtt cccgcctact caataaccga tcatcggcag cagcacgggt   1860
tgagccagag gaacatttgg tgtgggccgt tccagaactt tagtacacgt atcctccccc   1920
catctgtatc atcatcaccc tcttccgtct tgcttaccaa ctcgaacagt cctaacggac   1980
gtctggaaga ccatcacgga ggttcaggca gatgcaggct gtttggtttc ccattaaccg   2040
acgaaaccac agcagttgca tctgcgacgg ctgtcccctg cgttgaaggg aattccatga   2100
aaggtgcgtc agctgttcaa agcaatcatc atcattcgca aggaagggac atctatgcaa   2160
tgagagacat gttgctagac attgctctct agaagggttc tttggtttct gtgttttatt   2220
tgcttgtggc ttaagtaaag ttcttatttt agttgatgat gacttgctgc taacttttgg   2280
aatgtcacaa gttgtgactt atgagagact tgtaaacttg gttcaagaat gttctgtgtt   2340
aggttcaatt taaaaagtgt ttgcatc                                       2367
```

<210> SEQ ID NO 17
<211> LENGTH: 3710
<212> TYPE: DNA
<213> ORGANISM: Arabidopsis thaliana

<400> SEQUENCE: 17

```
taatgtctct ctctccacgc acaaaaggtc taaaagccac accacacaca tcagtcacca     60
gacgtagcag agagcctcac tgttgcagag agcactcagt actgttctgt ttctctgata    120
cctctctctc tcctctctct tttaacattg tccaaattaa aaatctaaac ttttttttcta   180
```

```
gtttttttttt tttctttaat agaaaagttt tttttctcca cggcttaaag actcactcat    240
cactgtgcta ctactctctc ttcttttggc tgagagggta aaagtcatga agaaactcct    300
ctgagttttt tttctttctt tcttataata aagctcttat ctttatctct gtttctctct    360
ctttaatggg tggtttaatc gatctgaacg tgatggagac ggaggaagac gaaacgcaaa    420
cgcaaacacc gtcttcagct tctgggtctg tctctcctac ttcgtcttct tcagcttctg    480
tgtctgtggt gtcttcgaat tctgctggtg gaggggtttg tttggagctg tggcatgctt    540
gtgctggacc ccttatctct ctaccaaaaa gaggaagcct tgtgttgtat ttccctcagg    600
gacatttgga acaagccccc gattctccg ccgcgattta cgggctccct cctcacgtgt    660
tctgtcgtat tctcgatgtt aagcttcacg tatgtaacta actctctctt tctttctatt    720
ttttgttttg ttttgttttc ttcatttatg ttttctcctc tgctctcaaa gcagagagat    780
atgggttttg ttctgttttt ctgattcttt gattttttta attgtttgtt tggtgaatct    840
gagttgggtt ttcgatacaa gtatggagat ttgtgccttt ggtttattga attgtttgag    900
acaaacgaat ttatgttggg agaaaagttt cctcttttgc tccatttgca tttcttctcg    960
tggcattttg atgacgaata cttgaaatcc ccataaatta tcttcagttt tttctttgat   1020
gataatgaat ttgatttcaa agtttcgcct tttgctccat tttgatgaca attgatttca   1080
gaacaattca attctctgta aaggtttaaa cttttttttgt tgttgtgagg attaataaac   1140
aaaatgtggg ggattttgat ttcgtaggca gagacgacta cagatgaagt ttatgctcaa   1200
gtctctcttc ttcctgagtc agaggtgagt ttttctttag gctcttgagt tttgtaacaa   1260
agagagagaa atttgctcga gcttaggggg tttgagttga tttgttacag gacattgaga   1320
ggaaggtgcg tgaaggaatt atagatgttg atggtggaga ggaagattat gaagtgctta   1380
agaggtctaa tactcctcac atgttttgca aaacccttac tgcttctgat acaagcaccc   1440
atggtggttt ctctgttcct cgccgagctg ctgaggattg cttccctcct ctggtactaa   1500
tccactctct gtagattctg taatcagctt tgtacattgc acattgtgtt ctagagttct   1560
cttattagct catattgaga gattttaact acataatcat tttgttatgt aggactatag   1620
ccagccccgg ccttctcagg agcttcttgc tagggatctt catggcctgg agtggcgatt   1680
tcgccacatt tatcgaggta agtttgttgc cttatgttgc aattttttctt gcctggattt   1740 agtagatgga aaatttgaat ggtttgagtg acttttaggg caacctagga ggcatttgct   1800
cactaccggg tggagtgcgt tgtgaacaa gaagaagctt gtctctggtg atgctgtgct   1860
tttccttagg tagttaaaaa tgcttctatg ttttctcact acacaacctc tttgattttc   1920
tgtaagaggt tttgtgatat atgggtttct ctgatacaga ggagatgatg gcaaactgcg   1980
actgggagtt agaagagctt ctcaaatcga aggcaccgct gctctctcgg ctcaatataa   2040
tcagaatatg aaccacaaca atttctctga agtagctcat gccatatcga cccatagcgt   2100
tttcagcatt tcctacaacc ccaagtaagc cccaaccaca atgaccttttt tcgttttca   2160 gcatttaaaa tttcatttca gaatcataat tagaatctcc tgaagcctta agttgtgtat   2220
tgttctagtt gattgttcct tagaagtttg ttaactccaa taaatatcag gaatttagca   2280
ttaatactag ttcactggta aaacattttc agggcaagct ggtcaaactt cataatccct   2340
gcaccaaagt tcttgaaggt tgttgactat cccttttgca ttgggatgag atttaaagcg   2400
agggttgaat ctgaagatgc atctgagaga aggttactta tagacttata attcaagctt   2460
taagataacc ttgcacacct gtgttttata tgcccaactt tctaacatgt ttcacctgtt   2520
ttgtcagatc ccctgggatt ataagtggta tcagcgactt ggatccaatc aggtggcctg   2580
```

```
gttcaaaatg gagatgcctt ttggtaagct atgaattatg ttcttaagtc attagtttgg    2640
tctgagaggt cttctataag attgttgcct tttctatatc cgtaagctca ctgctctgaa    2700
actatgtttt gacgtcatat tcaggtaagg tgggacgaca ttgtggcaaa tgggcatcaa    2760
cagcgtgtct cgccatggga gatcgaacca tctggttcca tctccaattc aggcagcttc    2820
gtaacaactg gtcccaagag aagcaggatt ggcttttcct caggaaagcc tgatatccct    2880
gtctctggta cacatctact tagccaaaga cattgtacca ctcatataac catttatcgc    2940
ctgtaatata acgttttctg ctattattgc agaggggatt cgcgccacag actttgagga    3000
atcattgaga ttccagaggg tcttgcaagg tcaagaaatt tttccgggtt ttatcaacac    3060
ttgttcggat ggtggagccg gtgccaggag aggccgcttc aaaggaacag aatttggtga    3120
ctcttatggt ttccataagg tcttgcaagg tcaagaaaca gttcccgcct actcaataac    3180
cgatcatcgg cagcagcacg ggttgagcca gaggaacatt tggtgtgggc cgttccagaa    3240
ctttagtaca cgtatcctcc ccccatctgt atcatcatca ccctcttccg tcttgcttac    3300
caactcgaac agtcctaacg gacgtctgga agaccatcac ggaggttcag gcagatgcag    3360
gctgtttggt ttcccattaa ccgacgaaac cacagcagtt gcatctgcga cggctgtccc    3420
ctgcgttgaa gggaattcca tgaaaggtgc gtcagctgtt caaagcaatc atcatcattc    3480
gcaaggaagg gacatctatg caatgagaga catgttgcta gacattgctc tctagaaggg    3540
ttctttggtt tctgtgtttt atttgcttgt ggcttaagta aagttcttat tttagttgat    3600
gatgacttgc tgctaacttt tggaatgtca caagttgtga cttatgagag acttgtaaac    3660
ttggttcaag aatgttctgt gttaggttca atttaaaaag tgtttgcatc             3710

<210> SEQ ID NO 18
<211> LENGTH: 2935
<212> TYPE: DNA
<213> ORGANISM: Phaseolus vulgaris

<400> SEQUENCE: 18
ccatgataaa ataacatttt gcttgtgaaa tgttactggt tgttttggtt acatccaact      60
tcattgatgg tgtcagtgtt ctgtaagtga gaaaattgaa ttttggagtg gtttggttaa     120
gagagatggt taaatgtgga ggataacggt agagtgagtt ggtaagagag tgggaatgaa     180
agggtttccc aaaaagcgaa ccccataatt gtgtgaggag tgaagagccc aaaaagggtg     240
ggaaaaatga agagagagtg attggtcagt gggagagaaa gacagagaca gagaaagcgg     300
gtctctttct ttttggagta ttgggtcagg ttcttttggc aatgccaaag ttggtcacgc     360
tctctgaaaa tgcaggaggc atgaaaccac tccttcaaat atctcccacc actcactcgc     420
tcctgtgctg cttcttcttc tccttctgtt tctgttcctt ctctctctat ctccctcttt     480
tctcctcctc ctcctcatgc ctgccctcat cgatctcaac agcgccaccg aggaccatga     540
aacgccgtcg tctcgcccat cctccgtctg cctcgaactc tggcacgcct gcgcgggtcc     600
tatgatctcc ttgcccaaga aagggaccct tgtcgtgtac ttccctcaag acacttgga     660 acaacacctt cacgattttc cgctcccctgc ttctgctaac atcccctccc atctcttctg     720
tcgcgttctc gatgtcaagc tccattctga ggaagggagc gatgaggtgt attgccaggt     780
ggtgctggtt cccgaaagtg agcaagggca tcagaagttg cgggaagggg aaattgatgc     840
tgatggtgaa gaggaggatg ctgaagctgt gatgaagtcc accacacccc acatgttctg     900
caagactttg acagcttctg atactagcac tcatggcgga ttctctgtgc ctcgtcgtgc     960
```

-continued

```
tgcggaagat tgttttccac ctctggatta cagtcaacag agaccttcac aggagcttgt      1020
ggcgaaggat ctgcatggcc aagaatggag gttccgacat atttataggg ggcaaccacg      1080
acgacacttg cttaccactg ggtggagtgc atttgtgaac aagaagaaac ttgtatctag      1140
agatgctgtt ctgtttctta ggggtgagga tggagaactg agattgggaa ttcgtagggc      1200
tgctcaattg aaaagtggca gtaccatttc aacttttgct ggccagcaat tgaatcatag      1260
cagtcttctg gatgtggtta atgctttatc agcaagatgt gcctttagtg ttcactataa      1320
tccaagggtc agttcatctg agttcatcat acccattaag aaattcttga ggagccttga      1380
ttattcttat tcagttggaa caagatttag gatgcgtttt gaaactgaag atgctgcaga      1440
gcgaagattt acaggattga ttgttggaat tactgatgtg gatcctgtta gatggcctgg      1500
atcaaaatgg agatgcctaa tggtaaggtg ggatgacctg gaagccacaa ggcataatag      1560
ggtttcaccc tgggagattg agccatctgg ttctgcatct actgcaaata acatgatatc      1620
agctggtttg aagaggacca agattggatt gccttcaacc aagctagatt ttcaagtttc      1680
caatgcaatt ggagcatcag actttggcga atcactaagg ttccagaagg tcttgcaagg      1740
tcaagaaatg ttgggtgtta acacaacttt tgatagtact aatggtcagg gtcaccagct      1800
atcagatttg aggagatgct atcctggctc aaactgttct aggattgctg caaccggaaa      1860
cagcattgga attccgcaag tgagttccaa tgtttcctgc aatggcatag gcttcagtga      1920
atctttcaga ttccagaagg tcttgcaagg tcaagaaata cttccaagcc aaccatatgg      1980
aagggccctg tctgttgatg aggcttgtgg aaatggtcgc tttggacctt tgatggtta       2040 ccatacactg agatccagaa atggatggtc ttcccacttg agtaacagtt cttcacattt      2100
gcatccacct gttccatctg ggcaagtttc atctccatca tctgtgttaa tgttccagca      2160
agcacacaat ccagtttcaa actctgatta caacagcaaa attagtcagg tgatggaagg      2220
taaagtccag caacgatcat catacacttc tgaagctaaa ggtggaaaat tgtatcaac       2280 cccttatgag cctcttcgtg gactagctca ggaaggcaca aattcttatg gggtctcaaa      2340
cttgcacaat cagtttgaaa cttcacgttc acacgattct atttcagcac ttcgggctac      2400
tcaagagttg gttcccacat gtaaaagtcg atgcagagtc tttggcttct cattaactga      2460
gggtgctcct gttgcaagta aagaagtagc cggcaccgac ccatcggccg tcacatgttc      2520
tggaccttcc tttgcaagac acgctgaaga tgatttccat ccagtgcata gcaaggcagt      2580
gggaagttat tgcaccaaag gtgtgctgca atattgactt gaaaatcatg gtgtatggta      2640
gtagttatgc tgtcataagg tggcagaaga gaatgttcac tgttgtacta atgtggagaa      2700
tatgataact attcgcctaa ctagatattt atcttgttaa attggctgtg acacaatcaa      2760
tttctgtatt aatctatgta ctctttattg acttgtaaaa cgatgcatgt gtgttcactg      2820
ttatggccat atgaggctct ggtggcactg cataacccctt catttatctt gaattgggca      2880
tgattacttt agggaactat agctcatcat gtttcatgac cttaagttat ctcca           2935
```

<210> SEQ ID NO 19
<211> LENGTH: 2762
<212> TYPE: DNA
<213> ORGANISM: Lycopersicum esculentum

<400> SEQUENCE: 19

```
aattcgccct tgagtgcgca gttgaactag caaaagggtt taaagatgat gtgtggactt        60
attgatctga atactgtgga taacgatgat gccggagaag aaacgacggc gccggtgtca       120
ttggattcac cggcgtcgtc gtcggcggca tcaggaagtt cggatttaac gtcgtcaact       180
```

```
acgccagcgg tggcatcggt gtgtatggag ctttggcatg cgtgtgctgg accgttgatt    240
tcgctgccga agaaaggaag tgcggttgtg tacctgcctc aaggtcactt ggaacattta    300
tctgagtacc cgtccatagc ctgtaatctc cctcctcatg tgttttgtcg cgttgtagat    360
gtgaagctac aagcagatgc ggctactgat gaggtctatg cacaagtctc actagttcct    420
gacaatcagc agattgagca gaaatggaag gatggagaca ttgatgctga tattgaagaa    480
gaggaaatag aaggtgctgg aaaatcaata acaccacaca tgttctgcaa aactcttact    540
gcatcggata ccagcactca tggtggtttc tctgtccctc ggcgggcagc agaagattgt    600
tttgctccct tggattacag acaacagagg ccctcgcagg agctggtagc aaagatcta    660 catggtatag agtggaaatt tcggcatatc tatcggggtc agccacggcg gcatctgctc    720
actacaggat ggagtgcatt tgtaaacaag aagaagcttg tttctggtga cgctgttctt    780
ttcttgagga ctggtgatgg agagcttagg ttaggagtga gacgagctgc ccaagcaaaa    840
acatgttcta gttatctggc tccttgtagc aaaccgttga atgttagtgg cattgtagat    900
gctgttaacg ttatatctag cagaaatgct ttcaacattt gttacaaccc aagggatagc    960
tcatcggatt tcattgtacc ttaccacaaa ttctctaaga ctcttgcaca tcccttttca   1020
gctggaatga ggtttaaaat gcgtgtcgaa acagaagatg cagctgagca aggttcact   1080 ggactagttg tgggagtcag caatgtagat ccagttcgat ggccaggttc taatggagg   1140 tgcctattgg tcagatggga tgatcttgat gtttctagac ataatagggt ttcaccatgg   1200
gagattgagc catctggttc agctcctgtg cccagcagct tggtgatgcc ttctgctaag   1260
aggaccaggg ttggcttccc tatttcaaag gcagattttc caattcctag agaaggaatt   1320
gcagtatcag actttgggga accttctagg ttccagaagg tcttgcaagg tcaagaaatt   1380
ttgaggatgc atgctcctta tggcggactt gatgctcgga gtcctcgtcc agcaggcaca   1440
agatgctttc ctggttttcc tagttctggg atatctagaa tgggaaacag catcagaccc   1500
ctgtttggtg acactgacaa gtcccatgaa agcattggct ttagtgaatc tcttcgattc   1560
aataaggtct tgcaaggtca agaaattttt acaagccctc cttatgggag agctcaagct   1620
ggtatccaaa tgcaggagaa aagtaggacc ggtatttttg tcggtattca ggttccaaac   1680
catggaaaca ggtggcctgc tccaaatcag gataataaca ctccttgcaa gccaattaat   1740
cctgtctcag catcatcacc gccttctgca ctcaattttc agcatccgag ccctccagca   1800
tcaaagttcc aggctatgtt caatcataaa catgatcttg ttaaccaggc ttcgttagat   1860
ctgtctgaga actgttgtag gtatccgtat ctctcatctg gttcacatac cgaggacatc   1920
agtcagaagg aagtactcag aggaatcagc tcgtttggtt tcttaaagga gcaaaagcaa   1980
acaggacttt catatctttc tcctgggaca cagtcgtcat tcaaaggcaa tcaaaactta   2040
gtttccactt gtaaaactgg ttgcaggatc tttgggttcc ccttgaccga gagtaaaata   2100
agtgcaacta gagcggatac tccctctgaa gctgtatact cacatggtct agaaactaca   2160 tttctcccctt ccagtgatgg aaagttgcag ccggggccac cattgatgac taacgttgtg   2220
gggacaaatt ttaccaaagt aaatgacctc tatgcagcaa gagatgtgct tcttgatatt   2280
gctctgtagc aggtgtttgt tgtgagggtt gctagaata tgtagactga aggatgtgtg   2340
tgcagcatta ttgattatta gcttttagtt ggcgttgtaa tcttctggct gttgagtgcg   2400
caagcatttg gttgccagta gaatgcttat ccagagatga gaattgagag ttattaatga   2460
agattgatac cgttgaggaa cgtatgttct tgaaaatttg gtgtatatgt tcctgtgacg   2520
```

| | |
|---|---|
| ctgatgtact atgtaacaat tggaagctgt gtttgctgca tcaaagatgt ctgtatgata | 2580 |
| gttgtactct acttgagatg acttctgtat ttgtatattt acctagtcta gatttgctgt | 2640 |
| gaactaactc gagctcctat aaatcggtaa gtttgttgta ggagctctcg tctcaggaac | 2700 |
| acaatactgt actgaatttt gtaaggaatt gtcatgtata ttcctgcaat taagggcgaa | 2760 |
| tt | 2762 |

<210> SEQ ID NO 20
<211> LENGTH: 2622
<212> TYPE: DNA
<213> ORGANISM: Citrus clementina

<400> SEQUENCE: 20

| | |
|---|---|
| ttgacgaagt tgcagcagcc agcagcactt aaaacacttg cctctaaaat gcagtcatga | 60 |
| aactctctct ccttctcgct ctcaaaagca cttgttttc acaactttt cttctcagct | 120 |
| tccactacaa caccattgta tcgttctaag catctctcta aaatggtggg tttgattgat | 180 |
| cttaacacaa cagaagacga tgagaatccg tcatcgggat ctttatctcc gtcctcttct | 240 |
| tctgcttctg ccttgagtgc ttctggtttc gctttagctc ctgcttctgc ttctgcttct | 300 |
| ggggtgtctt tagagctatg gcacgcatgt gcagggccac taatatctct gcccaagaga | 360 |
| ggcagtgtgg tcgtttactt ccctcaggga catttggagc atgtctccga ttttccgcc | 420 |
| gctgcttcag ctgcttatga tctcccccct catctgtttt gtcgggttgc tgatgtcaag | 480 |
| ctccatgcag aggcggcaag tgatgaggtt tatgcgcagg tctcactggt tccagatgag | 540 |
| ctaattgagc agaaggtgcg tgaagggaaa attgaggagg atggtgatga ggagagtgtt | 600 |
| gaggtggttg ctaagtcttc aacaccccac atgttctgca agaccctcac ggcttctgat | 660 |
| actagcactc atggaggctt ctctgtacct cgtcgagctg cagaagactg cttccctccc | 720 |
| ctggactata gtcaacagag gccttcacag gagcttgtgg caaaggatct ccatggcctg | 780 |
| gaatggaggt tccggcacat ttacaggggg caaccacgga ggcatttgct gactactgga | 840 |
| tggagtgcat ttgttaataa gaagaagctt gtttctggag atgctgtgct tttccttagg | 900 |
| ggtgaagatg tgaattgag acttggaatc cgaagagcac ctcatgtaaa agtggtgct | 960 |
| actttcccctt cttctgcag ccaacagtcg agtcccaatt ctgtcacaga ggtggttgat | 1020 |
| gccatagcta ggaagcgtgc tttcagcatt tcctacaatc aagggccag cgcctcagag | 1080 |
| ttcataattc ctgtcaataa gttttgaag agccttggtc attctttcgc tgttggaatg | 1140 |
| aggttcaaaa tgcgtttga aacagaagat gcagcagagc gaagatacac tggagtgatt | 1200 |
| atgggagtcg gtgacatgga tcctgtgaga tggcctggtt caaaatggag atgcctgttg | 1260 |
| gtgagatggg atgatgttga gtccaacagg cacaccaggg tatctccatg ggaaattgag | 1320 |
| ccatctggtt ctgtttgtgg ttccaataac ctgatcacat ctggtttgaa gaggaccagg | 1380 |
| attggattgc cttctgggaa accagaattt ccagttcctg atggaattgg agtgacagac | 1440 |
| tttgggggaat ctttgaggtt ccagaaggtc ttgcaaggtc aagaaatatt aggttttaac | 1500 |
| actctttatg atggtggtga ttgtcagaat ctgcatccat ctgaagtaag gaggggcatt | 1560 |
| cctggttcaa atggttctgg gattgctgct ataggagatg gtagcagaaa cctgcaggtg | 1620 |
| aaatctgaca tttcctacaa aggcataggc ataggctttg gtgaatcatt ccgattccat | 1680 |
| aaggtcttgc aaggtcaaga aatatttccg aagtctccat atggaagagc ccctactaat | 1740 |
| aatgaggctc gtagtattgg cagccttgga atctctgatg tgttccggt atctggatca | 1800 |
| agaaatagat ggtctgctgt ggtgccgggc tataacactc atatgagccc atctgcaccg | 1860 |

```
cctgtacaag tgtcatcacc ttcttcggtg ttaatgtttc agctggcaag caatccaatt    1920
tctaactata atcctcctta tagcttgaac gatcaggaga agagcaacg tgtcaactgt     1980 caaagctttt ttcataattc tgaaatatat ggaggaaagc atgcatcatc ttcatttctt    2040
gaccatagtt tcgtgggggg tgatcaggag gtcatggatt ctataggtca gtcaaatgag    2100
catatttcac cacctcttgt aggtcagcca acagttaggg gcagccaaga tttagtttcc    2160
tcgtgtaagg gtagctgcag actctttggt ttttcattga ctgaggaaag acatgttgcc    2220
aacatagagg acaatgcagc tccagttgcg tctcctttga atcctagatc ttcttttctg    2280
tctcatgttg gacagcagtt ccatccaaag cctccagtaa tgtctaaggc aactggaagc    2340
aactgtacca atggaatcat gcaacattgt cttggaaatt atgatatata ctaaccaagg    2400
tgcagaggta gcacctgggc ttgcagaaga aaatgcttgt aattgctcta attatacata    2460
tgctgtagta aatgatacaa tttaattagc tggtgagaaa accaagtgta agtattttt    2520 tcaaagtaac ttgatgtcat gattatgctt aactccacta tggaaagcaa acaacatatg    2580
tattgtatta atctattaag tttccagcgg atgttgtcta tt                      2622
```

<210> SEQ ID NO 21
<211> LENGTH: 2917
<212> TYPE: DNA
<213> ORGANISM: Fragaria vesca

<400> SEQUENCE: 21

```
ctttcactgt ctttctctgc cacacatcac acccagcagt tgcagcgttg cagaggctgc     60
agcactgcag cagagctgca gagagagaca gactcaaaga aataatataa aaattcgcaa    120
ggaaaaagat aaaagagaaa gaattcttta aaaaaaacaa attttaagt cttttgagta    180 ttctattggg ttgggtttgg gtctgtcaaa gttttaaga ttaaagctct gagcttttta     240
ttcacataca ccaaaaaaga gtgtgtcttg gtttcttttg ggtgtgtttc ttttagcaaa    300
tgccttaaaa atgcacaagt gaaaccagtt gggttgtagt ttgagctttg acacataaaa    360
aggcttgagc tttagctttg tctgttgtgt tgtttagagt tttgggttat ggcgggtctg    420
atcgatctga acagcacgac ggaggaggag gaggagacgc cgtcatctgg gtcgtcgtcc    480
aattcgtctg gctcaaatgg tttgattttct gggtctgttt gcttggagct gtggcacgcc    540
tgtgctgggc cactgatttc tttgcccaag aaaggtagtg tggtggttta tcttccacaa    600
gggcacttgg agcaagtgag tgattttcca gcctcggttt atgatctccc tgctcatctg    660
ttttgccgag ttctggatgt taagcttcat gcggagagtg gtagtgatga agtgtacgca    720
caggttcagt tggttcctga aagtgaggaa tttgagcaca aactagggga aagagaaact    780
gttgcagatg gggacgagga tgctgagggt tcagagaaat caactacacc ccatatgttc    840
tgcaaaaccc ttactgcttc tgatactagc actcatgggg gcttctctgt ccctcgccgt    900
gctgctgagg attgttttcc tcccctggat tacagtcaac aaaggccttc acaggagcta    960
gtggcaaagg atctgcatgg cctggaatgg aggttcagac atatctatag ggggcagcca   1020
cgcaggcatt tgcttaccac tggatggagt gcctttgtga acaagaagaa gctcgtttct   1080
ggagatgctg tgttgtttct caggggtgag atggagaac tgagacttgg agttagaagg    1140
gcagcccaag taaaagcttc tgccacttat ccaactcctg gtagccagca tttaaactat   1200
aactctgtca cagagctggt ggatgctata tctacgaaga ctgcttttaa cgcctattac   1260
aatccaagag ccagctcatc agaatttata ataccttttcc gtaagttttt gaggagcctt   1320
```

```
ggtcattcct tctgtgctgg aatgagattt aaaatgcgct ttgaaacaga agacgccgca    1380
gagcaaagat acactggact ggtaacgggg attagtgagt tggatcccct aagatggcct    1440
ggttccaagt ggaaatgtgt agctgtacgg tgggatgata tagatactag caagcagcat    1500
ggccgggttt ccccatggga aattgagcca tctggttcta tttctaattc cagtggctta    1560
atggcatctg gtctgaagag gtccaggatg ggcttatctg cagaaaagca agaatttcca    1620
gttcctcatg ggattggagc ctcagacttt ggggaatctt taagattcca gaaggtcttg    1680
caaggtcaag aagtttcggg ttttgatact cctttggtt ctataggggg tcaaaatcag    1740
catccctctg aatcgaggag agtctttcac ggctctattg gttctagagg taatgatctc    1800
agaaactcat ttgtgaattc tgagattgcc tcaaaaggct ttggtgaatc tttccgattc    1860
cagaaggtct tgcaaggtca agaaatattt ccaagcacac catacggaag agctccagct    1920
actaatgagg ctcgtgaata tggttgccct ggaatctttg atggttttca ggtgccaagc    1980
tttagaaatg gatggtctac gatgatgcag ggcagtaata cacctatgca ccgagctgcc    2040
cctgtacagg tgtcatcacc atcatctgtg ctgatgttcc agcaagcaat aaatgcagga    2100
gccgagttca attcagtata caatggtcat aaccaacagg aacagagaat aatgcaacgc    2160
actcattctg aatcagatgg tgggaagcaa acatcagcct cgttctgtga acgaagcttc    2220
accagggagg gtcatggtgg catgaattct tttgatcaac atggtatttc acatcctcct    2280
cttttgagtc agtcttcatt gagaggcagt caagatatgg tttcatcatg caaagtagc    2340 tgcagactgt ttggtttctc actgtctgag gaaacacatg ccccaaataa agtggacaac    2400
tccacctcag ttcatctgc attagagtct ggagcttcta tgttcccaa tgttgaacca    2460 cggtttcatt caaagccgcc ttcgatgtct gcagctgttg ggattccttg taccaaagaa    2520
tgggcattta actggcgtgg agaaaggatg gaaagttgtt tacaaggata gtgacaacga    2580
cacagagctt gttgtgacgt tccacccaga aatgctacca caatattatg taagaaacac    2640
taggctagaa gatgtagtct ttgcgcccga ggattttcgc aggttatgcg tgtgttgtat    2700
tttatgtaac tgaactacat ttgaaggtaa aaaaaaagaa aaaagaaga aggtttgatt    2760 aagcgcttct gggtgacttg attgtattat gatgaattaa gctgtaagaa acggtttgca    2820
gaatctatga ttgcctcttg aaaaagggc ctatccgaaa ctgaacaaat tgtaccgatt    2880
tgcaattgtt aaataatgtt attacttatc gtcccta                            2917
```

<210> SEQ ID NO 22
<211> LENGTH: 2215
<212> TYPE: DNA
<213> ORGANISM: Prunus persica

<400> SEQUENCE: 22

```
atgggggtc taatcgatct gaacagtgca acggaggacg aggaaacgcc gtcgtctggt       60
tcgtcttcaa cttcctctgc ttctgacgct tcggcttcgg cttcggcttc ggtgtgcttg     120
gagctgtggc acgcgtgtgc gggcccactg atttcgctgc caagaaagg gagtgtggta     180 gtgtatcttc cacagggcca cttggagcaa gtctctgatt ttccagcttc ggcttataat     240
ctcccacctc accttttctg tcgcgttgtt gatgtcaagc tccatgctga gactggtacc     300
gacgatgtgt atgcgcaggt ttcacttgtt cctgaaagtg aggaaattga acacaaactg     360
cgggaagggg aaactgatgc atatggtgag gaggaggatg tcgaagcaat tgggaagtca     420
accacacccc atatgttctg caaaacccctt actgcttctg atactagcac tcatggaggc     480
ttctccgtcc ctcgtcgtgc tgctgaggat tgttttcctc ccctggatta caatcaacaa     540
```

```
aggccttcac aagaactcgt agcaaaggat ctgcatggcc tggagtggag gttcagacat      600
atttataggg ggcagccacg aaggcatttg ctcaccactg gatggagtgc atttgtgaac      660
aagaagaagc tcgtctctgg agatgcagtg ctgtttctca ggggtgatga tggagaactg      720
aggctaggaa ttagaagggc agcccaggtt aaagggtccg ctacttatcc aactctttgt      780
agccagcaat taaactataa cactatcacg gacgtggtga atgctatatc catgaagaat      840
gcatttaaca tcttctacaa tccaagagcc agctcatcag aattcataat accttcccgt      900 aaattttga ggtcccttga tcattccttt tcacctggaa tgcggttcaa aatgcgtttt       960
gaaacagaag atgcagcaga gcgaagatac actgggctga taactggaat tagtgaattg     1020
gatcctgtaa gatggcctgg ttcaaaatgg agatgtctag ttgtaaggtg ggatgatata     1080
gacacaagta agcatggcag ggtttcccca tgggaaatcg agccatctgg ttctgtttca     1140
agttcccata gcttaatggc agctggtttg aagagggcca ggagtggctt gtctgcagca     1200
aaaacagaat ttccagttcc taatgggatt ggagcatcag actttgggga atctttaagg     1260
ttccagaagg tcttgcaagg tcaagaaatt ttaggttttg atactcattt tggtggttta     1320
ggtggtcaga atcaacatcc atctgaacca aggaggggtt ttcatggttc tagtggttct     1380
gggattgctg ctggaggtaa tggtctcaga aagtcacttg cgcactctga gattacctca     1440
accggcatag gctttggtga atcattccga ttccataagg tcttgcaagg tcaagaaata     1500
tttccaagcc caccatatgg aagagcttcc actaataacg aggctcatga atatggtggc     1560
cctggaattt atgatggttt tcaggtgcca agctttagaa tgggtggcc tgccatgatg      1620 cagagcaata atgcacacgt gcgcccatct gcctcgtctg tgcaagtttc atcaccatcg     1680
tctgtgttaa tgttccagca agcaatgaat ccaggcccgg aattcaattc agtatacaat     1740
ggtcataacc aggaggaaca gagagttata aaacggactc catatgtctc tgaatcagat     1800
ggcggaaagc aagcatcatc ctcatttttgt gaacgtagct tcagcaggga agatcatgga     1860
ggcatgaatt cttacaatca acatggtatc tcaaatcatc ctgtaataag tcaatcaaca     1920
tttagtggca gtcaggatgc ggtttcacca tacaaaggca gctgtagact ctttggtttc     1980
tcattgtctg aggaaaaacg tgtcccagac agagagagca actccacctc aactgcatct     2040
acattaaatc ctggagtgca gttcattcaa aagcctgcat tgatgacatc agcagttgga     2100
attacctgta ccaaagaatg ggcttttgac tggcgtggag aaaggatgga aagctgttta     2160
caaggatagc gatgatacaa tggcttgttg cagaagatca aaggcagggt cttaa           2215
```

<210> SEQ ID NO 23
<211> LENGTH: 669
<212> TYPE: DNA
<213> ORGANISM: Pyrus communis

<400> SEQUENCE: 23

```
attgcctcaa aaggcatagg ctttggtgaa tcactccgat tccataaggt cttgcaaggt       60
caagaaatat ttccaagctc accatatgga agagctccca cttctaacaa agctcatgaa      120
tatggtggac ctggagtcta tgatggtttt caggtgcccg gctttagaaa tggatggtcc      180
accatgatgc agagcaataa tacacatgtg cacccatctg ccacatctgt gcaagtttca      240
tcaccatcgt ctgtgttaat gttccagcaa gcaatcaacc cagttatgga attcaattcg      300
gtatacaatg gtcataacca agaggaacat acagttataa atcgaactcc atatgtctct     360
gaatatgacg gtggaaggca acatcatccc tcatttggtg aacgtaactt cagcagggaa     420
```

-continued

```
gataatggtg gcacgcattc ttacagtatt tcaaacgatc cagttataag tcgatcaaca      480
tttagtggca gtcaggattc agtttcacca accaaaggta gctgtagact ctttggtttc      540
tcattgtctg aggacaaatg tgtcccggat caagccccta ctgctggagt gcggtttcat      600
tcaaagcctc ctttgatgac ttcagcagtt ggaattacct gtactaaagt aagcaacctc      660
tttgctgca                                                              669
```

<210> SEQ ID NO 24
<211> LENGTH: 3045
<212> TYPE: DNA
<213> ORGANISM: Populus tremula

<400> SEQUENCE: 24

```
atggaaagga agaagcactt gaaaaagaaa agataagaga gacagatata gttcccatta       60
atatctcttt ttctgtctct ctctctaaca ctactgccac acatcgcatc cttgcagggt      120
cttcacagca tggcagcatt gcggcaggca ctgcatctca gttttgcaga tcatgagcaa      180
ggaaagaaac ccatgaaaaa ttgagaagaa ataaataaa aagttgaaag ctttaattta      240
atttaattta atactagtac cctttaaagc ctttgatttg atatcttaaa aaagcagaga      300
gagacaaagg gtctctcttt ttaagagtct tgactctaat ctccttttag caattgccaa      360
aagttgcact ataatgcagt catgaaatct ctcctcgctc acaaaagcac ttgtctttta      420
ataaaccttc attattgtta tcaacagtta ctccttgtta ttcttcaaga actctacact      480
gttcctgttg ttactgcctt tgtttaggaa aggctataga gctgatcaag ctaaaaatg      540 gtgggtatga tagatctcaa cactattgaa gaagatgaaa ctacaccgtc ttgtgggtct      600
ttatcttctc catcatcatc ctctgctgct tctgctttga gtgcttctgg ctctggttct      660
agtacctctt ctgtttgttt ggagctttgg catgcttgtg ctggcccact aatatctttg      720
ccaaagagag ggagtgttgt tgtgtatttc cctcaaggcc acttggaaca actccctgat      780
ttgcctcttg cagtttatga tctcccttct catgtcttct gtcgagttgt tgatgtcaag      840
ctccatgccg aggcagcaag tgatgaggtg tatgcacagg tctccctggt tcctgagagt      900
gaggaaattg agcagaagtt gagggagggg atatttgagg gggatggtga ggaggaggat      960
ggtgaagcca ctgtgaagat gacaacaccc catatgttct gtaagaccct aactgcttct     1020
gacactagca ctcatggagg cttttcagtc cctcgtcgag ctgctgagga ctgcttccct     1080
cctctggatt atactcaaca aaggccttca caagagcttg tggcaaagga tcttcatggc     1140
tctgagtgga gtttcgaca tatctacagg ggtcagccac ggaggcattt gctcactact     1200
ggatggagtg cgtttgtcaa taagaaaaaa cttgtctctg gggatgccgt tctctttctc     1260 agggtgagg atggggaatt gagactggga gttcgaagag cagcacaagt taaatgtggc     1320
cctacatttc cagctcaatg gaatcatcag ctgaatcaga tctctcctgg ggatgtagct     1380
aatgctattt ctactagaag tttttttccac atttactaca atccaagggc cagctcatca     1440
gagttcataa taccttttaa taaattcttg aagagccttg atcaatcctt ctcttctgga     1500
atgagattca aaatgcgttt tgaaacagaa gatgcagcag agagaagata cactggaata     1560
ataactggag tcagtgagct agatcctgct agatggcctg gttcaaaatg gaaatgcctg     1620
ttggtaaggt gggatgatat ggaggctaac aggctcagca gggtttctcc ttgggaagtt     1680
gagccttctg gttctggttc ttttttccagt tccataaact ttacggcacc tggtttgaag     1740
aggagcaggt ctggattgcc ttcatcaaag gcagaatttc caattcctga tgggatagga     1800
gcaccagact ttagggaatc ttcaaggtcc caggaggtct tgcaaggtca agaaattatg     1860
```

| | |
|---|---:|
| agttttaatg ctctttatga tggtgttgat ggtcagaacc agcacccatc tgaaataagg | 1920 |
| agttgttttc ctggttacca cagttctggg attgctgcat taggaagtgg tatcagagac | 1980 |
| tcgattgcca cttcaaataa ctcctacaag gcataggct ttaacgaatc ttatagattc | 2040 |
| cataaggtct tccaaggtca agaaatttt ccaagctcac catatggaag aatcccaaat | 2100 |
| gctaatgagg ctcgtgaaaa ttgtagtctt ggattctctg atggtgtcca aggtcaagc | 2160 |
| tcaagctcaa gaaatggatg gtctacattg atgcagggct ataatactca aattcgacct | 2220 |
| cctgcacaag tatcatcacc atcttcggtg ttaatgtttc agcatgctag caatccagtt | 2280 |
| ccaaagccat cttccaattt taatttcaat gatcatgtgc agcagacagc taccacccga | 2340 |
| agttggtttt gtggtcctga aatgcagggg ggggatttca agttgcctgc acattctgag | 2400 |
| cccagtgtaa aaagaggcgg ccagtggagc aatagtcctt ttggtctgtc ccatgagcat | 2460 |
| cttcaacatg gtgtttcaca acctattgta gctcaatcag cctttagggg tagtcaagat | 2520 |
| ttggtgtcgt gcaaaagcag ctgcagactc tttggtttct cattgactga ggataaatgc | 2580 |
| cttgttaata aggaggacaa tatgaccta ataacatctc cattgaatcc tggatcctcc | 2640 |
| tttctgcctc gcgcaggaga gcacttccat ccaaagcctc cagcaataaa taatgcagtt | 2700 |
| gggagcagtt gtaccgaagc aattctgcaa acccgtgctg aaaattatcg aatatactaa | 2760 |
| tgaggctcgc acaagggatg cttcctgttg cttggttta tatgtattag cttgtgagag | 2820 |
| aatataatta ttctcctaag gtaacttggc tatatcctaa ctcctttgac tatgcaacag | 2880 |
| agctgtttgt acctggtact aatctctgtt agatttccca tgataaccca cattcaagaa | 2940 |
| tgttctcttc atacagtgca caatccaatc tggaaatgta gttgtaatag cgccagatat | 3000 |
| tttatatggt tgtcatctct caatatgttt tgttctatgc tagcc | 3045 |

```
<210> SEQ ID NO 25
<211> LENGTH: 2790
<212> TYPE: DNA
<213> ORGANISM: Vitis vinifera

<400> SEQUENCE: 25
```

| | |
|---|---:|
| atggtggcta tgatcgatct caacaccgtc gacgacgacg agacaccctc gtctgggtcg | 60 |
| tcgtcttcct cctcctcatc cgcctctgct tctgcttcca cagtttgtgg ttctttgttg | 120 |
| tcggcggcgt cgtcggtatg tttggagctg tggcacgcgt gtgctggccc gctcatatcg | 180 |
| cttccgaaga aaggcagcct tgtggtgtac tttccacagg gccacctgga gcagcttct | 240 |
| gattatccgg ccgtagccta tgatctcccg cctcacgtct tctgtcgagt ggttgatgtc | 300 |
| aagctccatg ccgaggtagt tacggatgaa gtttacgcac aggtctcgct ggttcctgaa | 360 |
| accaagcaga ttaagcagaa actgcaggaa ggggaaattg aagcagatgg tggtgaagaa | 420 |
| gaggatattg agggttctat caagtccatg acaccccaca tgttctgcaa aactcttact | 480 |
| gcttcagata ctagcaccca tgggggtttt tctgtcccc gccgagctgc agaggactgt | 540 |
| tttcctcccc tggattacaa acagcagaga ccttcacaag agcttgtggc caaagatttg | 600 |
| catggcttcg aatggagatt ccggcatatc tacagggggc agccaaggcg gcatttgctt | 660 |
| actactggtt ggagtgcatt tgtaaacaag aagaagcttg tgtctggaga tgctgtactc | 720 |
| tttcttaggg gtggggatgg agaactaaga ctgggaatcc gaagagcagc tcaaattaaa | 780 |
| ggttcgtctc ctttcccagc tctttgtagc aacagttga atctcaacac ccttacagct | 840 |
| gtggtcaatg ctatatccac aagaagtgtt ttcaacatat gctacaatcc gagggctagc | 900 |

```
tcatcagagt tcataatacc gctccgtaaa ttctcaaaga gcattgatca ttcatttct      960
gctgggatga ggttcaaaat gcgtgttgaa acagaagatg cagcagaacg aagatatact   1020
ggactgataa ctgggatcag tgacatggat cctgttagat ggcctggttc taaatggagg   1080
tgcctattgg taaggtggga cgatatagag gctaatcgac ataacagggt ttctccatgg   1140
gaaattgagc tatctggttc gctttctggt tctggcagct tgacagttcc tggctcaaag   1200
aggaccagga ttggttttgcc gggaactaga ccagattttt cagttcccaa tgggatggga   1260
gtgtcagact ttggggaatc ttcaaggttc cagaaggtct tgcaaggtca agaaattttt   1320
ggttttaaca ctccttatga tggtgttgat acccaggatc atcatccatc tgaaataagg   1380
tgttttcctg gttcaagttg ttctgggatt gctgcaatag gaaatggtgt tagaaaccct   1440
cttgggaatt ctgatatttc ctataaaggc ataggctttg gtgaatcttt tcgattccat   1500
aaggtcttgc aaggtcaaga acatttcca agcccaccat gtggaagagc tctgtctgct    1560
aaccaggctc atgaaaatgg tagctttgga atctttgatg gtgttcaagt gccgacttct   1620
agaaatggat ggcctgccct tgtgcaggga tataatgccc acactcacct gtccacacca   1680
tcagtgcaag tgtcgtcacc atcatcggtg ttaatgttcc agcaagcaag cactgctgct   1740
cctaacattt actcaatgca tagcgccaat aatcaggaga aggagcaaga aattagtaac   1800
cggagttcat ttgatattcc tgaagtgtat ggtgaaaagc tcacaccatc acgttgtgag   1860
cttagtgtca ggggaggagg tcagggaggt atgaatttct ttggtctgtt aaacgagcat   1920
aatcaactag ctgttccaca tcctcttgta actcaatcag catttagagg cagtcaagat   1980
ttagttccta catgtaaaag tagctgcagg ctctttggct tttccttaac ggaggaagaa   2040
agcattggaa ataaagtgga caaccccact cctgttacat cttcattgat tcctggaacc   2100
tcttttctgc cccagcagtt gcactcagag cctccggtga tgaccaaggc aattggaagc   2160
aattgtacca agtaagtga cttctatgct gtaagggata tgctttttga tattgcgctg   2220
tagcgtactc ctgttgtaag atcaaaattg caatttcaca agctggggag tgttgtagac   2280
caggcaatta atcgctggaa gcttgatagg catgatgatt tgatttgtgc attgaagcat   2340
ttatttgata tggagggagg gcttctgcat ggtgagggaa agttgtttac caggatcatg   2400
aggatgttgt gatgcttgtt cgagatgact catggcagga aatctgcagc atttgatgaa   2460
aaattatgat atttactaat gaagacgtag tgatggcacc aaacatagat gcttatagtt   2520
gctgagaggc acacatggca tcattgatat gtttttagct cttgggcgaa agaactgtaa   2580
ttattgccat aacagtaatg tatcttaacc tcccttgcta tggagaacaa tttaaactaa   2640
tttactaggt tccttggaat actcagttaa gaaattactt ttaaaactgt atcaaaatat   2700
tactctatgt tgttcatcag ttgtgttact gtattgcagc tattgcttct gtatctctgc   2760
ttaacattgt tggcttaagg ctgtttccca                                    2790
```

<210> SEQ ID NO 26
<211> LENGTH: 656
<212> TYPE: DNA
<213> ORGANISM: Malus domestica

<400> SEQUENCE: 26

```
aacaatgcgc ggctgccgtt gacgttagag tctacgctcc tctctctcct ctctctcctc     60
tctctctctc tctaccgttt ataaatcccg tcctcaaacg ccacttctac atcaccgccc    120
ctccctctga atcctctcc ctctctacgc tcctctctct cctctctctt ctctctcttc    180
tctctctcta ccgtttataa atcccctgtc ctcaaacgcc acttctacat caccacccc     240
```

```
cctctgaaa  atcctctttc  tctctctctc  tctctctctc  tctctgtgaa  aaagctctct     300
ctctctctct  ctgtgaaaaa  gttaaacttt  aattgcaata  tgcaatcaca  aactatccca     360
tatggaacat  ggattccggg  cacccgagcc  ggccacgcga  cgccgtcctc  acgcgacgcc     420
tcacgtgagc  aacacctagc  ggcggccagc  gtacaaaaaa  tggtgtcgga  gaatgctgtc     480
acggttgtcg  gacgacgtgg  ctgctgcatg  tgccacgtcg  tcaagcggct  gctcctcggt     540 cacgggtca  accctacggt  tttcggcgat  gagccagatc  tgaaacaagg  gcgaattctg     600
cagatatcca  tcacactggc  ggccgctcga  gcatgcatct  agagggccca  attcgc       656
```

<210> SEQ ID NO 27
<211> LENGTH: 421
<212> TYPE: DNA
<213> ORGANISM: Malus domestica

<400> SEQUENCE: 27

```
actctcgctc  ccggagctcc  tcaaccagtc  ggagcagctc  cgtcacgtcc  ggcggcttag      60
gctgcacctg  cgcggaggtg  cgtgggaagt  atacaccaaa  ggagcgcgag  aacaccgccc     120
ccttctgggg  tgtcttccca  gagctcaacg  aaggcgacgg  agactttgaa  ggagtttccg     180
gtttgggatt  cgccggcgat  tctgtagcc   ccattgccac  cctcaccttc  ccagcaacca     240
ttgcaaaacc  ccctctccct  ttcactcaac  accctgtttc  tctcactctc  tctctctctc     300
tctctctctc  tctctctctc  tctctctctc  tctaaaagtg  tgatgttcct               360
ctctcaagga  tttggggtgt  gtgattagct  tgcataatcc  agcacagagt  gaagggtta     420 c                                                                          421
```

<210> SEQ ID NO 28
<211> LENGTH: 707
<212> TYPE: PRT
<213> ORGANISM: Malus domestica

<400> SEQUENCE: 28

```
Met Ala Gly Leu Ile Asp Leu Asn Ser Ala Thr Glu Asp Glu Glu Thr
1               5                   10                  15

Pro Ser Ser Gly Ser Pro Ser Ser Ala Ser Ser Val Ser Asp Ala Leu
            20                  25                  30

Gly Ser Ser Ala Ser Val Cys Met Glu Leu Trp His Ala Cys Ala Gly
        35                  40                  45

Pro Leu Ile Ser Leu Pro Lys Lys Gly Ser Val Val Tyr Leu Pro
    50                  55                  60

Gln Gly His Leu Glu Gln Val Ser Asp Phe Pro Thr Ser Ala Tyr Asp
65                  70                  75                  80

Leu Pro Pro His Leu Phe Cys Arg Val Val Asp Val Lys Leu His Ala
                85                  90                  95

Glu Thr Gly Thr Asp Asp Val Phe Ala Gln Val Ser Leu Val Pro Glu
            100                 105                 110

Ser Glu Glu Ile Glu His Arg Leu Arg Glu Gly Val Thr Asp Ala Asp
        115                 120                 125

Ala Glu Glu Asp Val Glu Ala Met Gly Thr Ser Thr Pro His Met
    130                 135                 140

Phe Cys Lys Thr Leu Thr Ala Ser Asp Thr Ser Thr His Gly Gly Phe
145                 150                 155                 160

Ser Val Pro Arg Arg Ala Ala Glu Asp Cys Phe Pro Pro Leu Asp Tyr
                165                 170                 175
```

```
Thr Gln Gln Arg Pro Ser Gln Glu Leu Val Ala Lys Asp Leu His Gly
            180                 185                 190

Leu Glu Trp Arg Phe Arg His Ile Tyr Arg Gly Gln Pro Arg Arg His
            195                 200                 205

Leu Leu Thr Thr Gly Trp Ser Ala Phe Val Asn Lys Lys Lys Leu Val
            210                 215                 220

Ser Gly Asp Ala Val Leu Phe Leu Arg Gly Asp Asp Gly Glu Leu Arg
225                 230                 235                 240

Leu Gly Ile Arg Arg Ala Ala Gln Phe Lys Ser Ser Ala Thr Cys Pro
            245                 250                 255

Thr Leu Cys Ser Gln Gln Leu Asn Tyr Ser Thr Ile Thr Asp Val Val
            260                 265                 270

Asn Ala Ile Phe Ala Lys Asn Ala Phe Asn Val Tyr Tyr Asn Pro Arg
            275                 280                 285

Ser Ser Ser Ser Glu Phe Ile Ile Pro Ser His Lys Phe Leu Arg Ser
            290                 295                 300

Leu Asp His Cys Phe Cys Ala Gly Met Arg Ile Lys Met Arg Phe Glu
305                 310                 315                 320

Thr Glu Asp Ala Ala Glu Arg Arg Tyr Thr Gly Leu Ile Thr Gly Ile
            325                 330                 335

Ser Glu Leu Asp Pro Val Arg Pro Gly Ser Lys Trp Arg Cys Leu
            340                 345                 350

Val Val Arg Trp Asp Asp Ile Asp Thr Ser Lys His Gly Arg Val Ser
            355                 360                 365

Pro Trp Glu Val Glu Arg Ser Gly Ser Val Ser Ser Ser His Thr Leu
            370                 375                 380

Met Thr Thr Gly Leu Lys Arg Ser Arg Ile Gly Leu Ser Ala Thr Lys
385                 390                 395                 400

Pro Glu Phe Pro Val Pro Ser Met Ser Cys Asn Gly Ile Gly Thr Ser
            405                 410                 415

Asp Phe Gly Glu Ser Leu Arg Phe Gln Lys Val Leu Gln Gly Gln Glu
            420                 425                 430

Ile Ser Gly Phe Asp Thr Pro Phe Ser Gly Leu Gly Gly Leu Asn Ser
            435                 440                 445

His Pro Ser Glu Ala Arg Arg Val Phe His Gly Ser Gly Gly Ser Gly
            450                 455                 460

Ile Ala Ala Gly Gly Asn Gly Leu Arg Gln Ser Leu Val Asp Ser Glu
465                 470                 475                 480

Ile Ala Ser Lys Gly Ile Gly Phe Gly Glu Ser Phe Arg Phe His Lys
            485                 490                 495

Val Leu Gln Gly Gln Glu Ile Phe Pro Ser Ser Pro Tyr Gly Arg Ala
            500                 505                 510

Pro Ala Ser Asn Glu Ala His Glu Tyr Gly Gly Pro Gly Leu Tyr Asp
            515                 520                 525

Gly Phe Gln Val Pro Gly Phe Arg Asn Gly Trp Ser Thr Met Met Gln
            530                 535                 540

Ser Asn Asn Thr Asn Val His Ser Ser Ala Pro Ser Val Gln Val Ser
545                 550                 555                 560

Ser Pro Ser Ser Val Leu Met Phe Gln Gln Ala Met Asn Pro Val Ala
            565                 570                 575

Glu Phe Asn Ser Val Tyr Asn Gly His Asn Gln Glu Asp His Arg Val
            580                 585                 590
```

```
Asn Arg Thr Pro His Val Leu Glu His Asp Gly Gly Arg Gln Thr Ser
        595                 600                 605

Ser Ser Phe Gly Glu Arg Asn Phe Ser Arg Glu Asp Arg Gly Gly Thr
    610                 615                 620

His Ser Tyr Asn Gln His Gly Ile Ser Pro His Pro Val Ile Ser Gln
625                 630                 635                 640

Ser Thr Ile Ser Gly Ser Gln Asp Ser Val Ser Pro Ile Lys Gly Ser
                645                 650                 655

Cys Arg Leu Phe Gly Phe Ser Leu Ser Glu Asp Lys Cys Val Pro Asp
                660                 665                 670

Gln Glu Gly Asn Pro Asn Val Gly Val Gln Phe His Ser Lys Pro Pro
                675                 680                 685

Leu Met Thr Ser Thr Val Gly Ile Thr Cys Thr Lys Val Ser Asn Leu
    690                 695                 700

Phe Ala Ala
705

<210> SEQ ID NO 29
<211> LENGTH: 707
<212> TYPE: PRT
<213> ORGANISM: Malus domestica

<400> SEQUENCE: 29

Met Ala Gly Leu Ile Asp Leu Asn Ser Ala Thr Glu Asp Glu Glu Thr
1               5                   10                  15

Pro Ser Ser Gly Ser Pro Ser Ser Ala Ser Ser Val Ser Asp Ala Leu
                20                  25                  30

Gly Ser Ser Ala Ser Val Cys Met Glu Leu Trp His Ala Cys Ala Gly
            35                  40                  45

Pro Leu Ile Ser Leu Pro Lys Lys Gly Ser Val Val Tyr Leu Pro
        50                  55                  60

Gln Gly His Leu Glu Gln Val Leu Asp Phe Pro Thr Ser Ala Tyr Asp
65              70                  75                  80

Leu Pro Pro His Leu Phe Cys Arg Val Val Asp Val Lys Leu His Ala
                85                  90                  95

Glu Thr Gly Thr Asp Asp Val Phe Ala Gln Val Ser Leu Val Pro Glu
            100                 105                 110

Ser Glu Glu Ile Glu His Arg Leu Arg Glu Gly Val Thr Asp Ala Asp
        115                 120                 125

Ala Glu Glu Asp Val Glu Ala Met Gly Thr Ser Thr Thr Pro His Met
130                 135                 140

Phe Cys Lys Thr Leu Thr Ala Ser Asp Thr Ser Thr His Gly Gly Phe
145                 150                 155                 160

Ser Val Pro Arg Arg Ala Ala Glu Asp Cys Phe Pro Pro Leu Asp Tyr
                165                 170                 175

Thr Gln Gln Arg Pro Ser Gln Glu Leu Val Ala Lys Asp Leu His Gly
            180                 185                 190

Leu Glu Trp Arg Phe Arg His Ile Tyr Arg Gly Gln Pro Arg Arg His
        195                 200                 205

Leu Leu Thr Thr Gly Trp Ser Ala Phe Val Asn Lys Lys Lys Leu Val
210                 215                 220

Ser Gly Asp Ala Val Leu Phe Leu Arg Gly Asp Asp Gly Glu Leu Arg
225                 230                 235                 240

Leu Gly Ile Arg Arg Ala Ala Gln Phe Lys Ser Ser Ala Thr Cys Pro
                245                 250                 255
```

```
Thr Leu Cys Ser Gln Gln Leu Asn Tyr Ser Thr Ile Thr Asp Val Val
            260                 265                 270

Asn Ala Ile Phe Ala Lys Asn Ala Phe Asn Val Tyr Tyr Asn Pro Arg
            275                 280                 285

Ser Ser Ser Ser Glu Phe Ile Ile Pro Ser His Lys Phe Leu Arg Ser
            290                 295                 300

Leu Asp His Cys Phe Cys Ala Gly Met Arg Ile Lys Met Arg Phe Glu
305                 310                 315                 320

Thr Glu Asp Ala Ala Glu Arg Arg Tyr Thr Gly Leu Ile Thr Gly Ile
                325                 330                 335

Ser Glu Leu Asp Pro Val Arg Trp Pro Gly Ser Lys Trp Arg Cys Leu
            340                 345                 350

Val Val Arg Trp Asp Asp Ile Asp Thr Ser Lys His Gly Arg Val Ser
            355                 360                 365

Pro Trp Glu Val Glu Arg Ser Gly Ser Val Ser Ser His Thr Leu
    370                 375                 380

Met Thr Thr Gly Leu Lys Arg Ser Arg Ile Gly Leu Ser Ala Thr Lys
385                 390                 395                 400

Pro Glu Phe Pro Val Pro Ser Met Ser Cys Asn Gly Ile Gly Thr Ser
                405                 410                 415

Asp Phe Gly Glu Ser Leu Arg Phe Gln Lys Val Leu Gln Gly Gln Glu
                420                 425                 430

Ile Ser Gly Phe Asp Thr Pro Phe Ser Gly Leu Gly Gly Leu Asn Ser
            435                 440                 445

His Pro Ser Glu Ala Arg Arg Val Phe His Gly Ser Gly Gly Ser Gly
            450                 455                 460

Ile Ala Ala Gly Gly Asn Gly Leu Arg Gln Ser Leu Val Asp Ser Glu
465                 470                 475                 480

Ile Ala Ser Lys Gly Ile Gly Phe Gly Glu Ser Phe Arg Phe His Lys
                485                 490                 495

Val Leu Gln Gly Gln Glu Ile Phe Pro Ser Pro Tyr Gly Arg Ala
            500                 505                 510

Pro Ala Ser Asn Glu Ala His Glu Tyr Gly Gly Pro Gly Leu Tyr Asp
            515                 520                 525

Gly Phe Gln Val Pro Gly Phe Arg Asn Gly Trp Ser Thr Met Met Gln
    530                 535                 540

Ser Asn Asn Thr Asn Val His Ser Ser Ala Pro Ser Val Gln Val Ser
545                 550                 555                 560

Ser Pro Ser Ser Val Leu Met Phe Gln Gln Ala Met Asn Pro Val Ala
                565                 570                 575

Glu Phe Asn Ser Val Tyr Asn Gly His Asn Gln Glu Asp His Arg Val
                580                 585                 590

Asn Arg Thr Pro His Val Leu Glu His Asp Gly Gly Arg Gln Thr Ser
            595                 600                 605

Ser Ser Phe Gly Glu Arg Asn Phe Ser Arg Glu Asp Arg Gly Gly Thr
    610                 615                 620

His Ser Tyr Asn Gln His Gly Ile Ser Pro His Pro Val Ile Ser Gln
625                 630                 635                 640

Ser Thr Ile Ser Gly Ser Gln Asp Ser Val Ser Pro Ile Lys Gly Ser
                645                 650                 655

Cys Arg Leu Phe Gly Phe Ser Leu Ser Glu Asp Lys Cys Val Pro Asp
                660                 665                 670
```

-continued

```
Gln Glu Gly Asn Pro Asn Val Gly Val Gln Phe His Ser Lys Pro Pro
        675                 680                 685
Leu Met Thr Ser Thr Val Gly Ile Thr Cys Thr Lys Val Ser Asn Leu
        690                 695                 700
Phe Ala Ala
705

<210> SEQ ID NO 30
<211> LENGTH: 19
<212> TYPE: DNA
<213> ORGANISM: Artificial Sequence
<220> FEATURE:
<223> OTHER INFORMATION: Forward primer

<400> SEQUENCE: 30
gctgccgttg acgttagag                                                  19

<210> SEQ ID NO 31
<211> LENGTH: 23
<212> TYPE: DNA
<213> ORGANISM: Artificial Sequence
<220> FEATURE:
<223> OTHER INFORMATION: Reverse primer

<400> SEQUENCE: 31
gtttgtagaa gtggcgtttg agg                                             23

<210> SEQ ID NO 32
<211> LENGTH: 20
<212> TYPE: DNA
<213> ORGANISM: Artificial Sequence
<220> FEATURE:
<223> OTHER INFORMATION: Forward primer

<400> SEQUENCE: 32
ttgaaggagt ttccggtttg                                                 20

<210> SEQ ID NO 33
<211> LENGTH: 24
<212> TYPE: DNA
<213> ORGANISM: Artificial Sequence
<220> FEATURE:
<223> OTHER INFORMATION: Reverse primer

<400> SEQUENCE: 33
gtttcactct gtgctggatt atgc                                            24

<210> SEQ ID NO 34
<211> LENGTH: 18
<212> TYPE: DNA
<213> ORGANISM: Artificial Sequence
<220> FEATURE:
<223> OTHER INFORMATION: Synthetic construct

<400> SEQUENCE: 34
tgtaaaacga cggccagt                                                   18
```

COMPOSITIONS AND METHODS FOR MANIPULATING THE DEVELOPMENT OF PLANTS

CROSS-REFERENCE TO RELATED APPLICATIONS

This application is a continuation application of U.S. application Ser. No. 16/062,597, filed June 14, 18, which is a U.S. National Stage Application filed under 35 U.S.C. § 371 of International Application No. PCT/IB2016/057631, filed Dec. 14, 2016, which claims the benefit of New Zealand Application No. 714988, filed Dec. 16, 2015. All of these applications are hereby incorporated by reference in their entireties.

REFERENCE TO A SEQUENCE LISTING

A sequence listing containing SEQ ID Nos. 1-34, created on Dec. 16, 2020, having a size of 137 kb, and entitled "51-18A_Sequence_Listing", is provided herewith in a computer-readable nucleotide/amino acid .txt file and is specifically incorporated by reference.

TECHNICAL FIELD

The invention relates to compositions and methods for the manipulation of plant development.

BACKGROUND OF THE INVENTION

Dwarfing rootstocks have revolutionized the production of some tree and vine crops, by permitting high-density plantings that increase fruit yield in the early years of orchard establishment (Ferree and Carlson 1987; Webster and Wertheim 2003; Gregory and George 2011). The widespread use of dwarfing rootstocks has led to a steady increase in the efficiency of apple production over the past century (Hirst and Ferree 1995; Webster 1995).

'Mailing9' ('M9') is the most frequently used apple dwarfing rootstock in both commercial and home orchards (Webster 1995). 'M9', originally called 'Jaune de Metz', was discovered as single seedling in the 1800s and was clonally propagated as a rootstock because of its effects on both precocity and vigour control of the grafted scion (Carriére 1897). At the beginning of the 20th century, all the apple rootstocks grown in Western Europe were collected at the East Mailing Research Station (UK) and classified according to their effect on the grafted scion (Hatton 1917). Many of the apple rootstock varieties bred worldwide have parentage derived from this 'Mailing' series, particularly 'M9' (Manhart 1995; Webster and Wertheim 2003). Progeny of 'M9' segregate for rootstock-induced dwarfing, indicating that this trait is determined by one or more genetic factors.

Dwarfing is a complex phenomenon, with some dwarfing-associated phenotypes being exhibited in the root stock plant, and other dwarfing-associated phenotypes being exhibited in scions grafted onto the root stock plants.

Phenotypes reported in M9 root stock plants include: altered xylem/phloem ratio, more phloem elements, smaller phloem elements, thicker bark, altered auxin transport, slower auxin transport, and reduced apical dominance. Grown as an un-grafted plant, M9 is also bushier than other types of non-grafted apples.

Based on the altered xylem/phloem phenotypes, researchers have suggested that dwarfing roots tocks function by altering the transport of water, nutrients or hormones. A number of studies have measured hormone concentration and/or movement in dwarfing rootstocks; auxin in particular seems to play a major role in rootstock induced dwarfing (Hooijdonk, Woolley et al. 2011). Soumelidou was the first to demonstrate that 'M9' apple stems transport auxin at a slower rate than non-dwarfing stems (Soumelidou K 1994). More recently, it has been shown that treating apple trees with NPA, a polar auxin transport inhibitor, phenocopies the effect of a dwarfing rootstock (van Hooijdonk 2010).

Despite M9 rootstocks being so widely used and the subjects of numerous studies, the underlying mechanism by which dwarfing rootstocks control both scion vigour and flowering remains unresolved.

In woody perennials where a dwarfing or vigour-reducing rootstock exists, the overall effect on the grafted scion is characterised by less vegetative growth, earlier termination of shoot growth, earlier competency to flower than non-grafted trees or trees on vigorous rootstocks (also called precocity), earlier phase change (a term which is related to earlier flowering, but also encompasses other traits, such as thorns, leaf shape, etc), a smaller canopy, reduced stem circumference (or TCA, Trunk Cross-sectional Area), weaker shoot system, reduced branch diameter.

The first detectable effects on apple scions grafted onto M9 rootstock are fewer and shorter sylleptic branches (axillary meristems that grow out in the same season they were initiated), more axillary flowers (these do not appear until the spring of year two, but are formed in summer of year 1), and a tendency for both the primary axis and secondary axes to terminate earlier (Seleznyova, Thorp et al. 2003; Seleznyova, Tustin et al. 2008; van Hooijdonk, Woolley et al. 2010; van Hooijdonk, Woolley et al. 2011).

An increased proportion of axillary floral buds along the primary axis can have a profound impact on the subsequent growth of the scion. In a floral bud, the sympodial "bourse" shoot that develops from an axillary meristem is much less vigorous than the monopodial shoot that continues growth from the apex of a vegetative bud. Bourse shoots do not begin extension until anthesis of the flowers and are developmentally delayed relative to monopodial shoots, which begin growth immediately after budbreak. The effects of increased flowering and reduced sylleptic shoot number and length in year one became amplified in successive growth seasons, and within three years, scions grafted on dwarf or semi-dwarf rootstocks exhibited a distinctly reduced canopy size and branching density.

Quantitantive trait loci (QTL) associated with dwarfing have been identified in apple dwarf rootstock. For example, Pilcher et al (2008) generated a segregating rootstock population derived from a cross of 'M9' and the vigorous rootstock 'Robusta 5' ('R5'). The progeny were all grafted with 'Braeburn' scions and the scions were phenotyped over seven years. Using a bulked segregant analysis (comparing pooled rootstock DNAs from dwarfed and vigorous trees) of a the rootstock population, the authors identified a major dwarfing locus (Dw1) derived from 'M9' and located at the top of linkage group (LG) 5 (Pilcher, Celton et al. 2008) (FIG. 1a). Some of the vigorous individuals in this population carried Dw1, suggesting there were one or more additional rootstock loci that influence dwarfing of the scion. Using an enlarged population from the same cross, a genetic map was constructed which enabled a multi-trait quantitative trait locus (QTL) analysis of rootstock-induced dwarfing (Celton, Tustin et al. 2009).

More recently Fazio et al characterised two dwarfing loci Dw1 and Dw2 and reported that the strongest degree of dwarfing was conferred by rootstock with both Dw1 and Dw2 whereas either Dw1 or Dw2 alone affected dwarfing (Celton et al 2009). The authors also reported the Dw1 QTL to be located between the marking Hi22f12 and Hi04a08 defining an interval of 2.46 Mb.

The introduction of dwarfing into new apple cultivars is only currently achievable, through the laborious and slow procedures of breeding. Breeding of any fruit is also of course limited by the compatability of breeding species.

It would be beneficial to have tools or methods to introduce dwarfing, or dwarfing-associated phenotypes into new species where dwarfing technology is not yet available. Furthermore, even in species where dwarfing technology is available, it would also be advantageous to be able to more efficiently introduce dwarfing into certain cultivars, or root stock cultivars, that are well adapted to their local environment.

It is an object of the invention to provide materials and methods for producing dwarfing and/or at least one dwarfing-associated phenotype in plant, and/or at least to provide the public with a useful choice.

SUMMARY OF THE INVENTION

Method

In the first aspect the invention provides a method for producing a plant with at least one dwarfing-associated phenotype the method comprising altering the expression, or activity, of an ARF3 polypeptide in the plant.

In one embodiment the method comprises increasing the expression of the ARF3 polypeptide in the plant.

In a further embodiment the method comprises transforming the plant to express the ARF3 polypeptide in the plant.

In a further embodiment the method comprises transforming the plant with polynucleotide encoding the ARF3 polypeptide.

In a further embodiment the polynucleotide is operably linked to a heterologous promoter.

In a further embodiment the method comprises modifying the sequence of an endogenous polynucleotide encoding the ARF3 polypeptide in the plant.

In one embodiment, modifying the endogenous polynucleotide alters the activity of the ARF3 polypeptide in the plant to induce the dwarfing-associated phenotype.

In one embodiment the dwarfing-associated phenotype is selected from:
 a) altered auxin transport,
 b) slower auxin transport,
 c) reduced apical dominance,
 d) an altered xylem/phloem ratio,
 e) an increased number of phloem elements,
 f) smaller phloem elements,
 g) thicker bark,
 h) a bushier habit,
 i) reduced root mass,
 j) reduced vigour,
 k) less vegetative growth,
 l) earlier termination of shoot growth,
 m) earlier competence to flower,
 n) precocity,
 o) earlier phase change,
 p) smaller canopy,
 q) reduced stem circumference,
 r) reduced branch diameter,
 s) fewer sylleptic branches,
 t) shorter sylleptic branches,
 u) more axillary flowers,
 v) an earlier teminating primary axis,
 w) earlier teminating secondary axes,
 x) shorter intenode length, and
 y) reduced scion mass.

In one embodiment the dwarfing-associated phenotype is selected from a) to i). In a further embodiment the dwarfing-associated phenotype is selected from a) to h). In one embodiment a plant with at least one of these phenotypes is suitable for use as a rootstock plant. In a further embodiment the dwarfing-associated phenotype in this plant is at least one of reduced apical dominance, a bushier habit, an altered xylem/phloem ratio, an increased number of phloem elements, and reduced root mass.

In a further embodiment the dwarfing-associated phenotype is the competence to induce at least one of a) to y) in a scion grafted on to the plant. In a further embodiment the dwarfing-associated phenotype is the competence to induce at least one of a) to h) and j) to x) in a scion grafted on to the plant.

In a preferred embodiment the dwarfing-associated phenotype is the competence to induce at least one of j) to y) in a scion grafted on to the plant.

In a further embodiment the dwarfing-associated phenotype is the competence to induce at least one of: reduced vigour, less vegetative growth, earlier termination of shoot growth, a smaller canopy, reduced stem circumference, and reduced scion mass in a scion grafted on to the plant.

In a further embodiment the method includes the step of grafting a scion on to a plant produced by the method.

In a further embodiment the dwarfing-associated phenotype is the competence to induce at least one of: reduced vigour, less vegetative growth, earlier termination of shoot growth, a smaller canopy, and reduced stem circumference, in a scion grafted on to the plant.

In a further embodiment the method includes the step of grafting a scion on to a plant produced by the method.

In one embodiment the dwarfing-associated phenoytype is exhibited in a scion grafted onto the plant.

In one embodiment the dwarfing-associated phenoytype exhibited in the scion is at least one of j) to y). In one embodiment the dwarfing-associated phenoytype exhibited in the scion is at least one of j) to x).

In a further embodiment the dwarfing-associated phenoytype exhibited in the scion is at least one of: reduced vigour, less vegetative growth, earlier termination of shoot growth, a smaller canopy, reduced stem circumference, and reduced scion mass, in a scion grafted on to the plant.

In a further embodiment the dwarfing-associated phenoytype exhibited in the scion is at least one of: reduced vigour, less vegetative growth, earlier termination of shoot growth, a smaller canopy, and reduced stem circumference, in a scion grafted on to the plant.

In a further embodiment the invention provides a method of producing a plant with at least one dwarfing-associated phenotype selected from:
 a) altered auxin transport,
 b) slower auxin transport,
 c) reduced apical dominance,
 d) an altered xylem/phloem ratio,
 e) an increased number of phloem elements,
 f) smaller phloem elements,
 g) thicker bark,
 h) a bushier habit,
 i) reduced root mass,
 j) reduced vigour,
 k) less vegetative growth,
 l) earlier termination of shoot growth,
 m) earlier competence to flower, n) precocity,
o) earlier phase change,
p) smaller canopy,
q) reduced stem circumference,
r) reduced branch diameter,
s) fewer sylleptic branches,
t) shorter sylleptic branches,
u) more axillary flowers,
v) an earlier teminating primary axis,
w) earlier teminating secondary axes,
x) shorter intenode length, and
y) reduced scion mass,
the method comprising grafting a scion onto a plant produced by a method of the invention.

In this embodiment the at least one dwarfing-associated phenotype is preferably exhibited in the grafted scion. In this embodiment the grafted scion exhibits at least one of j) to y). In a further the grafted scion exhibits at least one of j) to x).

In a further embodiment the grafted scion preferably exhibits at least one of reduced vigour, less vegetative growth, earlier termination of shoot growth, a smaller canopy, reduced stem circumference, and reduce scion mass, in a scion grafted on to the plant.

In a further embodiment the grafted scion preferably exhibits at least one of reduced vigour, less vegetative growth, earlier termination of shoot growth, a smaller canopy, and reduced stem circumference, in a scion grafted on to the plant.

In a further embodiment the invention provides a method for producing a plant with at least one dwarfing-associated phenotype selected from:
a) altered auxin transport,
b) slower auxin transport,
c) reduced apical dominance,
d) an altered xylem/phloem ratio,
e) an increased number of phloem elements,
f) smaller phloem elements,
g) thicker bark,
h) a bushier habit,
i) reduced root mass,
j) reduced vigour,
k) less vegetative growth,
l) earlier termination of shoot growth,
m) earlier competence to flower,
n) precocity,
o) earlier phase change,
p) smaller canopy,
q) reduced stem circumference,
r) reduced branch diameter,
s) fewer sylleptic branches,
t) shorter sylleptic branches,
u) more axillary flowers,
v) an earlier teminating primary axis,
w) earlier teminating secondary axes,
x) shorter intenode length,
y) reduced scion mass,
the method comprising the steps:
A. providing a plant with altered the expression or activity of a ARF3 polypeptide,
B. grafting a scion onto the plant in A
wherein at least one of j) to y) is exhibited in the scion grafted on to the plant in A.

In a further embodiment at least one of j) to x) is exhibited in the scion grafted on to the plant in A.

In a further embodiment the grafted scion preferably exhibits at least one of reduced vigour, less vegetative growth, earlier termination of shoot growth, a smaller canopy, reduced stem circumference, and reduced scion mass, in a scion grafted on to the plant.

In a further embodiment the grafted scion preferably exhibits at least one of reduced vigour, less vegetative growth, earlier termination of shoot growth, a smaller canopy, and reduced stem circumference, in a scion grafted on to the plant.

In one embodiment the plant in A has increased expression of the ARF3 polypeptide.

In a further embodiment the plant in A has been transformed to express the ARF3 polypeptide.

In a further embodiment the plant in A is transgenic for a polynucleotide encoding the ARF3 polypeptide.

In a further embodiment the polynucleotide is operably linked to a heterologous promoter.

In a further embodiment the plant in A comprises a modification in an endogenous polynucleotide encoding the ARF3 polypeptide in the plant.

In a further embodiment the modification alters the activity of the ARF3 polypeptide in the plant to induce the dwarfing-associated phenotype.

ARF3 polypeptide/polynucleotides used in the methods of the invention

In one embodiment of the methods above the ARF3 polypeptide has a sequence with at least 70% identity to any one of SEQ ID NO:1 to 11, 28 and 29.

In a further embodiment the polypeptide has a sequence with at least 70% identity to SEQ ID NO:1 (MdARF3).

In a further embodiment the polypeptide has a sequence with at least 70% identity to SEQ ID NO:28 (MdARF3).

In most known ARF3 polypeptide sequences either a Serine or Proline residue is found at the position corresponding amino acid residue 72 in SEQ ID NO:1 or 28 (MdARF3) as shown in FIG. 8.

In a further embodiment the polypeptide comprises a hydrophobic amino acid residue at the position corresponding amino acid residue 72 in SEQ ID NO:28 (MdARF3).

In a further embodiment the polypeptide comprises a Leucine residue at a position corresponding the amino acid residue 72 in SEQ ID NO:28 (MdARF3).

In a further embodiment the polypeptide comprises the sequence of SEQ ID NO:2 (M9 MdARF3).

In a further embodiment the polypeptide comprises the sequence of SEQ ID NO:29 (M9 MdARF3).

In one embodiment the ARF3 polynucleotide is a polynucleotide that encodes and ARF3 polypeptide.

Modification of an Endogenous Polynucleotide

In one embodiment the modification results in expression of an ARF3 polypeptide with a hydrophobic amino acid residue at a position corresponding the amino acid residue 72 in SEQ ID NO:1 or 28 (MdARF3).

In a preferred embodiment the hydrophobic amino acid is a Leucine residue.

In one embodiment the modification results in a codon encoding the Leucine residue.

In one embodiment the codon is found at a position corresponding to nucleotides 214 to 216 in the ARF3 polynucleotide of SEQ ID NO:12.

In one embodiment the codon is selected from: TTA, TTG, CTT, CTC, CTA and CTG.

In a preferred embodiment the codon is TTG.

Thus in a preferred embodiment, the modification results in a T nucleotide at a position corresponding to nucleotide 215 in the ARF3 polynucleotide of SEQ ID NO:12.

Polynucleotide Encoding a M9 Type ARF3 Polypeptide

In a further aspect, the invention provides an isolated polynucleotide encoding an ARF3 polypeptide comprising a hydrophobic amino acid residue at a position corresponding the amino acid residue 72 in SEQ ID NO:1 or 28 (MdARF3).

In a further embodiment the invention provides a polynucleotide encoding a variant of fragment of the ARF3 polypeptide.

In one embodiment, the hydrophobic amino acid residue is a Leucine residue.

Thus, in one embodiment, the invention provides an isolated polynucleotide encoding an ARF3 polypeptide comprising a Leucine residue at a position corresponding the amino acid residue 72 in SEQ ID NO:1 or 28 (MdARF3).

In a further embodiment the ARF3 polypeptide comprising comprises at least 70% identity to SEQ ID NO:2 or 29 (MdARF3).

In a further embodiment the polypeptide comprises the sequence of SEQ ID NO:2 or 29 (M9 MdARF3).

In a further embodiment the polypeptide comprises the sequence of SEQ ID NO:29 (M9 MdARF3).

In one embodiment the polynucleotide has at least 70% identity to at least one of SEQ ID NO:14 and 15.

In a further embodiment the polynucleotide has at least 70% identity to SEQ ID NO:14.

In a further embodiment the polynucleotide has at least 70% identity to SEQ ID NO:15.

In a further embodiment the polynucleotide comprises the sequence of SEQ ID NO:14 or 15.

In a further embodiment the polynucleotide comprises the sequence of SEQ ID NO:14.

In a further embodiment the polynucleotide comprises the sequence of SEQ ID NO:15.

Preferably the fragment of the ARF3 polypeptide comprises at least 50 contiguous amino acids, more preferably at least 100 contiguous amino acids, more preferably at least 150 contiguous amino acids, more preferably at least 200 contiguous amino acids, more preferably at least 250 contiguous amino acids, more preferably at least 300 contiguous amino acids, more preferably at least 350 contiguous amino acids, more preferably at least 400 contiguous amino acids, more preferably at least 450 contiguous amino acids of the polypeptide of the invention.

Preferably the fragment comprises the hydrophobic amino acid residue at a position corresponding the amino acid residue 72 in SEQ ID NO:1 or 28 (MdARF3).

Preferably the fragment comprises the hydrophobic amino acid residue at a position corresponding the amino acid residue 72 in SEQ ID NO:28 (MdARF3).

Preferably the hydrophobic amino acid residue is a Leucine residue.

Polynucleotide

In a further aspect the invention provides an isolated polynucleotide comprising the sequence of SEQ ID NO:14 or 15.

In one embodiment the polynucleotide comprising the sequence of SEQ ID NO:14.

In one embodiment the polynucleotide comprising the sequence of SEQ ID NO:15.

In a further embodiment the invention provides a variant or fragment of the polynucleotide.

Polypeptide

In a further aspect, the invention provides an isolated ARF3 polypeptide comprising a hydrophobic amino acid residue at a position corresponding the amino acid residue 72 in SEQ ID NO:1 or 28 (MdARF3).

In a further embodiment the ARF3 polypeptide comprises a hydrophobic amino acid residue at a position corresponding the amino acid residue 72 in SEQ ID NO:1 or 28 (MdARF3).

In a further embodiment the invention provides a variant of fragment of the ARF3 polypeptide.

In one embodiment, the hydrophobic amino acid residue is a Leucine residue.

Thus, in one embodiment, the invention provides an isolated ARF3 polypeptide comprising a Leucine residue at a position corresponding the amino acid residue 72 in SEQ ID NO:1 or 28 (MdARF3).

In a further embodiment the ARF3 polypeptide comprising comprises at least 70% identity to SEQ ID NO:2 or 29 (M9 MdARF3).

In a further embodiment the polypeptide comprises the sequence of SEQ ID NO:2 (M9 MdARF3).

In a further embodiment the polypeptide comprises the sequence of SEQ ID NO:29 (M9 MdARF3).

Polypeptide Fragment

Preferably the fragment comprises at least 50 contiguous amino acids, more preferably at least 100 contiguous amino acids, more preferably at least 150 contiguous amino acids, more preferably at least 200 contiguous amino acids, more preferably at least 250 contiguous amino acids, more preferably at least 300 contiguous amino acids, more preferably at least 350 contiguous amino acids, more preferably at least 400 contiguous amino acids, more preferably at least 450 contiguous amino acids of the polypeptide of the invention.

Preferably the fragment comprises the hydrophobic amino acid residue at a position corresponding the amino acid residue 72 in SEQ ID NO:1 or 28 (MdARF3).

Preferably the fragment comprises the hydrophobic amino acid residue at a position corresponding the amino acid residue 72 in SEQ ID NO: 28 (MdARF3).

Preferably the hydrophobic amino acid residue is a Leucine residue.

Polynucleotide Fragment/Primers and Probes

Preferably the polynucleotide fragment comprises at least 5 contiguous nucleotides, more preferably at least 10 contiguous nucleotides, more preferably at least 15 contiguous nucleotides, more preferably at least 20 contiguous nucleotides, more preferably at least 21 contiguous nucleotides, more preferably at least 30 contiguous nucleotides, more preferably at least 50 contiguous nucleotides, more preferably at least 100 contiguous nucleotides, more preferably at least 150 contiguous nucleotides, more preferably at least 200 contiguous nucleotides, more preferably at least 250 contiguous nucleotides, more preferably at least 300 contiguous nucleotides, more preferably at least 350 contiguous nucleotides, more preferably at least 400 contiguous nucleotides, more preferably at least 450 contiguous nucleotides of the polynucleotide of the invention.

In a preferred embodiment, the fragment of the polynucleotide of the invention, encodes a polypeptide fragment of the invention.

In one embodiment the invention provides a primer consisting of a polynucleotide fragment of the invention.

In a further embodiment the invention provides a probe consisting of a polynucleotide fragment of the invention.

Construct

In a further embodiment the invention provides a construct comprising a polynucleotide of the invention.

In one embodiment the construct comprises the polynucleotide sequence operably linked to a heterologous promoter.

Cells

In a further embodiment the invention provides a cell comprising a polynucleotide of the invention.

Preferably the cell is transgenic for the polynucleotide.

Preferably the transgenic cell, is transformed to comprise the polynucleotide of the invention. Alternatively, a predecessor of the cell has been transformed to comprise the polynucleotide, and the cell is an off-spring of the predecessor cell and has inherited the polynucleotide that was transformed into the predecessor cell.

In a further embodiment the invention provides a cell comprising a genetic construct of the invention.

In a preferred embodiment the cell expresses the polynucleotide of the invention.

In a preferred embodiment the cell expresses the polypeptide of the invention.

In a preferred embodiment the cell is transformed or genetically modified to expresses the polynucleotide or polypeptide of the invention.

In one embodiment the cell is a plant cell.

Plant

In a further embodiment the invention provides a plant comprising a polynucleotide of the invention.

Preferably the plant is transgenic for the polynucleotide. Preferably the transgenic plant is transformed to comprise the polynucleotide of the invention. Alternatively, a predecessor of the plant has been transformed to comprise the polynucleotide, and the plant is an off-spring of the predecessor plant and has inherited the polynucleotide that was transformed into the predecessor plant.

In a further embodiment the invention provides a plant comprising a genetic construct of the invention.

In a preferred embodiment the plant expresses the polynucleotide of the invention.

In a preferred embodiment the plant expresses the polypeptide of the invention.

In a preferred embodiment the plant is transformed or genetically modified to expresses the polynucleotide or polypeptide of the invention.

In one embodiment the plant comprises a plant cell of the invention.

In a further embodiment the plant has a dwarfing-associated phenotype as described above.

Plant Parts

In a further embodiment the invention provides a part, propagule or progeny of a plant of the invention.

Preferably the part, propagule or progeny is transgenic for the polynucleotide. Preferably the transgenic part, propagule or progeny is transformed to comprise the polynucleotide of the invention. Alternatively, a predecessor of the plant (that provided the part, propagule or progeny) has been transformed to comprise the polynucleotide, and the part, propagule or progeny provided by an off-spring of the predecessor plant and has inherited the polynucleotide that was transformed into the predecessor plant.

In a further embodiment the invention provides a part, propagule or progeny comprising a genetic construct of the invention.

In a preferred embodiment the part, propagule or progeny expresses the polynucleotide of the invention.

In a preferred embodiment the part, propagule or progeny expresses the polypeptide of the invention.

In a preferred embodiment the part, propagule or progeny is transformed or genetically modified to expresses the polynucleotide or polypeptide of the invention.

In one embodiment the part, propagule or progeny comprises a plant cell of the invention.

In one embodiment the plant cell, part, propagule or progeny can be rejgenrated into a plant with a dwarfing-associated phenotype as described above.

Marker Assisted Selection

In a further aspect the invention provides a method for identifying a plant with a genotype indicative of at least one dwarfing-associated phenotype, the method comprising testing a plant for at least one of:
 a) altered expression of at least one ARF3 polypeptide,
 b) altered expression of at least one ARF3 polynucleotide,
 c) presence of a marker associated with altered expression of at least one ARF3 polypeptide,
 d) presence of a marker associated with altered expression of at least one ARF3 polynucleotide,
 e) presence of a marker associated with altered activity of at least one ARF3 polypeptide, In one embodiment presence of any of a) to e) indicates that the plant has at least one dwarfing-associated phenotype.

In one embodiment dwarfing-associated phenotype is selected from those described above.

In one embodiment the altered expression is increased expression.

In one embodiment the marker associated with altered activity of at least one ARF3 polypeptide is presence of a hydrophobic amino acid residue at a position corresponding the amino acid residue 72 in SEQ ID NO:1 (MdARF3).

In one embodiment, the hydrophobic amino acid residue is a Leucine residue.

Thus, in one embodiment, the invention the method involves identifying presence of a Leucine residue at a position corresponding the amino acid residue 72 in SEQ ID NO:1 (MdARF3).

In a further embodiment the ARF3 polypeptide comprising comprises at least 70% identity to SEQ ID NO:2 (MdARF3).

In a further embodiment the polypeptide comprises the sequence of SEQ ID NO:2 (M9 MdARF3).

Alternatively, the method involves detection of a polynucleotide encoding the Leucine residue at a position corresponding the amino acid residue 72 in SEQ ID NO:1 (MdARF3).

In a further embodiment the method provides the additional step of cultivating the identified plant.

In a further embodiment the method provides the additional step of breeding from the identified plant.

Methods for Breeding Plants with at Least One Dwarfing Associated Phenotype

In a further aspect the invention provides a method for producing a plant with at least one dwarfing-associated phenotype, the method comprising crossing one of:
 a) a plant of the invention,
 b) a plant produced by a method of the invention, and
 c) a plant selected by a method of the invention,
with another plant, wherein the off-spring produced by the crossing is a plant with at least one dwarfing-associated phenotype.

In one embodiment dwarfing-associated phenotype is selected from those described above.

Method Using Plant of the Invention

In a further embodiment the invention provides a method of producing a plant with at least one dwarfing-associated phenotype selected from:
 a) altered auxin transport,
 b) slower auxin transport,
 c) reduced apical dominance,
 d) an altered xylem/phloem ratio,
 e) an increased number of phloem elements,
 f) smaller phloem elements,
 g) thicker bark,
 h) a bushier habit, i) reduced root mass,
j) reduced vigour,
k) less vegetative growth,
l) earlier termination of shoot growth,
m) earlier competence to flower,
n) precocity,
o) earlier phase change,
p) smaller canopy,
q) reduced stem circumference,
r) reduced branch diameter,
s) fewer sylleptic branches,
t) shorter sylleptic branches,
u) more axillary flowers,
v) an earlier teminating primary axis,
w) earlier teminating secondary axes,
x) shorter intenode length,
y) reduced scion mass, the method comprising grafting a scion onto a plant of the invention, a plant produced by a method of the invention, or a plant selected by a method of the invention.

In one embodiment the dwarfing-associated phenotype is at least one of a) to h) and j) to x).

In this embodiment the at least one dwarfing associated phenotype is preferably exhibited in the grafted scion.

In this embodiment the grafted scion preferably exhibits at least one of j) to y). Alternatively, the grafted scion preferably exhibits at least one of j) to x).

In a further embodiment the grafted scion preferably exhibits at least one of reduced vigour, less vegetative growth, earlier termination of shoot growth, a smaller canopy, reduced stem circumference, and reduced scion mass in a scion grafted on to the plant.

In a further embodiment the grafted scion preferably exhibits at least one of reduced vigour, less vegetative growth, earlier termination of shoot growth, a smaller canopy, and reduced stem circumference, in a scion grafted on to the plant.

BRIEF DESCRIPTION OF THE FIGURES

FIG. 1a) Using a bulked segregant analysis, a major dwarfing locus (Dw1) from 'M9' was identified at the top of linkage group (LG) 5. The markers flanking Dw1 were NZraAM18-700 (developed by Plant & Food Research, not publically available) and CH03a09 (publically available). FIG. 1b) A multi-trait QTL analysis identified Dw1 as having a very strong influence on rootstock induced dwarfing. The markers flanking Dw1 are Hi01c04a and CH03a09.

FIG. 2a) Markers flanking our Dw1 are shown in red and extend from 4.72 Mb to 7.62 Mb. FIG. 2b) Markers flanking the Fazio et al Dw1 are shown in green. The distal marker CH05b06z is not mapped. FIG. 2c) The proximal marker CH05b06z maps elsewhere, and the distal most maps incorrectly. FIG. 2d) The distal marker C3843 does not map to LG5. Based on the markers that do map, this would place the Fazio et al Dw1 more distal than ours.

FIG. 3 shows recombinant Dwarf & Semi-Dwarf individuals narrow the genomic interval containing Dw1 to <1.1 Mb. Parents and progeny are listed along the left most column, phenotypes in the next column over, each the remaining columns are genotypes for genetic markers sequentially ordered along LG5. Pink indicates the 'M9' allele and green the 'R5' allele. Individuals highlighted in yellow are recombinant over the interval. Only dwarfed (D) and semi-dwarfed (SD) individuals are informative, as some intermediate (I) and vigorous (V) individuals carry Dw1.

FIG. 9 shows a table demonstrating % similarity between ARF 3 proteins. Proteins were aligned using MUSCLE and the phylogenetic tree used to generate this table was constructed with PHYML, using JTT substitution model and 1,000 bootstrap interations

FIG. 18a) A rootstock QTL affecting scion flowering, shoot growth and TCA (Trunk Cross-sectional Area) was detected on LG5, in the same position as Dw1. One major difference between the two QTLs, the pear QTL controlling early flowering is on the same position, but on the other chromosome, ie derived from the other parent. An HRM marker detecting the ARF3 SNP in apple was screened over the pear population. In FIG. 18b (panels b-d, individuals scored as "AA" were statistically different than siblings scored as "AB" for b) flowering, c) primary axis growth and d) TCA. *=p value<0.001, very significant.

DETAILED DESCRIPTION OF THE INVENTION

Figure 1A:
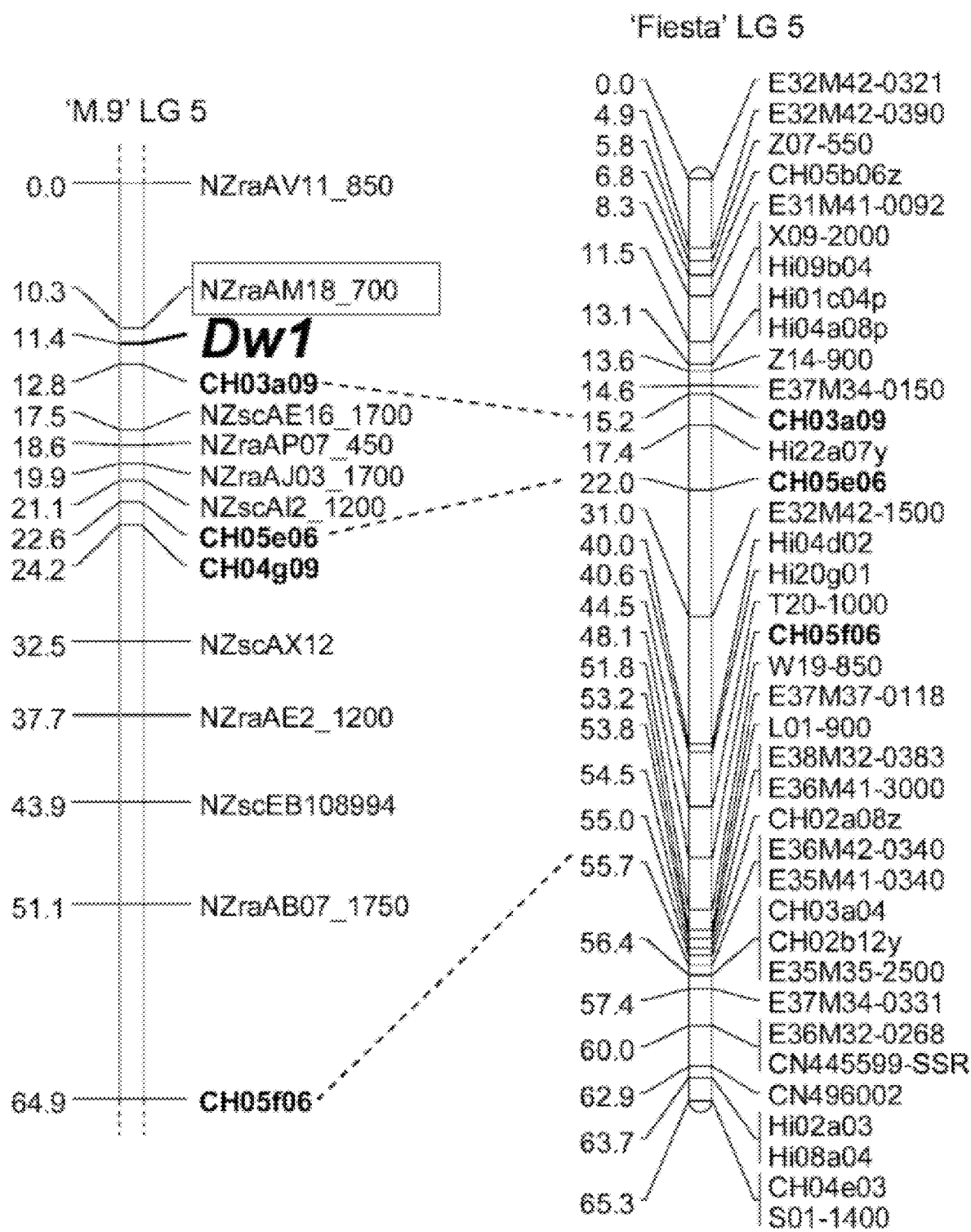
FIGS. 1a-1b show identification of the rootstock dwarfing loci, Dw1.

The present invention provides methods and materials useful for producing or selecting plants with at least one dwarfing associated phenotype.

The dwarfing-associated phenotype may be exhibited in the plant produced or selected, or may be exhibited in scions grafted onto the plants used as root stock, as indicated in Table 1 below.

TABLE 1

| Dwarfing-associated phenotypes found in dwarfing rootstock plants | Dwarfing-associated phenotypes found in scions grafted onto dwarfing rootstock plants |
| --- | --- |
| bushier | reduced vigour |
| altered auxin transport | less vegetative growth |
| altered xylem/phloem ratio | earlier termination of shoot growth |
| more phloem elements | earlier competency to flower |
| smaller phloem elements | precocity |
| thicker bark | earlier phase change |
| slower auxin transport | smaller canopy |
| reduced apical dominance | reduced stem circumference |
| reduced root mass | reduced branch diameter |
|  | fewer sylleptic branches |
|  | shorter sylleptic branches |
|  | more axillary flowers |
|  | earlier terminating primary axis |
|  | earlier terminating secondary axes |
|  | reduced branching density |
|  | reduced internode length |
|  | reduced scion mass |

The dwarfing-associated phenotype may be selected from:
 a) altered auxin transport,
 b) slower auxin transport,
 c) reduced apical dominance,
 d) an altered xylem/phloem ratio,
 e) an increased number of phloem elements,
 f) smaller phloem elements,
 g) thicker bark,
 h) a bushier habit,
 i) reduced root mass,
 j) reduced vigour,
 k) less vegetative growth,
 l) earlier termination of shoot growth,
 m) earlier competence to flower,
 n) precocity,
 o) earlier phase change,
 p) smaller canopy,
 q) reduced stem circumference,
 r) reduced branch diameter,
 s) fewer sylleptic branches,
 t) shorter sylleptic branches,
 u) more axillary flowers,
 v) an earlier terminating primary axis,
 w) earlier terminating secondary axes,
 x) shorter internode length, and
 y) reduced scion mass.

In one embodiment the plant exhibits at least 2, more preferably at least 3, more preferably at least 4, more preferably at least 5, more preferably at least 6, more preferably at least 7, more preferably at least 8, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20, more preferably at least 21, more preferably at least 22, more preferably all 23 of dwarfing associated phenotypes a) to w).

In a further embodiment the plant exhibits at least one of dwarfing associated phenotypes selected from a) to i). In one embodiment the plant exhibits at least 2, more preferably at least 3, more preferably at least 4, more preferably at least 5, more preferably at least 6, more preferably at least 7, more preferably at least 8, of dwarfing associated phenotypes a) to i). In one embodiment this a plant is suitable for use as a root stock.

The dwarfing-associated phenotype may also be the capacity to induce at least one of a) to y) in a scion grafted onto the plant. In a further embodiment the dwarfing-associated phenotype may also be the capacity to induce at least one of a) to y) in a scion grafted onto the plant.

The dwarfing-associated phenotypes are relative terms. In one embodiment the dwarfing associated phenotype is relative to that of a control plant.

The control plant may be any plant of the same type that is not transformed with the polynucleotide, or construct, of the invention of the invention, or used in a method of the invention. The control plant may also be transformed with an "empty" vector, wherein the empty vector does not include an insert sequence corresponding to a polynucleotide of the invention or used in a method of the invention.

For the selection methods the control plant may be a non-selected plant.

The phrases "altered auxin transport" and "slower auxin transport" means that auxin transport in the plant of the invention, or in a method of the invention, is altered or slower relative to that in a control plant. Auxin transport may be measured by methods known to those skilled in the art and explified for example in (Ulmasov, Murfett et al. 1997; Ljung, Hull et al. 2005)

The phrase "apical dominance" is the phenomenon whereby the primary shoot axis suppresses outgrowth of axillary brances. Apical dominance may be assessed by methods known to those skilled in the art for example (Napoli, Beveridge et al. 1999; Shimizu-Sato and Mori 2001; Sussex and Kerk 2001; Bennett, Sieberer et al. 2006)

The phrases "an altered xylem/phloem ratio", "an increased number of phloem elements" and "smaller phloem elements" are known to those skilled in the art, and may be assessed microscopically, as described in the present Examples section (Ruzin 1999).

The phrase "thicker bark" is intended to take the standard meaning, known to those skilled in the art. Thickness of bark can be assessed by taking transverse sections, using histological stains such as safranin/fast green to distinguish xylem from phloem and observing under a microscope (Ruzin 1999).

Bushiness of habit is a term well understood and easily assessed visually by those skilled in the art.

The phrase "reduced vigour" means a reduction in the number of metamers intintiated by extension growth units, resulting in fewer branches, shorter branches and shorter main axis (Costes and Guedon 2002; Seleznyova, Thorp et al. 2003).

The phrase "metamer" means the repeating unit of leaf, axillary meristem, node, and internode (Steeves and Sussex 1989).

The phrase "extension growth unit" means a vegetative shoot with internode expansion (Seleznyova, Thorp et al. 2003).

The phrase "less vegetative growth" means a higher proportion of floral buds relative to vegetative shoots.

The phrase "earlier termination of shoot growth" means a vegetative extension shoot that stops initiating new metamers earlier in the season, resulting in a shorter shoot (Böhlenius, Huang et al. 2006; Hsu, Adams et al. 2011).

The phrase "earlier competence to flower" means the ability of the plant to respond to flowering cues and begin floral development (Hsu, Liu et al. 2006).

The phrase "precocity" means a reduced period in which a plant is unable to begin floral development (Imamura, Nakatsuka et al. 2011).

The phrase "earlier phase change" means the same as "precocious", a plant that is able to respond to floral cues and begin floral development before others of the same age (Huijser and Schmid 2011; Willmann and Poethig 2011).

The phrase "smaller canopy" is a phrase well understood and easily assessed by those skilled in the art.

The phrase "stem circumference" can be easily assessed by those skilled in the art.

Measurement of stem circumference can be replaced by measurement of "Trunk Cross-sectional Area" (TCA). TCA of a grafted scion is generally measured 20 cm above the graft union for grafted trees. For non-tree plants the primary stem is measured in place of the trunk.

"Branch diameter" is a term well understood and easily assessed by those skilled in the art.

The term "sylleptic branches" means a vegetative bud that grows out without a dormancy period, i.e. in the same season it was initiated (Costes and Guedon 1997).

Number and length of sylleptic branches can be easily assessed by those skilled in the art.

The term "axillary flowers" means flowers that are flowers that form directly from an axillary meristem, as opposed to a "fruiting spur" (Fulford 1966).

The term "fruiting spur" means a very short shoot with very condensed internodes that terminates in a bud containing several leaves and an inflorescence" (Fulford 1966).

The phrase "an earlier teminating primary axis means a tree with a shorter primary axis, comprised of fewer nodes.

The phrase "earlier teminating secondary axes" means shorter branches comprised of fewer nodes.

The term "internode" is intended to take its standard meaning. Internode length can be easily assessed by those skilled in the art (Steeves and Sussex 1989).

Cells

In one embodiment the cell is a prokaryotic cell.

In a further embodiment the cell is a eukaryotic cell.

In one embodiment the cell is selected from a bacterial cell, a yeast cell, a fungal cell, an insect cell, algal cell, and a plant cell. In one embodiment the cell is a bacterial cell. In a further embodiment the cell is a yeast cell. In one embodiment the yeast cell is a *S. ceriviseae* cell. In further embodiment the cell is a fungal cell. In further embodiment the cell is an insect cell. In further embodiment the cell is an algal cell.

In a preferred embodiment the cell is a plant cell.

Plants

Plants or plant cells or the invention, or used in the methods of the invention, or used to source naturally occurring ARF3 sequences, may be from any species.

In one embodiment the plant cell or plant, is or is derived from a gymnosperm plant species.

In a further embodiment the plant cell or plant, is or is derived from an angiosperm plant species.

In a further embodiment the plant cell or plant, is or is derived from a from dicotyledonous plant species.

In a further embodiment the plant cell or plant, is or is derived from a monocotyledonous plant species.

Preferred plants in which to introduce dwarfing associated phenotypes include those from any species that produces fruit.

Preferred plants from which to source naturally occurring ARF3 sequences include those from any species that produces fruit.

Preferred fruit producing plants include apple, avocado, pear, peach, cherry, plum, kiwifruit, grape, mango, and orange plants.

A preferred apple genus is *Malus*.

Preferred apple species include: *Malus angustifolia, Malus asiatica, Malus baccata, Malus coronaria, Malus doumeri, Malus florentina, Malus floribunda, Malus fusca, Malus halliana, Malus honanensis, Malus hupehensis, Malus ioensis, Malus kansuensis, Malus mandshurica, Malus micromalus, Malus niedzwetzkyana, Malus ombrophilia, Malus orientalis, Malus prattii, Malus prunifolia, Malus pumila, Malus sargentii, Malus sieboldii, Malus sieversii, Malus sylvestris, Malus toringoides, Malus transitoria, Malus trilobata, Malus tschonoskii, Malus x domestica, Malus x domestica x Malus sieversii, Malus x domestica x Pyrus communis, Malus xiaojinensis, and Malus yunnanensis.*

A particularly preferred apple species is *Malus x domestica*.

A preferred pear genus is *Pyrus*.

Preferred pear species include: *Pyrus calleryana, Pyrus caucasica, Pyrus communis, Pyrus elaeagrifolia, Pyrus hybrid cultivar, Pyrus pyrifolia, Pyrus salicifolia, Pyrus ussuriensis* and *Pyrus x bretschneideri*.

A particularly preferred pear species are *Pyrus communis* and Asian pear *Pyrus x bretschneideri*.

A preferred avocado genus is *Persea*.

Preferred avacado species include *Persea americana* and *Persea gratissima*.

A preferred peach genus is *Prunus*.

Preferred peach species include: *Prunus africana, Prunus apetala, Prunus arborea, Prunus armeniaca, Prunus avium, Prunus bifrons, Prunus buergeriana, Prunus campanulata, Prunus canescens, Prunus cerasifera, Prunus cerasoides, Prunus cerasus, Prunus ceylanica, Prunus cocomilia, Prunus cornuta, Prunus crassifolia, Prunus davidiana, Prunus domestica, Prunus dulcis, Prunus fruticosa, Prunus geniculata, Prunus glandulosa, Prunus gracilis, Prunus grayana, Prunus incana, Prunus incisa, Prunus jacquemontii, Prunus japonica, Prunus korshinskyi, Prunus kotschyi, Prunus laurocerasus, Prunus laxinervis, Prunus lusitanica, Prunus maackii, Prunus mahaleb, Prunus mandshurica, Prunus maximowiczii, Prunus minutiflora, Prunus mume, Prunus murrayana, Prunus myrtifolia, Prunus nipponica, Prunus occidentalis, Prunus padus, Prunus persica, Prunus pleuradenia, Prunus pseudocerasus, Prunus prostrata, Prunus salicina, Prunus sargentii, Prunus scoparia, Prunus serrula, Prunus serrulata, Prunus sibirica, Prunus simonii, Prunus sogdiana, Prunus speciosa, Prunus spinosa, Prunus spinulosa, Prunus ssiori, Prunus subhirtella, Prunus tenella, Prunus tomentosa, Prunus triloba, Prunus turneriana, Prunus ursina, Prunus vachuschtii, Prunus verecunda, Prunus x yedoensis, Prunus zippeliana, Prunus alabamensis, Prunus alleghaniensis, Prunus americana, Prunus andersonii, Prunus angustifolia, Prunus brigantina, Prunus buxifolia, Prunus caroliniana, Prunus cuthbertii, Prunus emarginata, Prunus eremophila, Prunus fasciculata, Prunus fremontii, Prunus geniculata, Prunus gentryi, Prunus havardii, Prunus hortulana, Prunus huantensis, Prunus ilicifolia, Prunus integrifolia, Prunus maritima, Prunus mexicana, Prunus munsoniana, Prunus nigra, Prunus pensylvanica, Prunus pumila, Prunus rigida, Prunus rivularis, Prunus serotina, Prunus sphaerocarpa, Prunus subcordata, Prunus texana, Prunus umbellate* and *Prunus virginiana*.

A particularly preferred peach species is *Prunus persica*.

A preferred kiwifruit genus is *Actinidia*.

Preferred kiwifruit species include: *Actinidia arguta, Actinidia arisanensis, Actinidia callosa, Actinidia carnosifolia, Actinidia chengkouensis, Actinidia chinensis, Actinidia chrysantha, Actinidia cinerascens, Actinidia cordifolia, Actinidia coriacea, Actinidia cylindrica, Actinidia deliciosa, Actinidia eriantha, Actinidia farinosa, Actinidia fasciculoides, Actinidia fortunatii, Actinidia foveolata, Actinidia fulvicoma, Actinidia glauco-callosa-callosa, Actinidia glaucophylla, Actinidia globosa, Actinidia gracilis, Actinidia grandiflora, Actinidia hemsleyana, Actinidia henryi, Actinidia holotricha, Actinidia hubeiensis, Actinidia indochinensis, Actinidia kolomikta, Actinidia laevissima, Actinidia lanceolata, Actinidia latifolia, Actinidia leptophylla, Actinidia liangguangensis, Actinidia lijiangensis, Actinidia linguiensis, Actinidia longicarpa, Actinidia macrosperma, Actinidia maloides, Actinidia melanandra, Actinidia melliana, Actinidia obovata, Actinidia oregonensis, Actinidia persicina, Actinidia pilosula, Actinidia polygama, Actinidia purpurea, Actinidia rongshuiensis, Actinidia rubricaulis, Actinidia rubus, Actinidia rudis, Actinidia rufa, Actinidia rufotricha, Actinidia sabiaefolia, Actinidia sorbifolia, Actinidia stellato-pilosa-pilosa, Actinidia styracifolia, Actinidia suberifolia, Actinidia tetramera, Actinidia trichogyna, Actinidia ulmifolia, Actinidia umbelloides, Actinidia valvata, Actinidia venosa, Actinidia vitifolia* and *Actinidia zhejiangensis*.

Particularly preferred kiwifruit species are *Actinidia arguta, Actinidia chinensis* and *Actinidia deliciosa*.

A preferred orange genus is Citrus.

Preferred orange species include: *Citrus aurantiifolia, Citrus crenatifolia, Citrus maxima, Citrus medica, Citrus reticulata, Citrus trifoliata,* Australian limes *Citrus australasica, Citrus australis, Citrus glauca, Citrus garrawayae, Citrus gracilis, Citrus inodora, Citrus warburgiana, Citrus wintersii, Citrus japonica, Citrus indica* and *Citrus xsinensis*.

Particularly preferred orange species are: *Citrus maxima, Citrus reticulate, Citrus x sinensis*.

A preferred grape genus is *Vitis*.

Preferred grape species include: *Vitis vinifera, Vitis labrusca, Vitis riparia, Vitis aestivalis, Vitis rotundifolia, Vitis rupestris, Vitis coignetiae, Vitis amurensis, Vitis vulpine*.

A particularly preferred grape species is *Vitis vinifera*.

A preferred avocado genus is *Persea*.

Preferred avacado species include *Persea americana* and *Persea gratissima*.

A preferred mango genus is *Mangifera*.

Preferred mango species include: *Mangifera foetida* and *Mangifera indica*.

A particularly preferred grape species is *Mangifera indica*.

A preferred plum genus is *Prunus*.

Preferred plum species include: *P. cerasifera, P. cocomilia, P. consociiflora, P. domestica, P. domestica* ssp. *insititia, P. simonii, P. spinosa, P. alleghaniensis, P. americana, P. angustifolia, P. hortulana, P. maritima, P. mexicana, P. nigra,* and *P. subcordata*.

A particularly preferred plum species is *Prunus domestica*.

Plant Parts, Propagues and Progeny

The term "plant part" or grammatical equivalents thereof is intended to include any part of a plant, a tissue, an organ, a seed, a fruit, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting progeny, comprising the polynucleotides or constructs of the invention, and/or expressing the ARF3 sequences of the invention, also form an part of the present invention.

Preferably the plants, plant parts, propagules and progeny comprise a polynucleotide or construct of the invention, and/or express a ARF3 sequence of the invention.

Marker Assisted Selection

Marker assisted selection (MAS) is an approach that is often used to identify plants that possess a particular trait using a genetic marker, or markers, associated with that trait. MAS may allow breeders to identify and select plants at a young age and is particularly valuable for fruit traits that are hard to measure at a young stage. The best markers for MAS are the causal mutations, but where these are not available, a marker that is in strong linkage disequilibrium with the causal mutation can also be used. Such information can be used to accelerate genetic gain, or reduce trait measurement costs, and thereby has utility in commercial breeding programs.

Methods for marker assisted selection are well known to those skilled in the art, for example: (Collard, B. C. Y. and D. J. Mackill, *Marker-assisted selection: an approach for precision plant breeding in the twenty-first century*. Philosophical Transactions of the Royal Society B-Biological Sciences, 2008. 363(1491): p. 557-572.)

Markers

Markers for use in the methods of the invention may include nucleic acid markers, such as single nucleotide polymorphisms (SNPs), simple sequence repeats (SSRs or microsatellites), insertions, substitutions, indels and deletions.

Preferably the marker is in linkage disequilibrium (LD) with the trait.

Preferably the marker is in LD with the trait at a D' value of at least 0.1, more preferably at least 0.2, more preferably at least 0.3, more preferably at least 0.4, more preferably at least 0.5.

Preferably the marker is in LD with the trait at a $R^2$ value of at least 0.05, more preferably at least 0.075, more preferably at least 0.1, more preferably at least 0.2, more preferably at least 0.3, more preferably at least 0.4, more preferably at least 0.5.

The term "linkage disequilibrium" or LD as used herein, refers to a derived statistical measure of the strength of the association or co-occurrence of two independent genetic markers. Various statistical methods can be used to summarize linkage disequilibrium (LD) between two markers but in practice only two, termed D' and $R^2$, are widely used.

Markers linked, and or in LD, with the trait may be of any type including but not limited to, SNPs, substitutions, insertions, deletions, indels, simple sequence repeats (SSRs).

In the present invention, markers are associated with
a) altered expression of at least one ARF3 polypeptide,
b) altered expression of at least one ARF3 polynucleotide,
c) altered activity of at least one ARF3 polypeptide, One marker associated with altered activity of at least one ARF3 polypeptide identified by the applicant is the presence of a hydrophobic amino acid residue at a position corresponding the amino acid residue 72 in SEQ ID NO:1 (MdARF3).

In one embodiment, the hydrophobic amino acid residue is a Leucine residue.

Thus, in one embodiment, the invention the method involves identifying presence of a Leucine residue at a position corresponding the amino acid residue 72 in SEQ ID NO:1 (MdARF3).

A further marker associated with altered activity of at least one ARF3 polypeptide identified by the applicant is the presence of a codon encoding the Leucine residue.

In one embodiment the codon is found at a position corresponding to nucleotides 214 to 216 in the ARF3 polynucleotide of SEQ ID NO:12.

In one embodiment the codon is selected from: TTA, TTG, CTT, CTC, CTA and CTG.

In a preferred embodiment the codon is TTG.

Thus in a preferred embodiment, the marker is a T nucleotide at a position corresponding to nucleotide 215 in the ARF3 polynucleotide of SEQ ID NO:12.

This marker defines the M9 allele of ARF3.

Other Markers Linked to the M9 Allele of ARF3.

It would be most desirable to identify the presence of the M9 allele of ARF3 discussed above when selecting for at least one dwarfing associated phenotype. However, following the applicants present disclosure, those skilled in the art would know that it would also be possible to select for at least one dwarfing associated phenotype by identifying the presence of a marker linked to the M9 allele of ARF3. Selection methods utilising such linked markers also form part of the present invention. Methods for identify such linked markers are known to those skilled in the art.

Two other preferred markers for use in the marker assisted selection methods of the invention are Hi01c04 and Hi04a08.

The applicants have now shown that these are the closest markers defining the Dw1 QTL interval.

Hi01c04

Hi01c04 is an SSR marker. Suitable primers for amplifying the Hi01c04 marker (and hybridising to the flanking sequences) are shown below.

```
Hi01c04 foward primer:
                                    (SEQ ID NO: 30)
5'-GCTGCCGTTGACGTTAGAG-3'.

Hi01c04 reverse primer:
                                    (SEQ ID NO: 31)
5'-GTTTGTAGAAGTGGCGTTTGAGG-3'.
```

The variable region between the flanking sequences is defined by the formula $(CTC)_n$ The whole sequence of the Hi01c04 is shown in SEQ ID NO:26

Hi04a08

Hi04a08 is also an SSR marker. Suitable primers for amplifying the Hi04a08 marker (and hybridising to the flanking sequences) are shown below.

```
Hi04a08 foward primer:
                                    (SEQ ID NO: 32)
5'-TTGAAGGAGTTTCCGGTTTG-3'.

Hi04a08 reverse primer:
                                    (SEQ ID NO: 33)
5'-GTTTCACTCTGTGCTGGATTATGC-3'.
```

The variable region between the flanking sequences is defined by the formula $(CTC)_n$ The whole sequence of the Hi04a08 is shown in SEQ ID NO:27

Methods for Modifying Endogenous Polynucleotides

Some embodiments of the invention involve modifying and endogenous polynucleotide to induce a dwarfing associated phenotype in a plant, or scion grafted onto the plant.

Methods for modifying endogenous genomic DNA sequences in plants are known to those skilled in the art. Such methods may involve the use of sequence-specific nucleases that generate targeted double-stranded DNA breaks in genes of interest. Examples of such methods for use in plants include: zinc finger nucleases (Curtin et al., 2011. Plant Physiol. 156:466-473.; Sander, et al., 2011. Nat. Methods 8:67-69.), transcription activator-like effector nucleases or "TALENs" (Cermak et al., 2011, Nucleic Acids Res. 39:e82; Mahfouz et al., 2011 Proc. Natl. Acad. Sci. USA 108:2623-2628; Li et al., 2012 Nat. Biotechnol. 30:390-392), and LAGLIDADG homing endonucleases, also termed "meganucleases" (Tzfira et al., 2012. Plant Biotechnol. J. 10:373-389).

Targeted genome editing using engineered nucleases such as clustered, regularly interspaced, short palindromic repeat (CRISPR) technology, is an important new approach for generating RNA-guided nucleases, such as Cas9, with customizable specificities. Genome editing mediated by these nucleases has been used to rapidly, easily and efficiently modify endogenous genes in a wide variety of biomedically important cell types and in organisms that have traditionally been challenging to manipulate genetically. A modified version of the CRISPR-Cas9 system has been developed to recruit heterologous domains that can regulate endogenous gene expression or label specific genomic loci in living cells (Nature Biotechnology 32, 347-355 (2014). The system is applicable to plants, and can be used to regulate expression of target genes. (Bortesi and Fischer, Biotechnology Advances Volume 33, Issue 1, January-February 2015, Pages 41-52).

Those skilled in the art will thus appreciate that there are numerous ways in which the expression or activity of MdARF3 can be reduced or eliminated. Any such method is modified within the scope of the invention.

In certain embodiments of the invention, a genome editing technology (e.g. TALENs, a Zinc finger nuclease or CRISPR-Cas9 technology) can be used to modify one or more base pairs in a target ARF3 gene to create a codon encoding a hydrophobic amino acid, such as a Leucine residue at a position corresponding the amino acid residue 72 in SEQ ID NO:1 (MdARF3). This approach effectively creates an M9 type ARF3 allele in the target plant.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides.

The term "primer" refers to a short polynucleotide, usually having a free 3'OH group, that is hybridized to a template and used for priming polymerization of a polynucleotide complementary to the target. The primer may consist of a "fragment" of a polynucleotide as defined herein.

The term "probe" refers to a short polynucleotide that is used to detect a polynucleotide sequence that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques.

A "fragment" of a polypeptide is a subsequence of the polypeptide that in some embodiments performs a function/activity of and/or influences three dimensional structure of the polypeptide.

The term "isolated" as applied to the polynucleotide or polypeptide sequences disclosed herein is used to refer to sequences that are removed from their natural cellular environment. The isolated sequence is preferably separated from the sequences that may be found flanking the sequence in its naturally occurring environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from the NCBI website on the World Wide Web at ftp://ftp.ncbi.nih.gov/blast/. The default parameters of bl2seq are utilized except that filtering of low complexity parts should be turned off.

The identity of polynucleotide sequences may be examined using the following unix command line parameters:

bl2seq-i nucleotideseq1-j nucleotideseq2-F F-p blastn

The parameter-F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from the World Wide Web at http://www.hgmp.mrc.ac.uk/Software/EMBOSS/. The European Bioinformatics Institute server also provides the facility to perform EMBOSS-needle global alignments between two sequences on line at http://www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp://ftp.ncbi.nih.gov/blast/.

The similarity of polynucleotide sequences may be examined using the following unix command line parameters:

bl2seq-i nucleotideseq1-j nucleotideseq2-F F-p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than 1×10−6 more preferably less than 1×10−9, more preferably less than 1×10−12, more preferably less than 1×10−15, more preferably less than 1×10−18, more preferably less than 1×10−21, more preferably less than 1×10−30, more preferably less than 1×10−40, more preferably less than 1×10−50, more preferably less than 1×10−60, more preferably less than 1×10−70, more preferably less than 1×10−80, more preferably less than 1×10−90 and most preferably less than 1×10−100 when compared with any one of the specifically identified sequences.

Alternatively, variant polynucleotides of the present invention, or used in the methods of the invention, hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81. 5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention, or used in the methods of the invention, also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from the NCBI website on the World Wide Web at ftp://ftp.ncbi.nih.gov/blast/via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from the NCBI website on the World Wide Web at ftp://ftp.ncbi.nih.gov/blast/. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

Polypeptide variants of the present invention, or used in the methods of the invention, also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp://ftp.ncbi.nih.gov/blast/. The similarity of polypeptide sequences may be examined using the following unix command line parameters:

bl2seq -i peptideseq1 -j peptideseq2 -F F -p blastp

Variant polypeptide sequences preferably exhibit an E value of less than $1\times10-6$ more preferably less than $1\times10-9$, more preferably less than $1\times10-12$, more preferably less than $1\times10-15$, more preferably less than $1\times10-18$, more preferably less than $1\times10-21$, more preferably less than $1\times10-30$, more preferably less than $1\times10-40$, more preferably less than $1\times10-50$, more preferably less than $1\times10-60$, more preferably less than $1\times10-70$, more preferably less than $1\times10-80$, more preferably less than $1\times10-90$ and most preferably $1\times10-100$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
  a) a promoter functional in the host cell into which the construct will be transformed,
  b) the polynucleotide to be expressed, and
  c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence may, in some cases, identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination, mRNA stability, and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors. Introns within coding sequences can also regulate transcription and influence post-transcriptional processing (including splicing, capping and polyadenylation).

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

In certain embodiments the ARF3 polynucleotides/polypeptides of the invention may be advantageously expressed under the control of selected promoter sequences as described below.

Vegetative Tissue Specific Promoters

An example of a vegetative specific promoter is found in U.S. Pat. Nos. 6,229,067; and 7,629,454; and 7,153,953; and 6,228,643.

Pollen Specific Promoters

An example of a pollen specific promoter is found in U.S. Pat. Nos. 7,141,424; and 5,545,546; and 5,412,085; and 5,086,169; and 7,667,097.

Seed Specific Promoters

An example of a seed specific promoter is found in U.S. Pat. Nos. 6,342,657; and 7,081,565; and 7,405,345; and 7,642,346; and 7,371,928. A preferred seed specific promoter is the napin promoter of *Brassica napus* (Josefsson et al., 1987, J Biol Chem. 262(25):12196-201; Ellerström et al., 1996, Plant Molecular Biology, Volume 32, Issue 6, pp 1019-1027).

Fruit Specific Promoters

An example of a fruit specific promoter is found in U.S. Pat. Nos. 5,536,653; and 6,127,179; and 5,608,150; and 4,943,674.

Non-Photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. No. 5,639,952 and in U.S. Pat. No. 5,656,496.

Root Specific Promoters

An example of a root specific promoter is found in U.S. Pat. No. 5,837,848; and US 2004/0067506 and US 2001/0047525.

Tuber Specific Promoters

An example of a tuber specific promoter is found in U.S. Pat. No. 6,184,443.

Bulb Specific Promoters

An example of a bulb specific promoter is found in Smeets et al., (1997) Plant Physiol. 113:765-771.

Rhizome Preferred Promoters

An example of a rhizome preferred promoter is found Seong Jang et al., (2006) Plant Physiol. 142:1148-1159.

Endosperm Specific Promoters

An example of an endosperm specific promoter is found in U.S. Pat. No. 7,745,697.

Corm Promoters

An example of a promoter capable of driving expression in a corm is found in Schenk et al., (2001) Plant Molecular Biology, 47:399-412.

Photosythetic Tissue Preferred Promoters

Photosythetic tissue preferred promoters include those that are preferentially expressed in photosynthetic tissues of the plants. Photosynthetic tissues of the plant include leaves, stems, shoots and above ground parts of the plant. Photosythetic tissue preferred promoters include light regulated promoters.

Light Regulated Promoters

Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

Transgene

A "transgene" is a polynucleotide that is introduced into an organism by transformation. The transgene may be derived from the same species or from a different species to the organism into which the transgene is introduced. In one embodiment the transgene is a naturally occurring sequence. In a further embodiment the transgene is a non-naturally occurring sequence. The transgene may be synthesized or produced by recombinant methods.

Host Cells

Host cells may be derived from, for example, bacterial, fungal, yeast, insect, mammalian, algal or plant organisms. Host cells may also be synthetic cells. Preferred host cells are eukaryotic cells. A particularly preferred host cell is a plant cell, particularly a plant cell in a tissue of a plant.

A "transgenic plant" refers to a plant which contains new genetic material as a result of genetic manipulation or transformation. The new genetic material may be derived from a plant of the same species as the resulting transgenic plant or from a different species. Subsequent offspring or generations of the plant that still contain the new genetic material are also transgenic plants according to the invention.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman Mass., 1993, Methods Enzymol. 218: 340-56) and hybridization-based method, computer/database—based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, http://www-igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, Guide to Protein Purification,).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens et al., (2000) Plant Mol Biol 42: 819-32, Hellens et al., Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest. In one embodiment the promoter is not normally associated with a transgene of interest. Such a promoter may be described as a heterologous promoter, with respect to the transgene.

The promoters may be derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues respond to internal developmental signals or external abiotic or biotic stresses are described in the scientific literature. Exemplary promoters are described, e.g., in WO 02/00894 and WO2011/053169, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463, 174 and 5,750,871); cereals (U.S. Pat. No. 6,074,877); pear (Matsuda et al., 2005, Plant Cell Rep. 24(1):45-51); *Prunus* (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), Rubus (Graham et al., 1995 Methods Mol Biol. 1995; 44:129-33), tomato (Dan et al., 2006, Plant Cell Reports V25:432-441), apple (Yao et al., 1995, Plant Cell Rep. 14, 407-412), Canola (*Brassica napus* L.). (Cardoza and Stewart, 2006 Methods Mol Biol. 343:257-66), safflower (Orlikowska et al., 1995, Plant Cell Tissue and Organ Culture 40:85-91), ryegrass (Altpeter et al., 2004 Developments in Plant Breeding 11(7):255-250), rice (Christou et al., 1991 Nature Biotech. 9:957-962), maize (Wang et al., 2009 In: Handbook of Maize pp. 609-639) and *Actinidia eriantha* (Wang et al., 2006, Plant Cell Rep. 25, 5: 425-31). Transformation of other species is also contemplated by the invention. Suitable methods and protocols are available in the scientific literature.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. In some embodiments, the term "comprising" (and related terms such as "comprise and "comprises") can be replaced by "consisting of" (and related terms "consist" and "consists").

Example 1: Refining the Genomic Region Containing the Dw1 Loci

Background

Figure 1B:
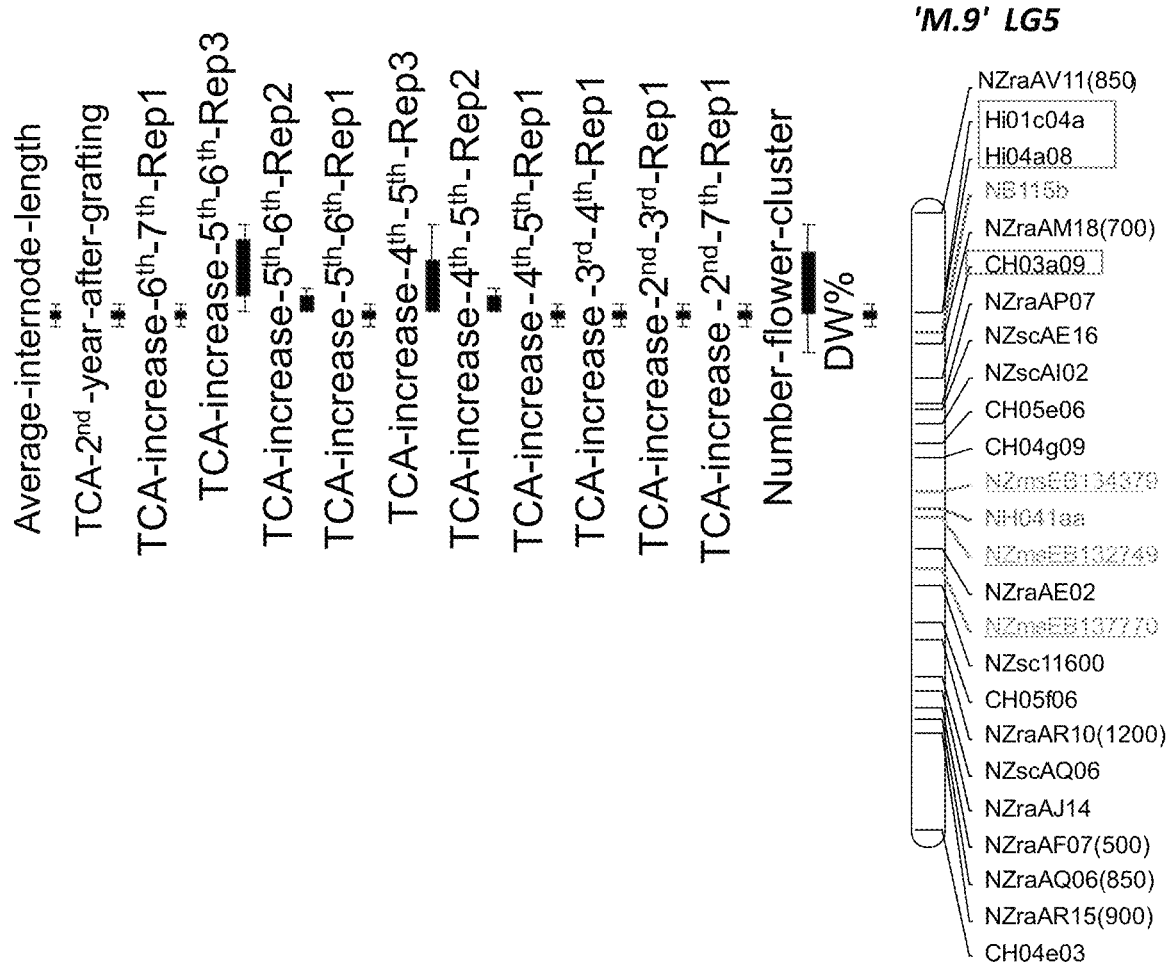
Figure 2A:
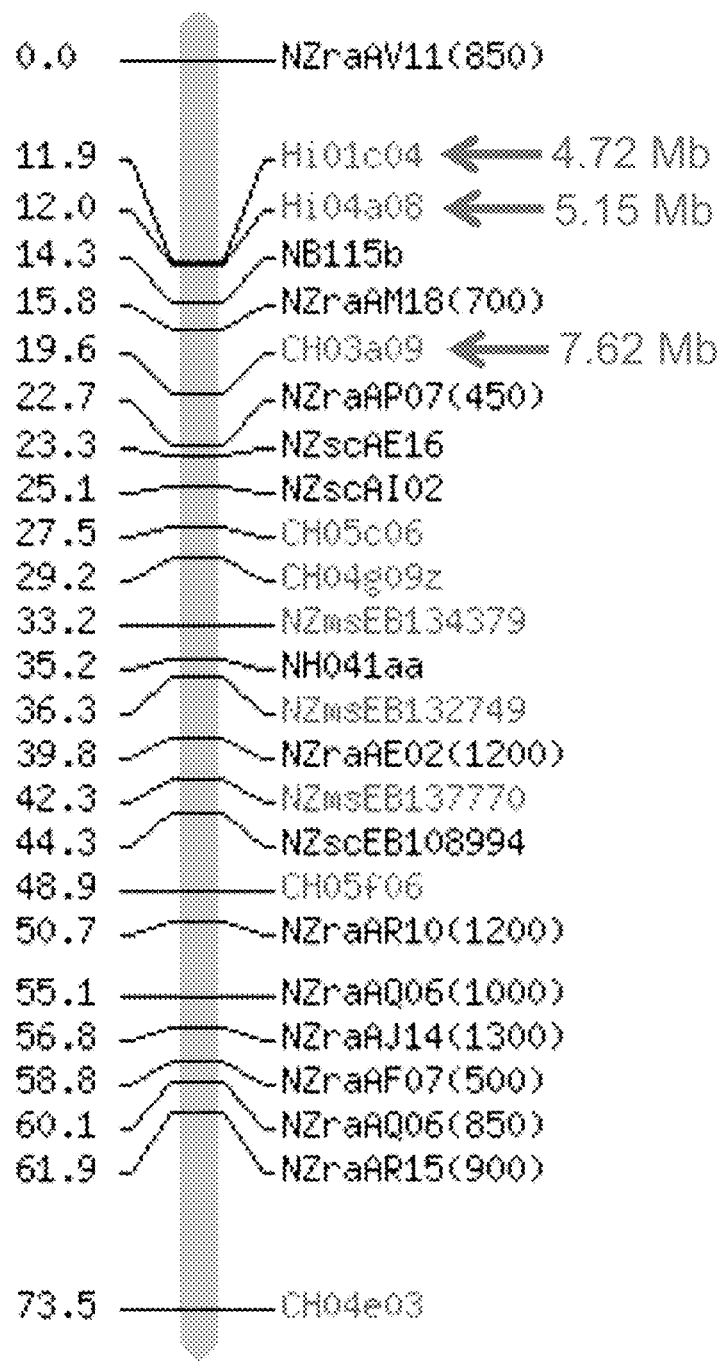
FIGS. 2a-2d show genetic markers flanking o Dw1 according to the applicant, and that described by Fazio et al.
Figure 2B:
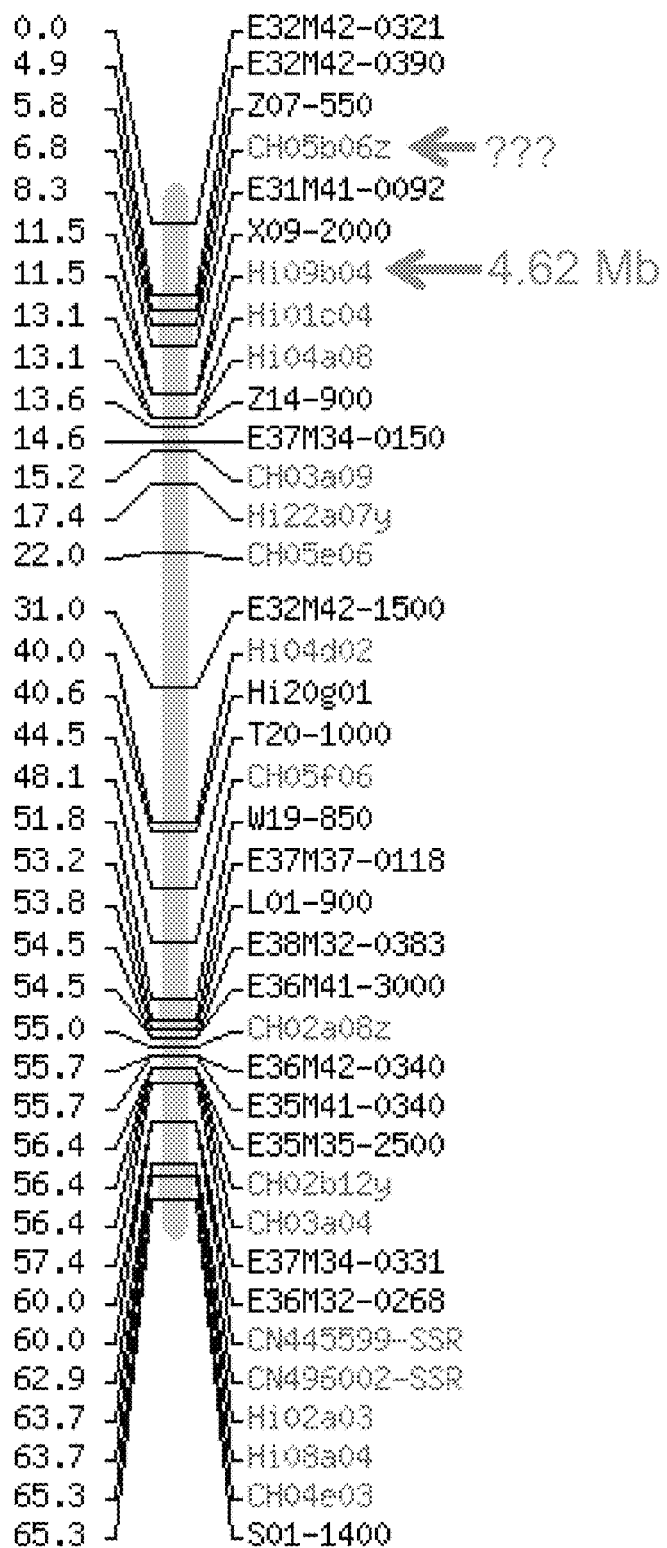
Figure 2C:
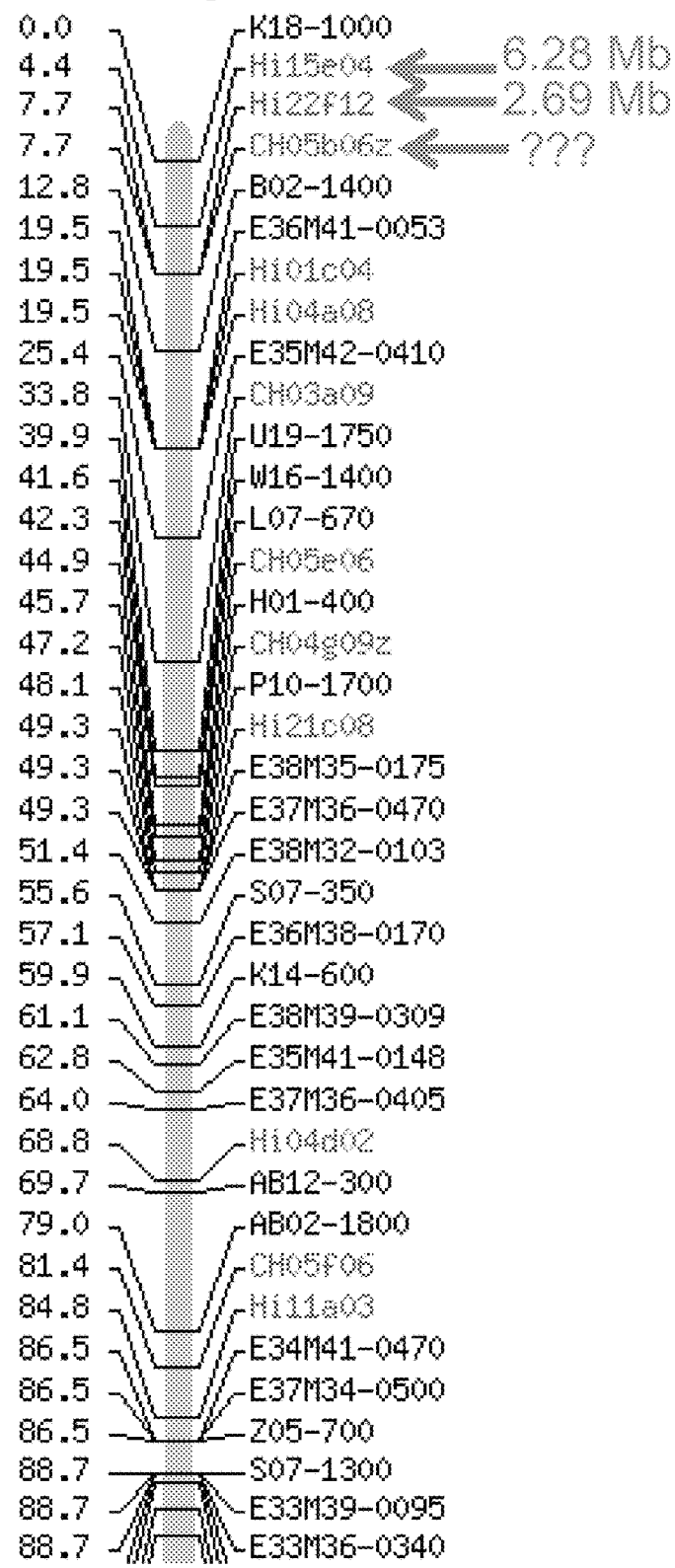
Figure 2D:
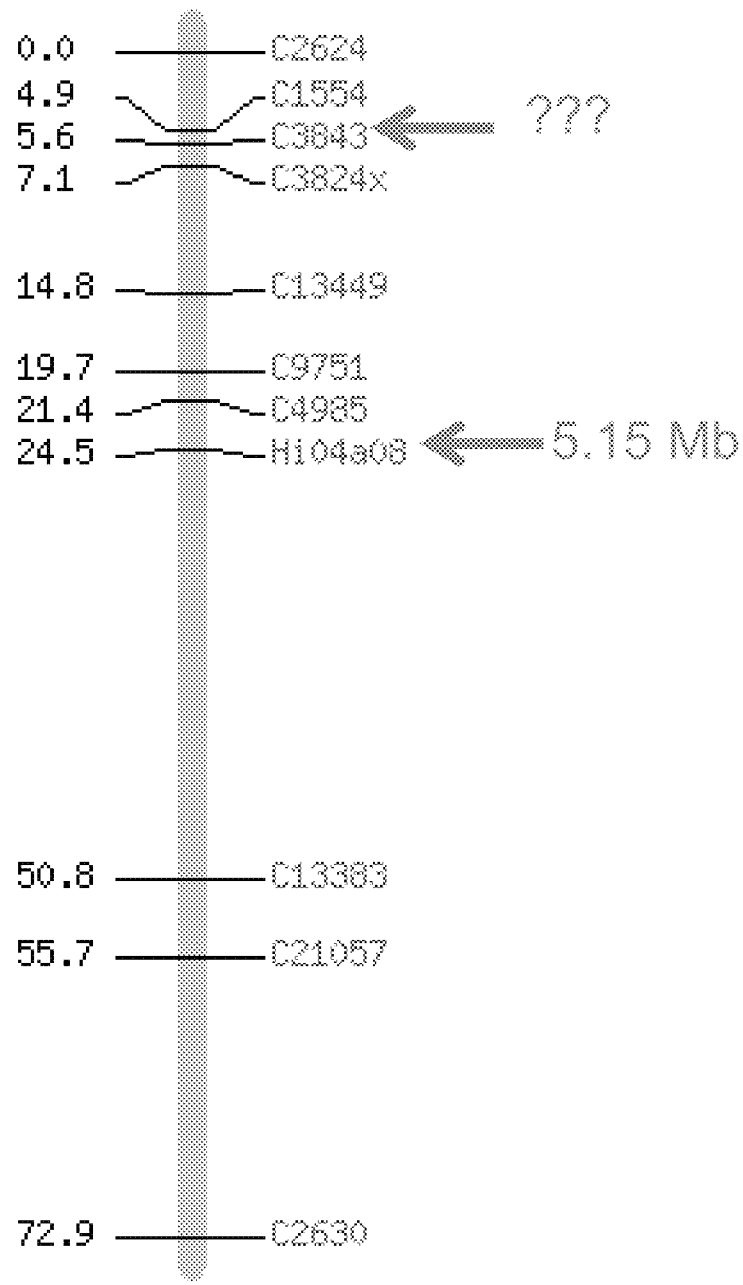

In a previous QTL study, the closest genetic markers that defined Dw1 were Hi01c04 and Ch03a09 (FIG. 1), which are located at 4.72 and 7.62 Mb respectively on the reference golden delicious genome (Celton et al 2009). More recently Fazio and co-workers (Fazio et al 2014) found a more distal position for Dw1, between Hi22f12 (2.69 Mb) and Hi04a08 (5.15 Mb) (FIG. 2).

Figure 3:
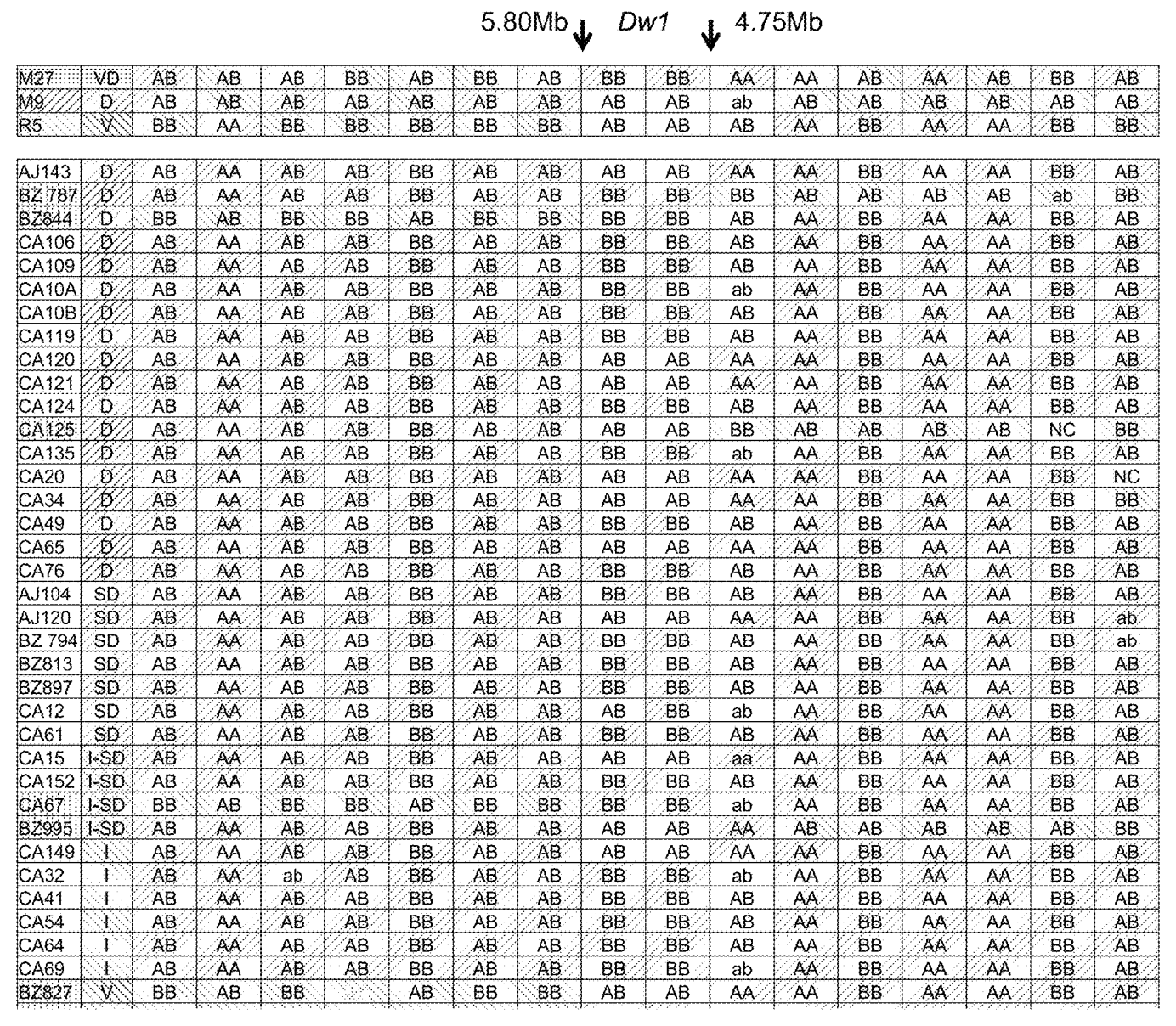

In the present work, the applicants developed genetic markers based on genomic sequence from the interval between 4.5 Mb and 7.2 Mb on linkage group 5 (LG5). By screening these markers over the parents and progeny of their rootstock population, the applicants were able to identify recombinants within this interval (i.e. had a chromosomal cross over between 'M9' and '1R5'). Intermediate and vigorous recombinants were not informative, because some of the individuals carried Dw1. However, all dwarfed and semi-dwarfed individuals carried Dw1, so these recombinants were informative in defining the interval that contains Dw1. Based on four dwarfed and two semi-dwarfed recombinant individuals, the applicants were able to narrow the genomic interval containing Dw1 to a smaller region, between 4.75 Mb and 5.80 Mb (FIG. 3).

This region defines an interval of 1.05 Mb (5.80-4.75 Mb).

BRIEF DESCRIPTION OF THE SEQUENCES

| SEQ ID NO: | Sequence type | Common name | Species | Reference |
|---|---|---|---|---|
| 1 | Polypeptide | Apple | *Malus domestica* | MdARF3 |
| 2 | Polypeptide | Apple | *Malus domestica* | MdARF3 'M9' |
| 3 | Polypeptide | *Arabidopsis* | *Arabidopsis thaliana* | ARF3/ETTIN |
| 4 | Polypeptide | Bean | *Phaseolus vulgaris* | PvARF3 |
| 5 | Polypeptide | Tomato | *Solanum lycopersicum* | SlARF3 |
| 6 | Polypeptide | Mandarin orange | *Citrus clementina* | CcARF3 |
| 7 | Polypeptide | Strawberry | *Frageria vesca* | FvARF3 |
| 8 | Polypeptide | Plum | *Prunus persica* | PpARF3 |
| 9 | Polypeptide | Pear | *Pyrus communis* | PcARF3 |
| 10 | Polypeptide | Poplar | *Populus tremula* | PtARF3 |
| 11 | Polypeptide | Grape | *Vitis vinefera* | VvARF3 |
| 12 | Polynucleotide | Apple | *Malus domestica* | MdARF3 (cDNA) |
| 13 | Polynucleotide | Apple | *Malus domestica* | MdARF3 (gDNA) |
| 14 | Polynucleotide | Apple | *Malus domestica* | MdARF3 'M9'(cDNA) |
| 15 | Polynucleotide | Apple | *Malus domestica* | MdARF3 'M9'(gDNA) |
| 16 | Polynucleotide | *Arabidopsis* | *Arabidopsis thaliana* | ARF3/ETTIN (cDNA) |
| 17 | Polynucleotide | *Arabidopsis* | *Arabidopsis thaliana* | ARF3/ETTIN (gDNA) |
| 18 | Polynucleotide | Bean | *Phaseolus vulgaris* | PvARF3 (cDNA) |
| 19 | Polynucleotide | Tomato | *Lycopersicum esculentum* | LeARF3 (cDNA) |
| 20 | Polynucleotide | Mandarin orange | *Citrus clementina* | CcARF3 (cDNA) |
| 21 | Polynucleotide | Strawberry | *Frageria vesca* | FvARF3 (cDNA) |
| 22 | Polynucleotide | Plum | *Prunus persica* | PpARF3 (cDNA) |
| 23 | Polynucleotide | Pear | *Pyrus communis* | PcARF3 (cDNA) |
| 24 | Polynucleotide | Poplar | *Populus tremula* | PtARF3 (cDNA) |
| 25 | Polynucleotide | Grape | *Vitis vinefera* | VvARF3 (cDNA) |
| 26 | Polynucleotide | Apple | *Malus domestica* | Hi01C04 marker |
| 27 | Polynucleotide | Apple | *Malus domestica* | Hi04A08 marker |

EXAMPLES

The invention will now be illustrated with reference to the following non-limiting examples.

It is not the intention to limit the scope of the invention to the present example only. As would be appreciated by a skilled person in the art, many variations are possible without departing from the scope of the invention.

Although this is a smaller interval, this region could still contain over 100 genes. It is also possible that the genetic determinant of dwarfing at the Dw1 locus would be a micro RNA (mi RNA) or other non-protein encoding gene. Furthermore, prior to the present application, there were no obvious candidate gene/s, or even classes of candidate genes that might be responsible for the dwarfing effect of the Dw1 locus.

Dw1 has a More Significant Effect than Dw2 on Rootstock-Induced Dwarfing

To elucidate the relative contributions of Dw1 and Dw2 to dwarfing of the scion, the applicants examined three of the most robust phenotypes associated with dwarfing, i.e. early flowering (spring of year two), final TCA (year seven), and overall visual assessment (year seven) of scions grafted to rootstocks carrying various combinations of Dw1 and Dw2.

Figure 4:
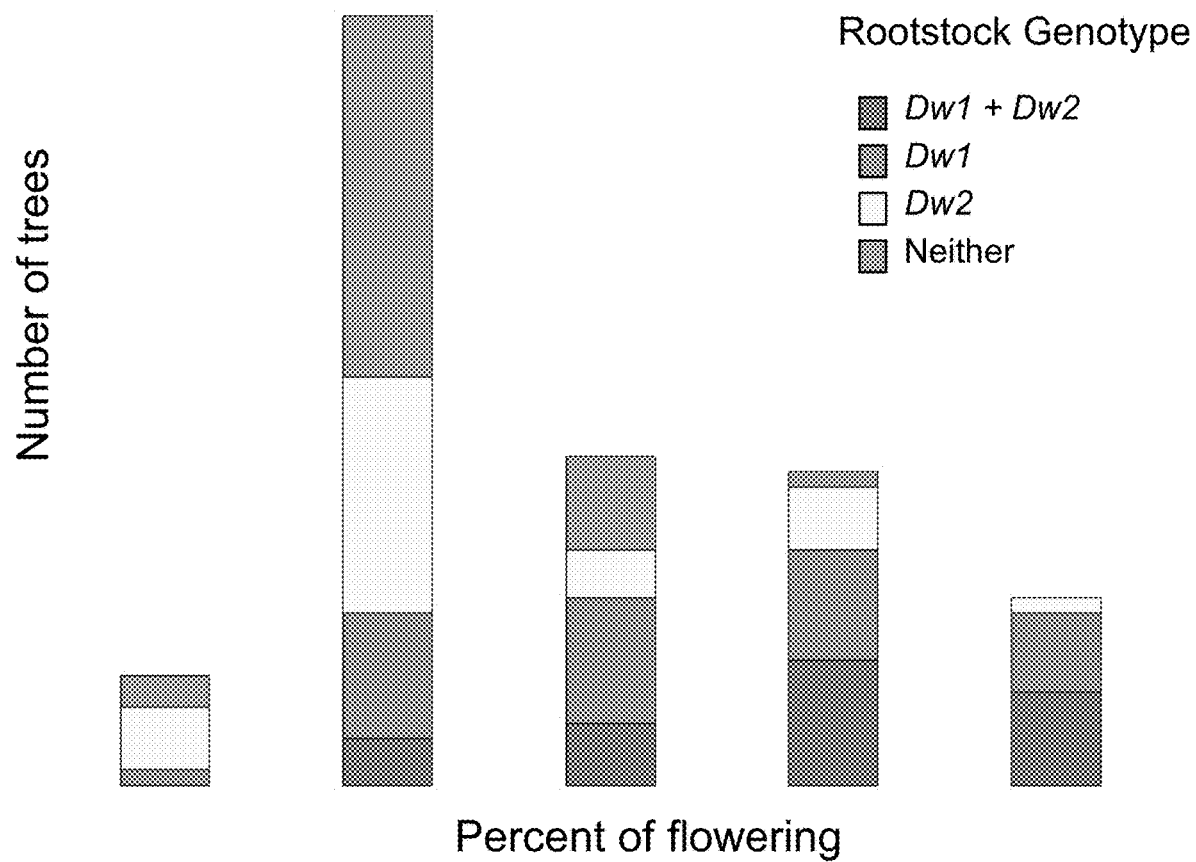
FIG. 4 shows the number of trees in each flowering class and composition of classes by Dw1 and Dw2 genotype. Flowering was assessed by estimating the total number of flower clusters on each tree in the spring of year two, and placing them into quartiles relative to the most highly floral trees, ie, 1%-25%, 26-50%, 51-75%, 76-100%. Trees with no flowers were also recorded. Data is from 109 trees from the first population, replicate 1.

Early flowering was assessed in the spring of year two by estimating the number of floral clusters on 109 trees from the first population. The majority of the trees with the highest degree of flowering had been grafted onto rootstocks carrying both Dw1 and Dw2 (50%), or Dw1 alone (41.7%) (FIG. 4). Conversely, the trees with no flowers or the fewest flowers were predominantly grafted onto rootstocks carrying Dw2 alone (33.9%), or neither dwarfing locus (44.6%).

Figure 5:
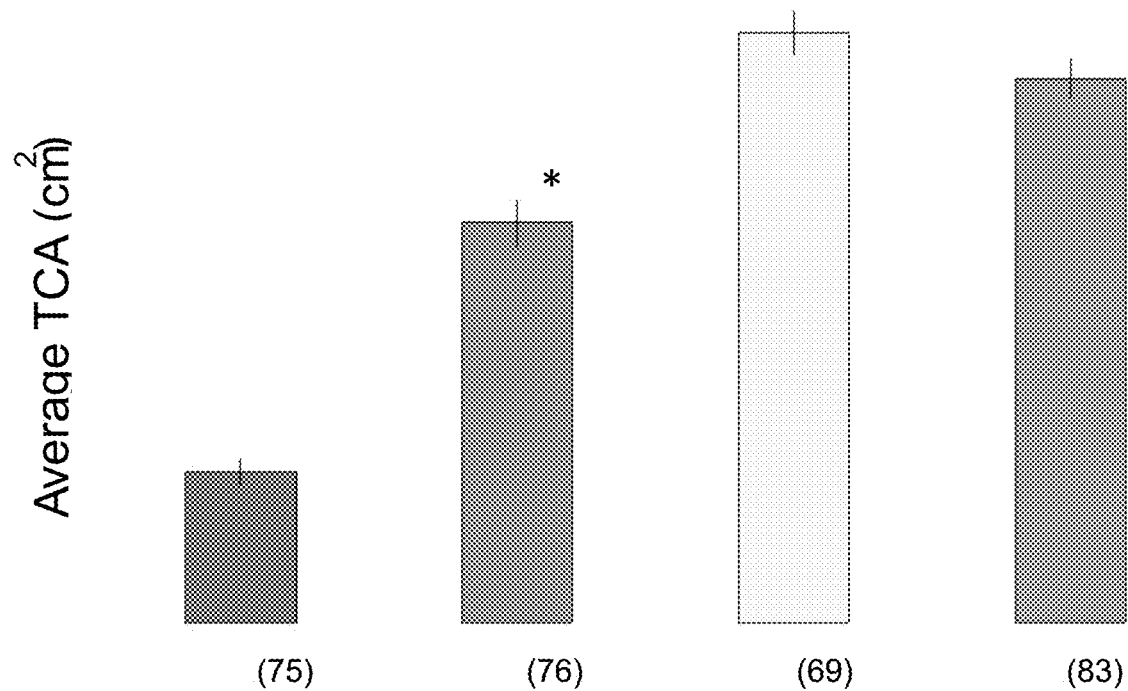
FIG. 5 shows the average year seven TCA of trees in each genotypic class. The number of individuals in each class is given in parentheses, error bars indicate standard error. Average TCAs were compared to the group with neither Dw1 nor Dw2 by ANOVA, asterisks indicate the means are significantly different with a p value of <0.001. Data is from 303 trees from the second population.

After seven years of growth, the TCA of 303 trees from the second population were measured. Trees grafted onto rootstocks carrying both Dw1 and Dw2 exhibited the lowest average TCA, only 23% of that of scions on rootstocks with neither loci. Rootstocks with Dw1 alone reduced scion TCA to 73% of those with neither rootstock loci. Surprisingly, trees grafted onto rootstocks with Dw2 alone had the highest TCA of all (FIG. 5).

Figure 6:
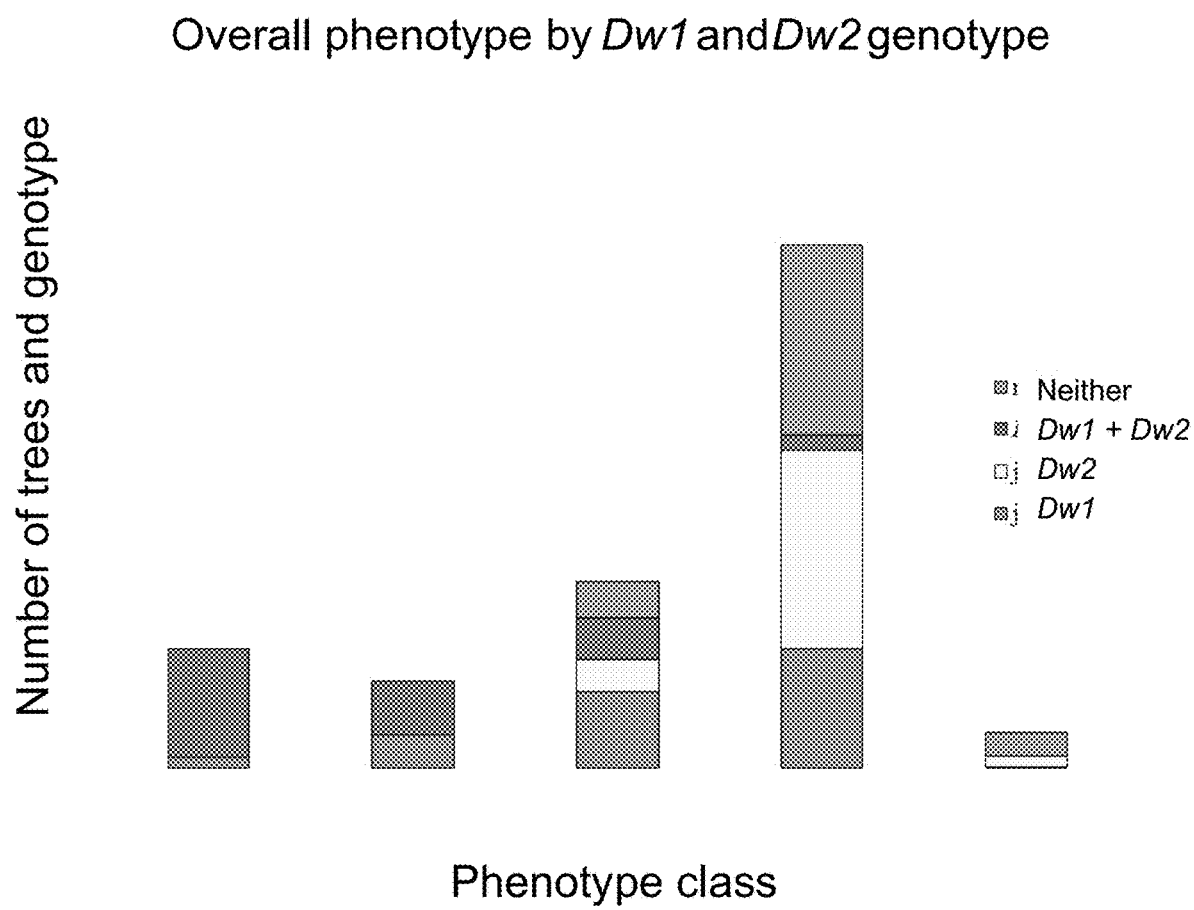
FIG. 6 shows the composition of each phenotypic class by Dw1 and Dw2 genotype. Trees from both populations (449 trees in total) were visually assessed after seven years of growth and placed into one of five phenotypic classes, D=dwarf, SD=semi-dwarf, 1=intermediate, V=vigorous, and VV=very vigorous.

As rootstock-induced dwarfing becomes more pronounced over successive growth cycles, an expert visual assessment of the whole tree phenotype after seven years provided an overall measure of scion vigour. When 449 grafted trees from both populations were compared, a clear trend relating rootstock genotype to phenotypic class was observed. All the dwarfed and semi-dwarfed trees were grafted onto rootstocks with Dw1 and Dw2 or Dw1 alone, whereas the vigorous and very vigorous trees had rootstocks carrying Dw2 alone, Dw1 alone, or neither locus (FIG. 6). Nearly 40% of the vigorous trees were on rootstocks carrying Dw2, indicating that this locus alone is not sufficient to dwarf the scion.

However in contrast to the recent work of Fazio et al (Fazio, Wan et al. 2014) the present study does indicate that the Dw1 loci can influence dwarfing alone (i.e. even in the absence of Dw2).

Other Dwarfing and Semi-Dwarfing Rootstocks Carry Dw1 and Dw2

Figure 17:
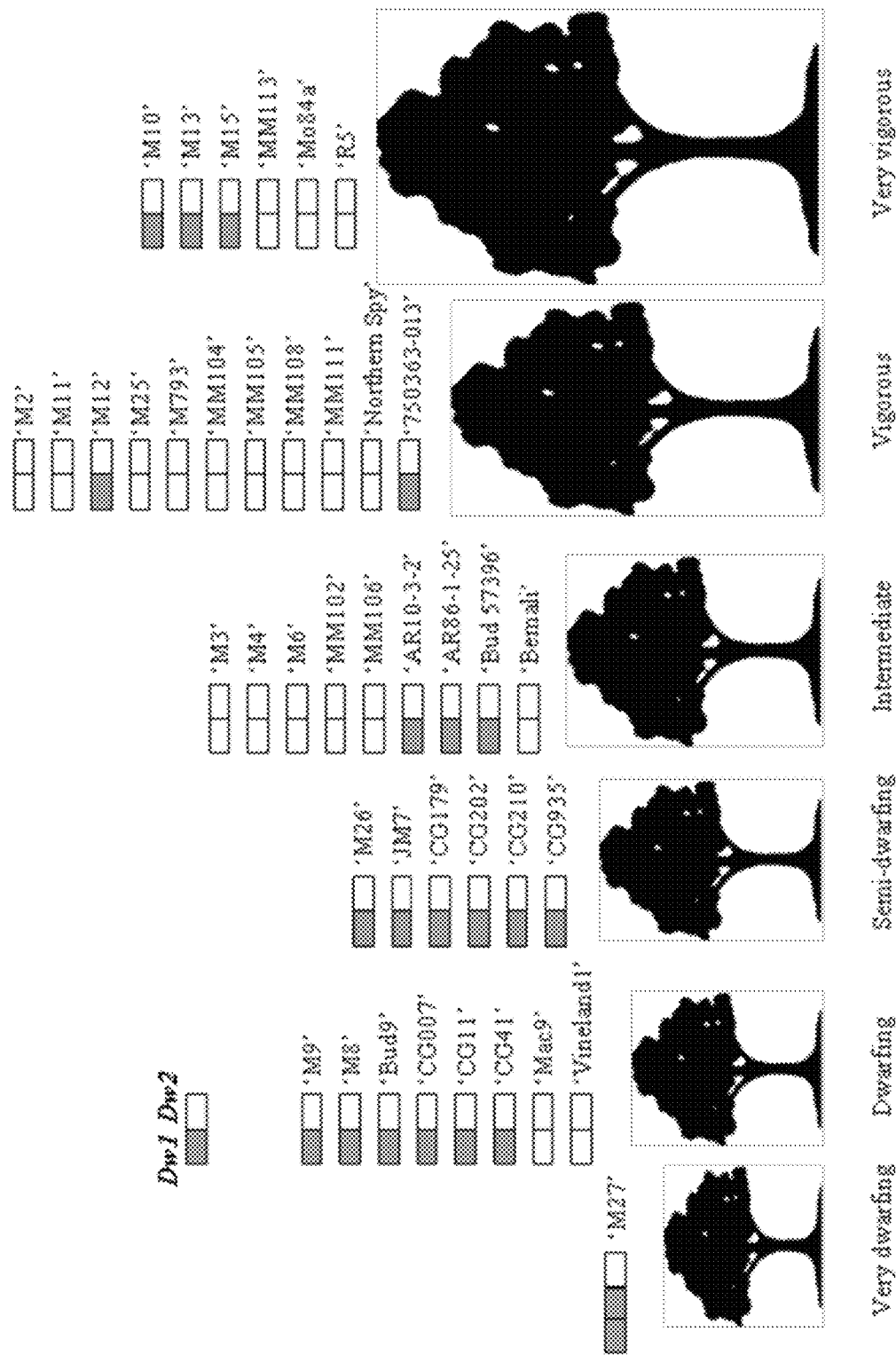
FIG. 17 shows a summary of Dw1 and Dw2 genotyping of rootstock accessions. SSR makers were used to genotype rootstock accessions for the presence of Dw1 and Dw2. A green square indicates the presence of a single allele of Dw1, yellow represents Dw2. The very dwarfing rootstock 'M27' is homozygous for Dw1, suggesting that Dw1 is a semi-dominant mutation.

Genetic markers linked to Dw1 and Dw2 were screened over 41 rootstock accessions that confer a range of effects on scion growth. The majority of dwarfing and semi-dwarfing rootstock accessions screened carried marker alleles linked to both Dw1 and Dw2 (Foster et al, 2015 and FIG. 17). This suggests that most apple dwarfing rootstocks have been derived from the same genetic source.

Example 2: A Pear Rootstock QTL Influencing Scion Size and Flowering

Figure 18A:
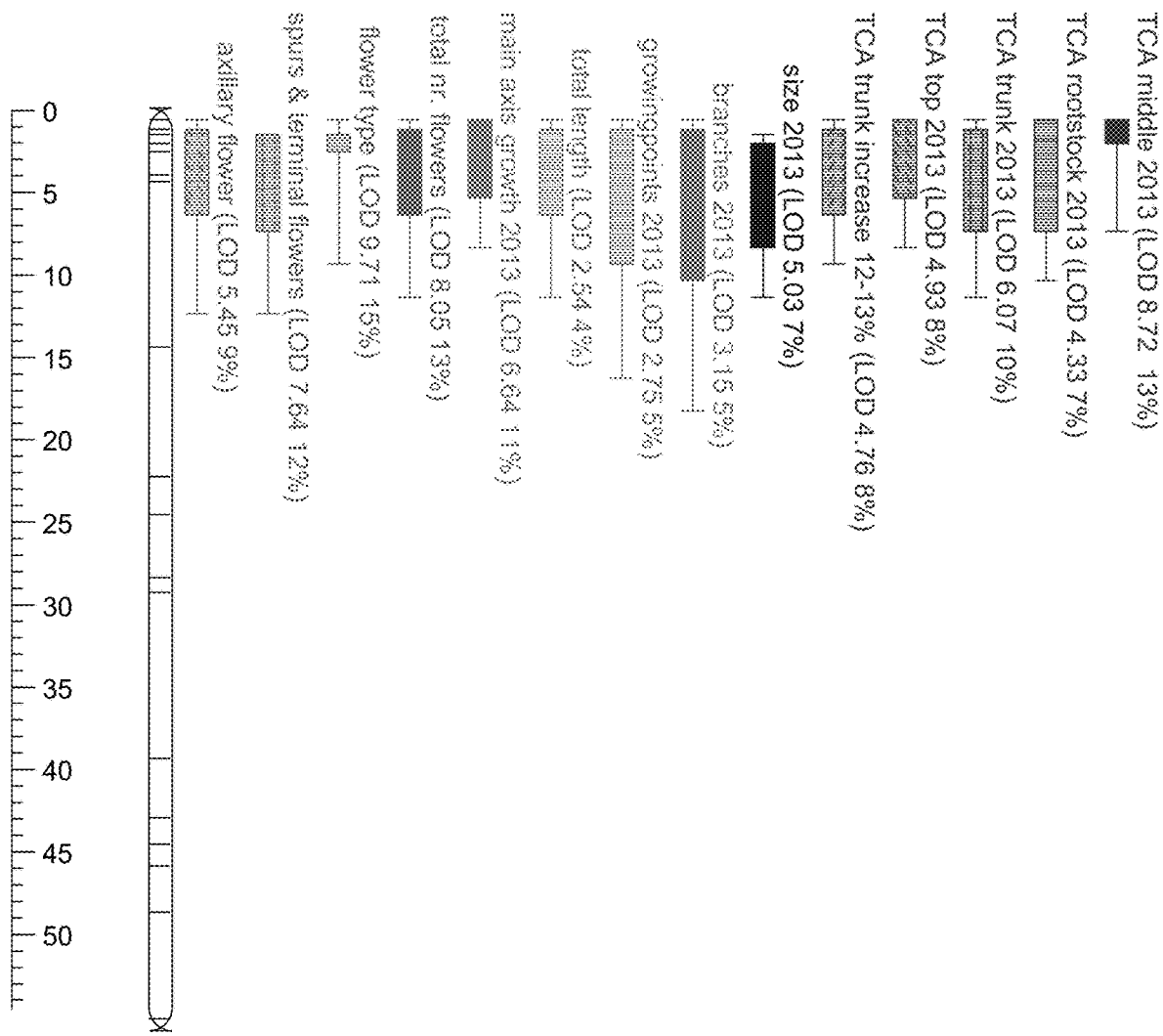
FIGS. 18a-18b show that a pear rootstock QTL maps to the same position as Dw1.
Figure 18B:
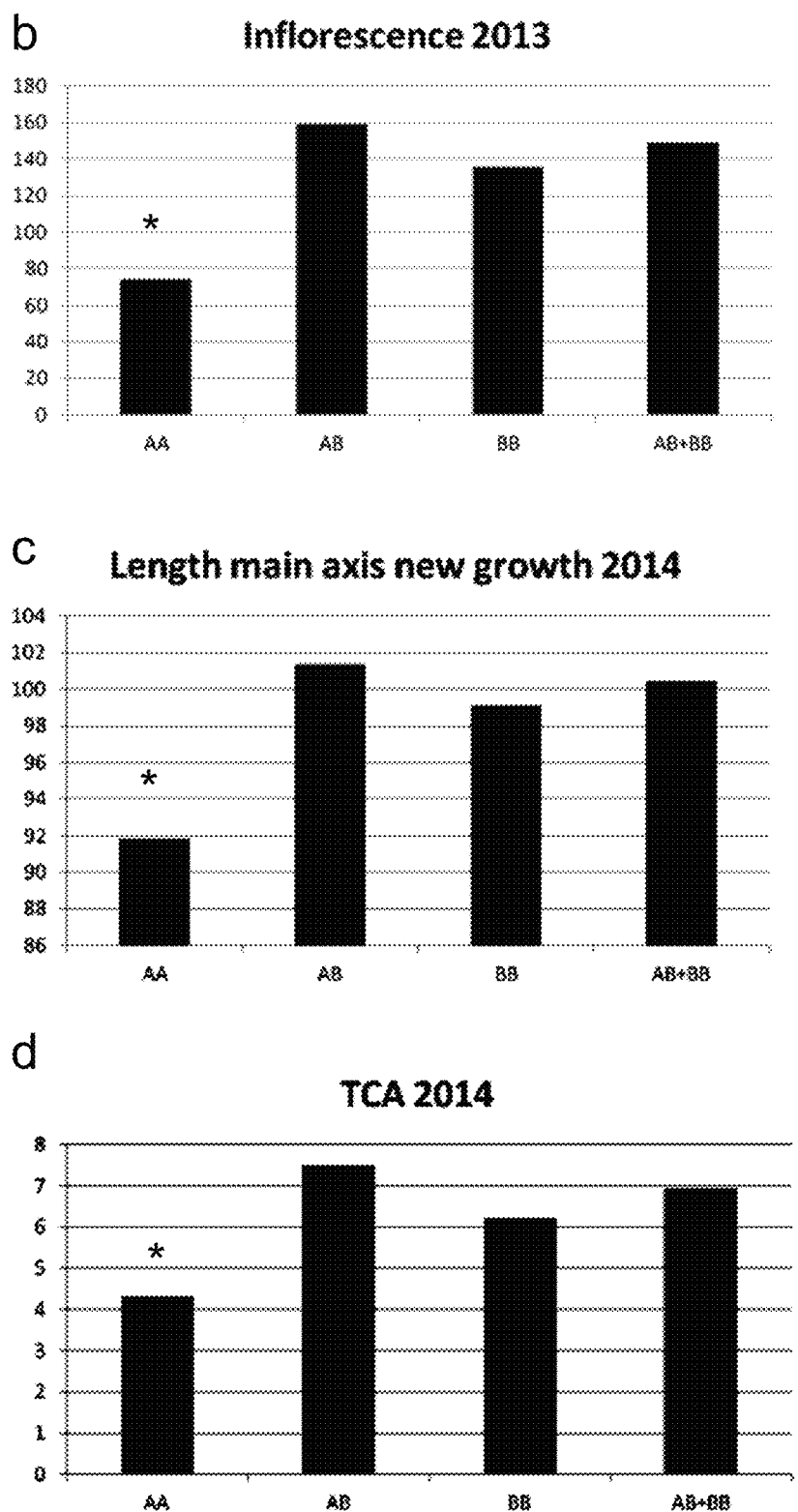
Figure 19:
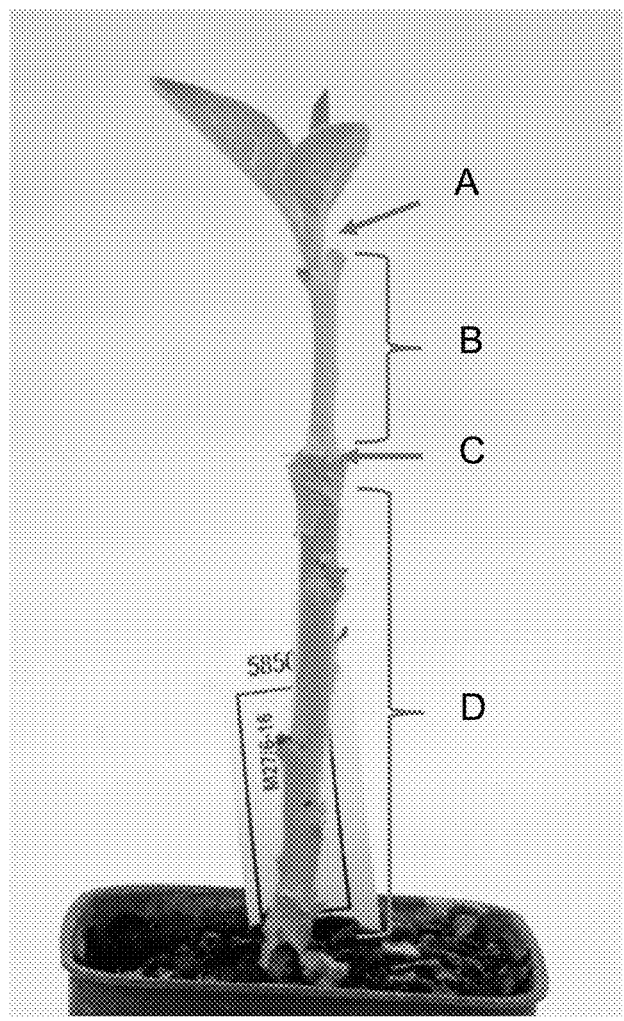
FIG. 19 illustrates a grafting experiment to demonstrate effect on scion. A—illustrates that one apical meristem is allowed to grow out. B—shows the grafted non-transformed wild-type stem. C—shows thwe graft junction. D—shows the "rootstock" which can be 35S:Dw1 (M9 mutant allele), 35S:dw1 (M793 non-dwarf allele) or non-transformed (WT).

Pear does not have a true dwarfing rootstock, such as 'M9', although some rootstocks are known to influence scion size and flowering. A pear segregating rootstock population was generated by crossing 'Old Home' to 'Louis Bon Jersey'. The progeny were grafted with 'Cornice', and scions were phenotyped for 4 years. A QTL influencing scion size and flowering was identified at the top of LG5, in the exact location as Dw1 (FIGS. 18a and 18b, PFR, unpublished). No QTL corresponding to Dw2 was identified. Pear and apple are very closely related and show strong synteny of gene order along their orthologous chromosomes. This finding raises the exciting possibility that Dw1 predates the divergence of apple and pear and that the same gene may be influencing both the apple and pear QTL.

Example 3: Identification of ARF3 as a Candidate Gene for Dw1

The applicants found that there are approximately 168 annotated genes within the 1.1 Mb interval (unpublished). Based on expressed sequence ESTs from the Plant and Food proprietary *Malus* database (Newcomb, Crowhurst et al. 2006) and RNA seq experiments (unpublished), the applicants estimated the number of expressed genes is about 100.

The applicants identified an Auxin Response Factor 3 (ARF3) transcription factor gene present in the refined Dw1 interval, which they showed to be upregulated in M9 rootstock, as a candidate gene for the Dw1 QTL effect.

Many hypotheses to explain the mechanism of dwarfing rootstocks implicate auxin, but the genetic basis of any auxin effect is completely unknown. ARF3 is a member of a large family of Auxin Response Factors, transcription factors that activate or repress downstream genes in response to auxin. ARF3/ETTIN was first discovered as a gene required for normal patterning of floral organs in *Arabidopsis* (Sessions and Zambryski 1995; Sessions, Nemhauser et al. 1997). It was later discovered that ARF3 and the transcription factor KANADI mediate both auxin flow and organ polarity, which includes vascular patterning (Pekker, Alvarez et al. 2005; Izhakia and Bowman 2007; Kelley, Arreola et al. 2012). ARF3 also has a key role in promoting phase change (transition to flowering), increased ARF3 expression leads to earlier flowering, loss of ARF3 function delays flowering. (Fahlgren, Montgomery et al. 2006; Hunter, Willmann et al. 2006).

ARF3 is up-regulated in 'M9' and 'M27' relative to vigorous rootstocks

Figure 7:
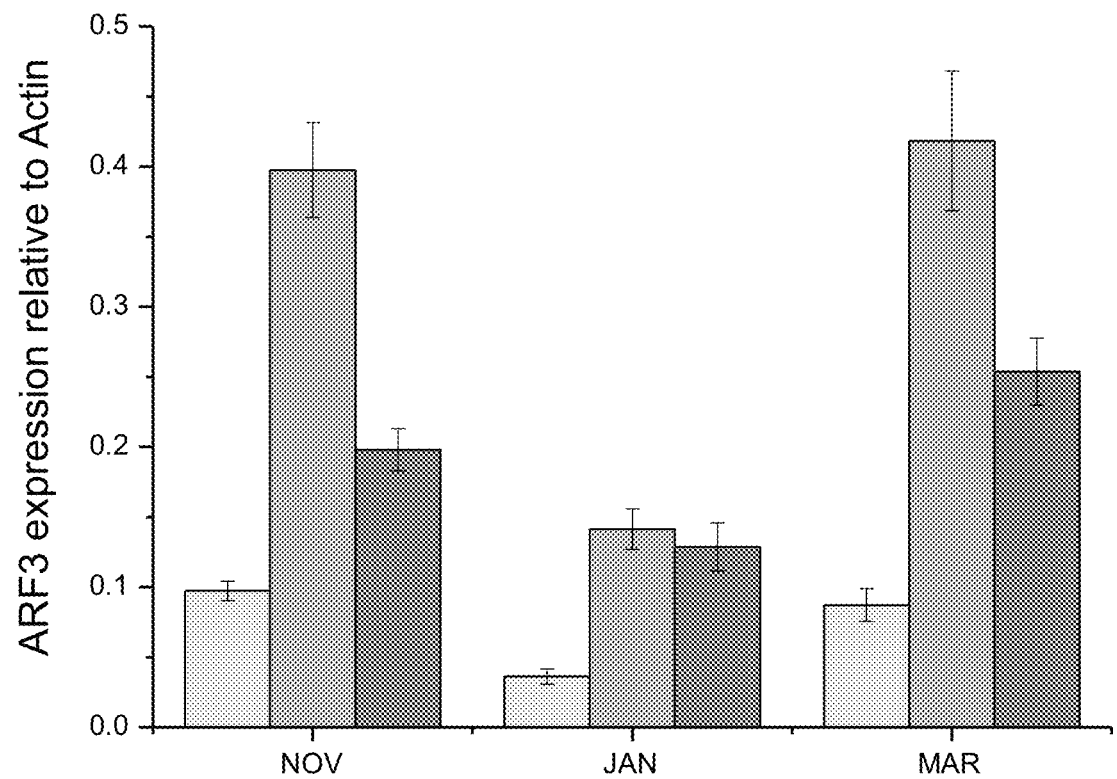
FIG. 7 shows quantitative RT-PCR of ARF3. For each time point, RNA was isolated and analysed from vascular-enriched tissue from 4-6 separate biological replicates of each genotype. Error bars indicate standard error for biological replicates.

The applicants used quantitative real time PCR (qRT-PCR) to compare ARF3 expression in vascular-enriched tissue from 'M9' and another dwarfing rootstock 'M27' with a vigorous rootstock, 'M793' (FIG. 7). ARF3 expression was about four times higher in 'M9' than 'M793' at all time points. In 'M27', ARF3 expression was 2-4 times higher levels than 'M793'.

'M9' has a Mutation in the ARF3 Gene

Figure 8:
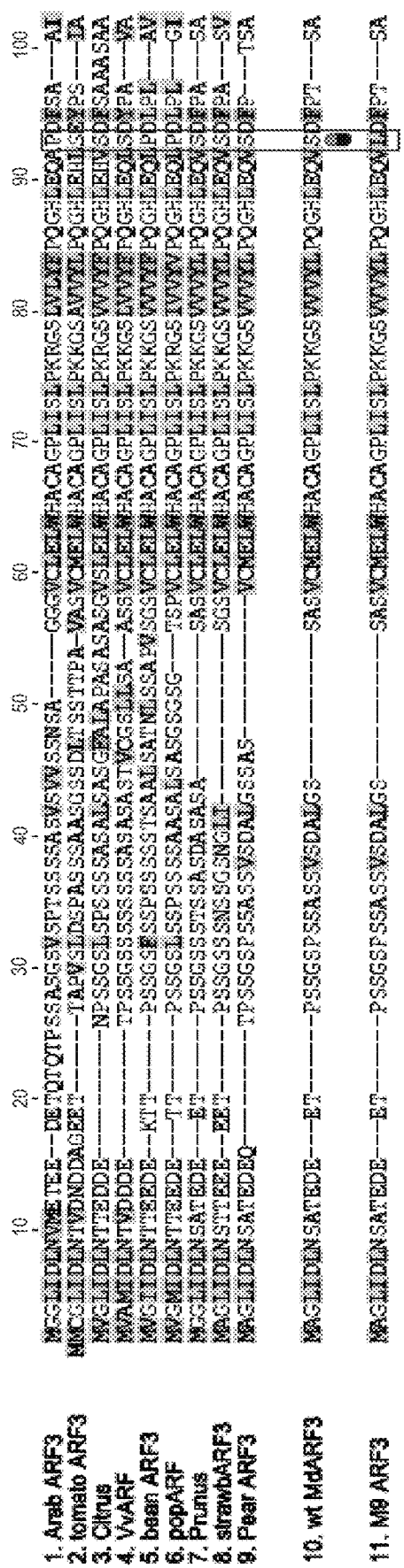
FIG. 8 shows an amino acid line up of ARF3 proteins from plants: Arab ARF3 (amino acids 1-294 of SEQ ID NO: 3), tomato ARF3 (amino acids 1-295 of SEQ ID NO: 5), Citrus (amino acids 1-293 of SEQ ID NO: 6), VvARF (amino acids 1-290 of SEQ ID NO: 11), Bean ARF3 (amino acids 1-293 of SEQ ID NO: 4), popARF (amino acids 1-289 of SEQ ID NO: 10), Prunus (amino acids 1-281 of SEQ ID NO: 8), strawbARF3 (amino acids 1-279 of SEQ ID NO: 7), Pear ARF3 (amino acids 1-280 of SEQ ID NO: 9), wt MdARF3 (amino acids 1-280 of SEQ ID NO: 1), and M9 ARF3 (amino acids 1-280 of SEQ ID NO: 2). ARF3 proteins have a highly conserved B3 DNA binding domain, an auxin response element and a tasi-ARF recognition site. M9' is heterozygous for a non-synonymous SNP that changes a conserved Serine/Proline to a Leucine (indicated by the box).
Figure 8:
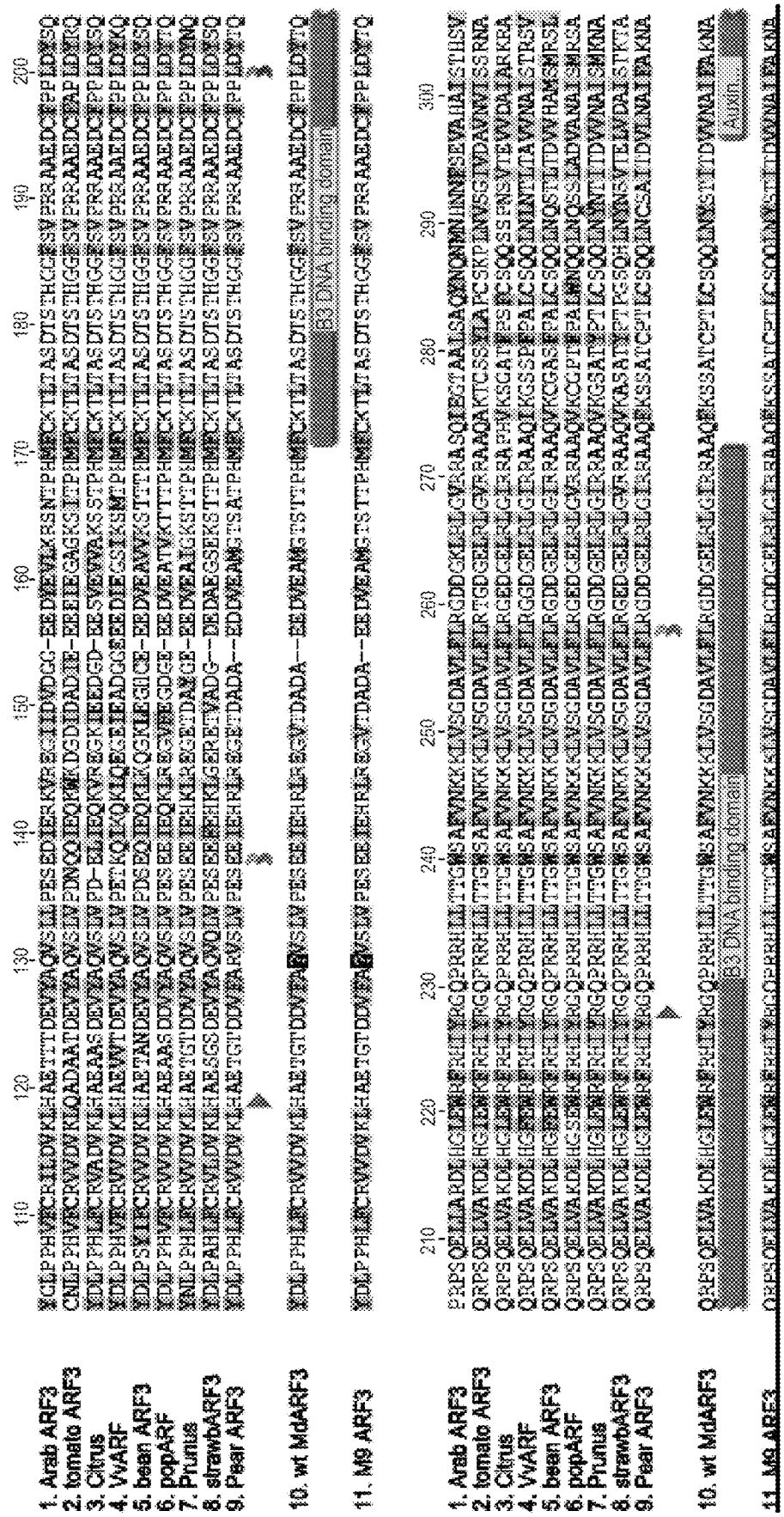

To identify any 'M9'-specific DNA changes that might alter gene expression or function/activity the applicants performed genomic sequencing of 'M9'. This revealed that the 'M9' MdARF3 (MDP000173151) carried a single nucleotide polymorphism (SNP) that changed a conserved Serine to a Leucine. FIG. 8 shows an amino acid line-up with the 'M9', the reference MdARF3 proteins and ARF3 proteins from a variety of plants. This SNP alter the function of the ARF3 protein.

The 'M9' ARF3 SNP as a Genetic Marker in Apple and Pear

To test if the SNP identified in the 'M9' ARF3 segregates with dwarfing individuals, the applicants used primers that amplify the SNP in a High Resolution Melting (HRM) analysis over the entire 'M9'×'R5' rootstock population. The results showed clear segregation of a distinct melting curve with all individuals that were previously identified as having Dw1. The same marker was also tested on the pear rootstock population and showed clear segregation with one curve associated with high flowering individuals, another with low or no flowering trees.

Example 4: Transgenic Expression of ARF3 in Petunia and Tobacco

To test if the higher expression and/or the non-synonymous SNP in the 'M9' ARF3 cause phenotypes associated with dwarfing rootstocks, the applicants made transgenic lines of both tobacco and petunia that over-express either the 'M9' or the reference allele of ARF3. These are hence referred to as M9 ARF3 and wt ARF3 respectively. Petunia and tobacco were chosen as models because they are both amenable to grafting.

Figure 10:
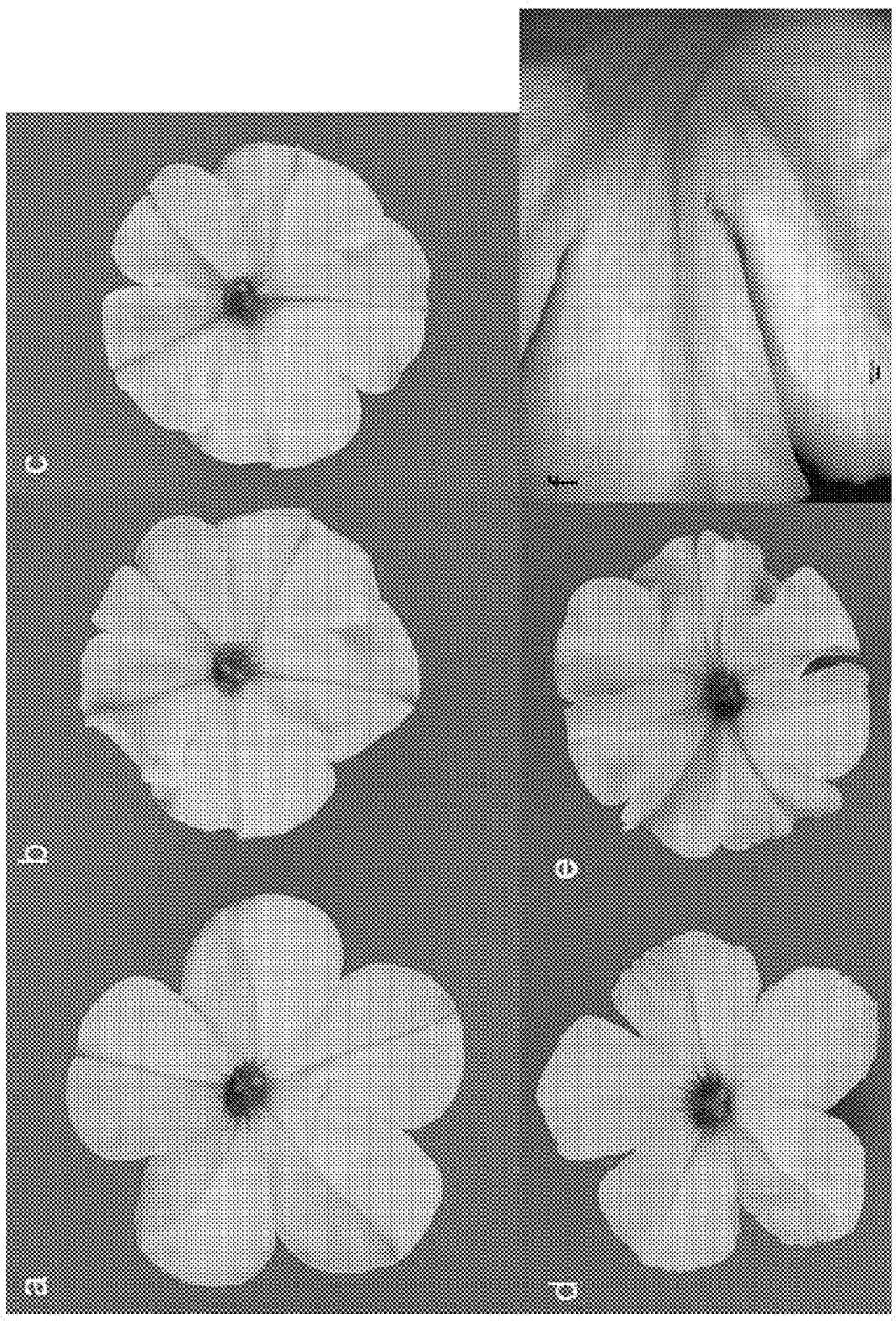
FIG. 10 shows over-expression of 'M9' ARF3 in petunia. a) Non-transformed and b-f) 35S:'M9' ARF3 flowers. Three independent lines showed incomplete petal fusion at the tube (b-c), irregular petal margins (d), and vascular patterning defects (e). (f) shows a close up of the abaxial (outside) of the flower, revealing incomplete petal fusion and vascular patterning defects.
Figure 11:
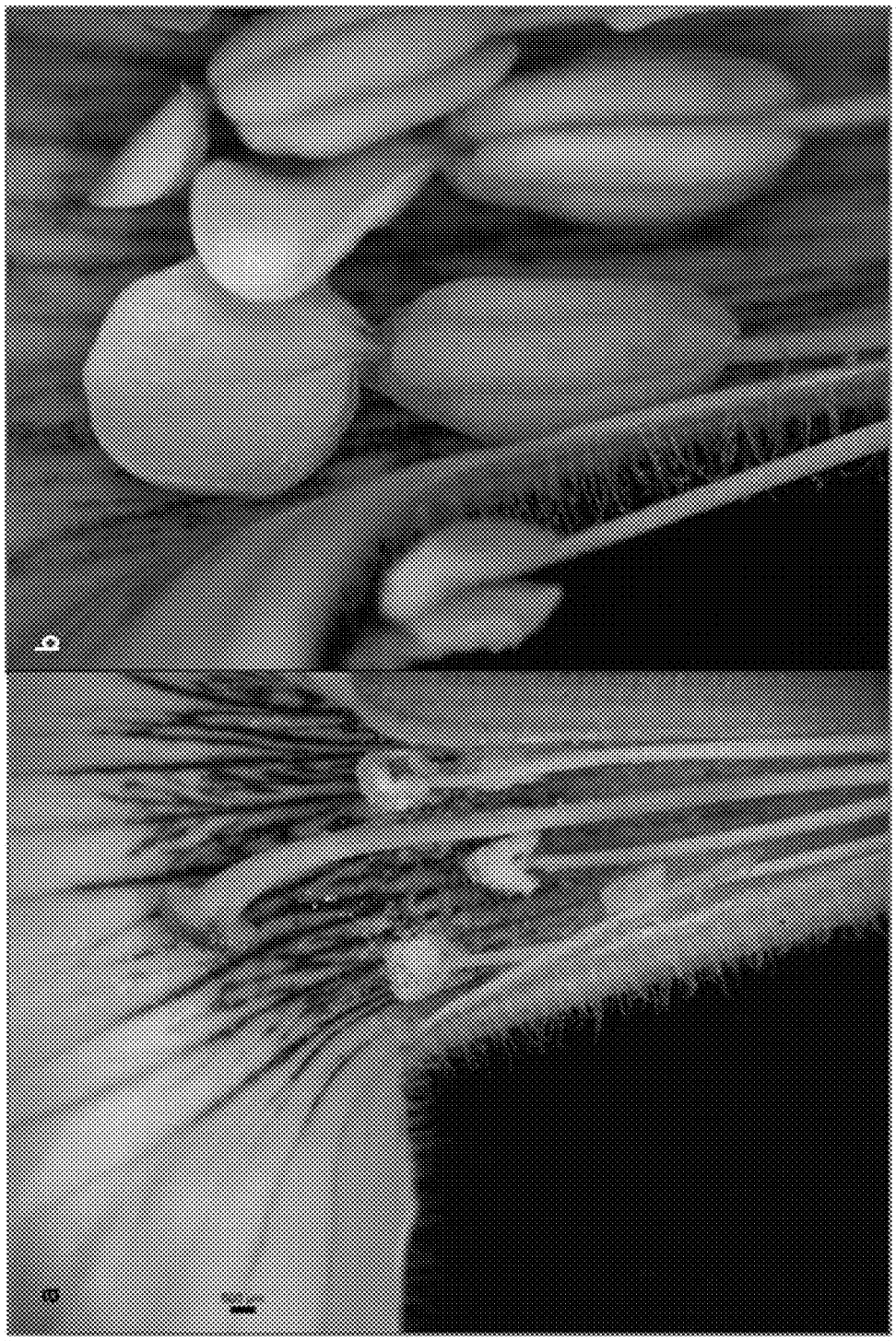
FIG. 11 shows over-expression of 'M9' ARF3 in petunia. a) untransformed and b) 35S:M9 ARF3 flower showing petaloid stamen that appear in two lines.

The applicants generated 10 independent lines expressing 35S: M9 ARF3, but the applicants were unable to recover 35S: wt ARF3 petunias. The applicants verified that the plants were expressing the construct by q-RT-PCR. Three independent lines of the 35S:M9 ARF3 had a floral phenotype, ranging from irregular petal margins, incomplete tube fusion, vascular defects, and petaloid stamens (FIGS. 10, 11). Microscopic analysis of the irregular petal margins revealed small patches of inverted petal polarity, which is consistent with the known function of ARF3 in adaxial-abaxial patterning.

Figure 12:
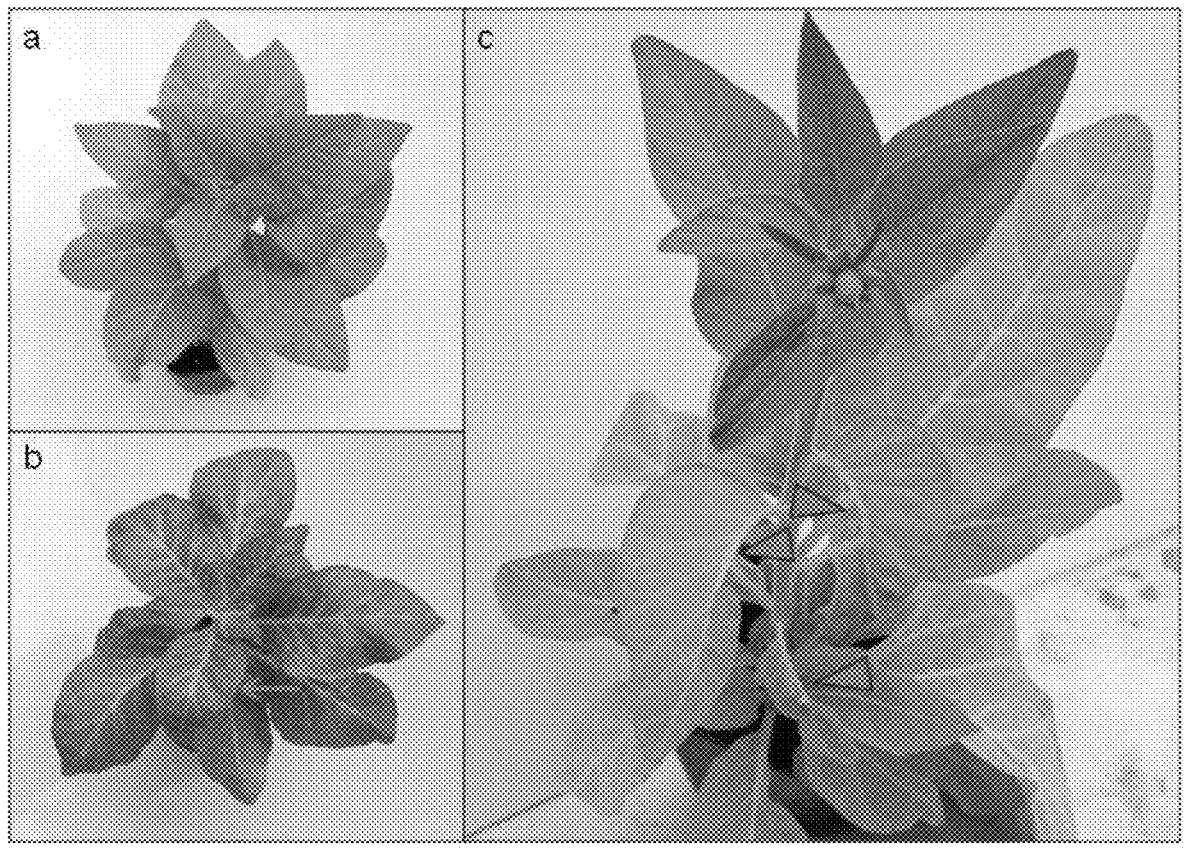
FIG. 12 shows over-expression of 'M9' ARF3 in tobacco. (a) un-transformed and (b-c) 35S: M9 ARF3. Vascular patterning defects were observed in several lines (arrows in b and c). One line showed an asymmetric leaf phenotype (arrowheads in c).
Figure 13:
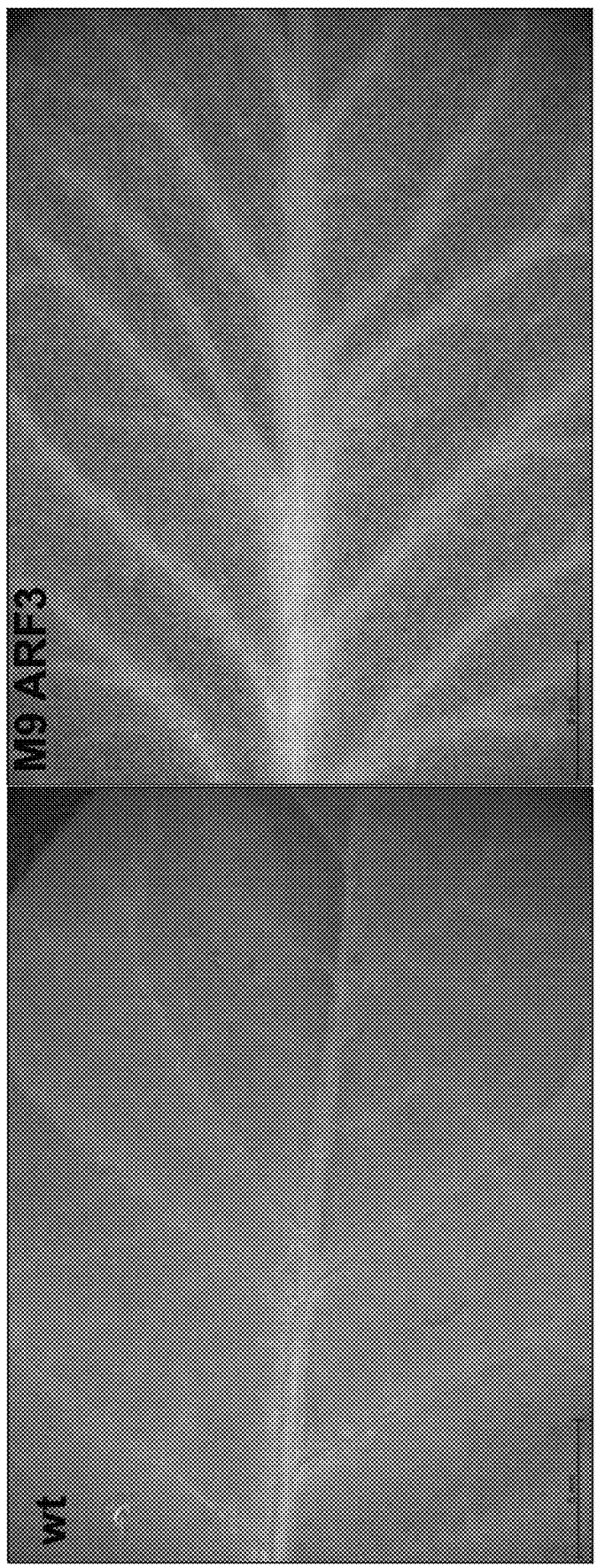
FIG. 13 shows the vascular patterning defects in the 'M9' ARF3 overexpression tobacco plants.
Figure 14:
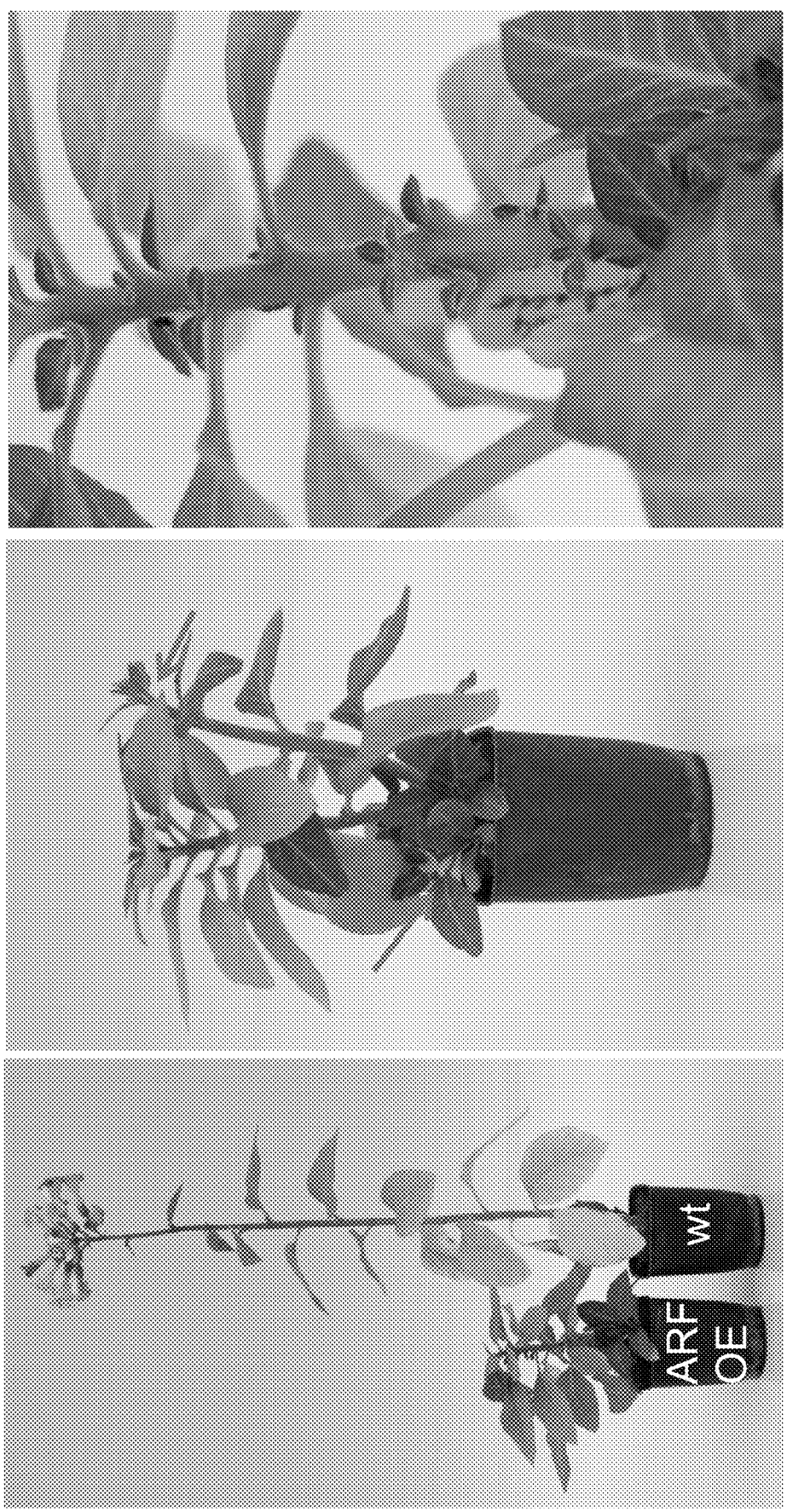
FIG. 14 shows 'M9' overexpression plants exhibiting reduced height, thick stems, shorter internodes and more axillary outgrowth compared to wild-type tobacco.
Figure 15:
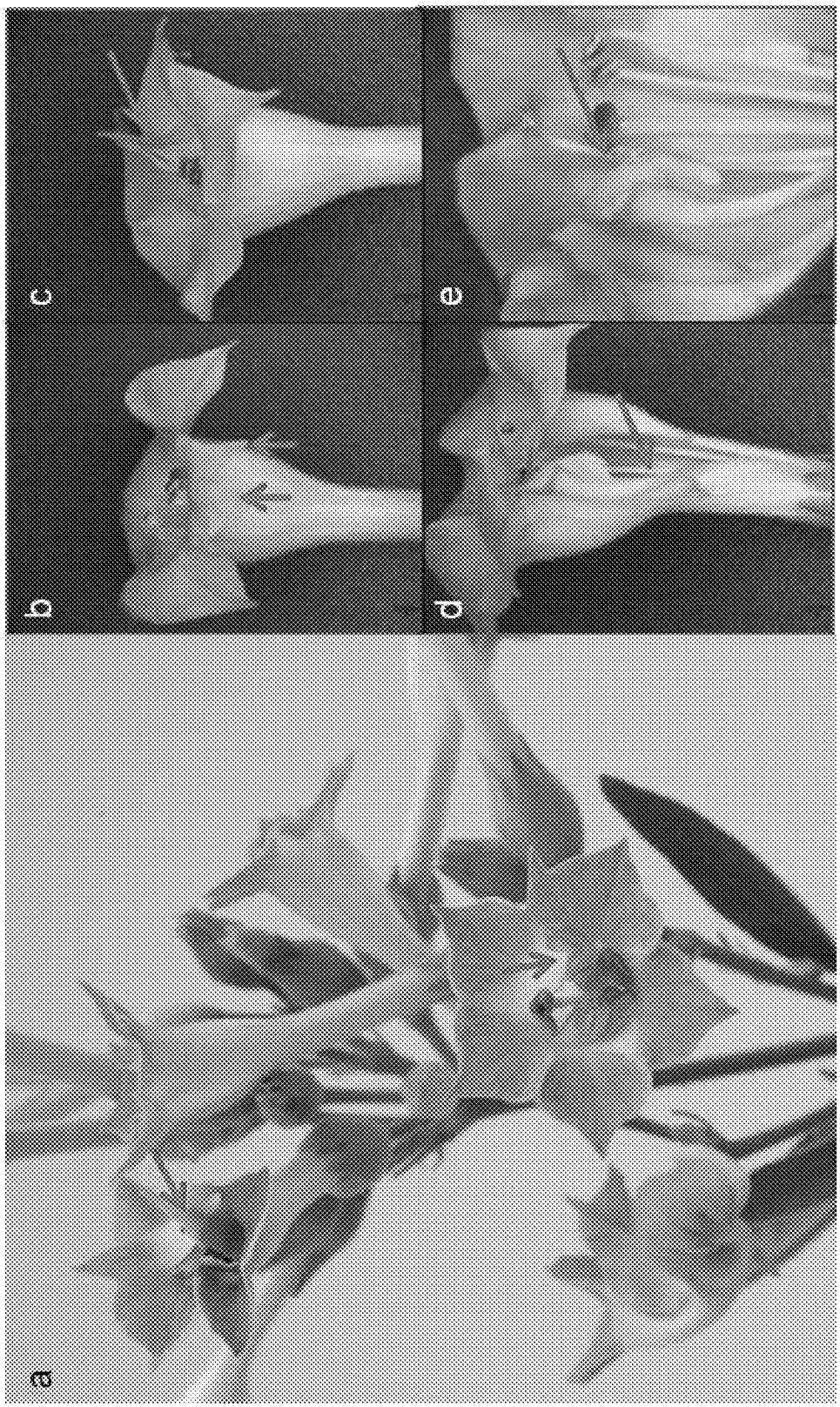
FIG. 15 shows floral phenotypes of 35S:ARF3 in tobacco. Extra petaloid organs are common (arrows in a, c, e) as well as patterning defects, irregular vascular patterning (arrows in a, b) and unfused tube (arrow in d).

The applicants generated 10 M9 ARF3 and 10 wt ARF3 over-expression lines in tobacco. The applicants verified that all $T_0$ plants were expressing the construct. Preliminary analysis indicates that several of the plants exhibit irregular vascular patterning in the leaves (FIG. 13). Two plants have asymmetric leaves, with half of the blade missing entirely or double midveins (FIG. 12 *b, c*). The most extreme line of 35S: M9 ARF 3 (#6) is much shorter than wild-type with thick stems, and decreased apical dominance, creating a bushy phenotype (FIG. 14). The lines with the highest ARF3 expression flowered earlier than the others. Early flowering is also seen in dwarfed scions in apple. Many of the M9 and wt ARF3 plants have floral phenotypes. These include incomplete fusion of the tube, patterning defects, and extra petaloid organs (FIG. 15).

Figure 16:
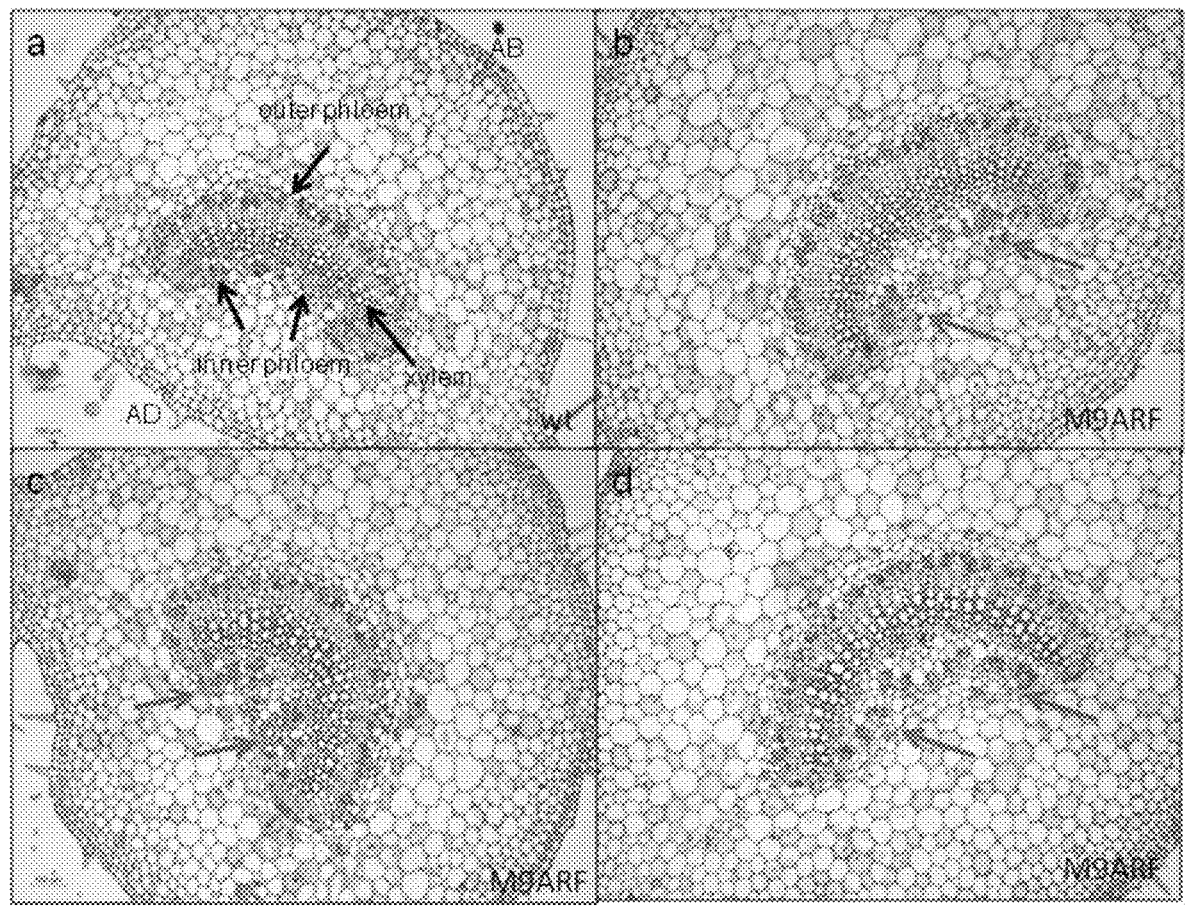
FIG. 16 shows irregular vascular development in 35S: ARF3 in tobacco. Sections of (a) untransformed and (b-d) 35S: M9 ARF3 tobacco petioles. Tobacco has a co-lateral arrangement of xylem surrounded by phloem on both abaxial (AB) and adaxial (AD) sides. The M9 ARF3 overexpression lines show irregular vascular patterning, with more inner phloem cells (red arrows in b-d).

To examine the vascular patterning defects in more detail, petioles from untransformed and ARF3 over-expression plants were fixed, sectioned and stained with safranin fast green. FIG. 16 shows representative micrographs illustrating that 35S:M9 ARF3 plants have irregular vascular patterning, with more inner phloem cells, consistent with the similar phenotype seen in M9 apple rootstock.

Phenotypic analysis of the ARF3 over-expression tobacco plants, can also be carried out on plants produced from $T_1$ seed.

Plants transformed to express ARF3 and M9 ARF3 can be phenotyped, as can scions grafted onto the transgenic, and control plants.

Such phenotyping can involve a detailed architectural analysis to document metamer initiation rate, the outgrowth and size of axillary brances, the size and node number of the primary shoot, and time to flowering.

Growth chambers can also be used to test if the transgenic plants have an altered sensitivity to long days or short days.

Further histological analysis can also be undertaken to compare vascular development between transgenic lines and untrasformed controls.

Example 5: Transgenic Expression of ARF3 in Apple

The constructs described in Example 4 above were transformed into apple, to further assess the phenotypic effect of higher expression and/or the non-synonymous SNP.

Plantlettes generated, can be tested to verify that ARF3 is over-expressed using qRT-PCR. Transgenic lines can be assessed for dwarfing-associated phenotypes by comparing the overall plant architecture (main axis height, outgrowth of axillary branches, etc) with un-transformed controls. To examine any changes to the vasculature, tissue can be fixed, sectioned, stained and photographed on a microscope to compare with untransformed controls.

Once plantlettes have generated roots and are large enough, they can be grafted with un-transformed controls. Scions can be assessed for dwarfing-associated phenotypes by comparing the number of growth units on the primary and secondary axis, comparing the number and size of sylleptic and prolleptic shoots, and eventually the number of flowers.

Example 6: Transgenic Expression of ARF3 in Pear

The constructs described in Example 4 above were transformed into pear, to further assess the phenotypic effect of higher expression and/or the non-synonymous SNP.

Plantlettes generated, can be tested to verify that ARF3 is over-expressed using qRT-PCR. Transgenic lines can be assessed for dwarfing-associated phenotypes by comparing the overall plant architecture (main axis height, outgrowth of axillary branches, etc) with un-transformed controls. To examine any changes to the vasculature, tissue can be fixed, sectioned, stained and photographed on a microscope to compare with untransformed controls.

Once plantlettes have generated roots and are large enough, they can be grafted with un-transformed controls. Scions can be assessed for dwarfing-associated phenotypes by comparing the number of growth units on the primary and secondary axis, comparing the number and size of sylleptic and prolleptic shoots, and eventually the number of flowers.

Example 7: Determine if the 'M9' SNP Alters Protein Function

Transient expression experiments in *Nicotiana benthamiana* (Martin, Kopperud et al. 2009), can be used to further assess the function of the non-synonymous SNP in the 'M9' ARF3. First an an auxin responsive reporter line, DR5:LUC (Ulmasov, Murfett et al. 1997) can be generated. This reporter will result in an enzyme that generates fluorescent compound in response to auxin.

The reporter construct can be co-expressed with either the 'M9' or wt ARF3 and the fluorescent compound measured after 1-3 days. These experiments can also be repeated with application of exogenous auxin to compare auxin sensitivity.

Example 8: Determine if Pear has Altered ARF3 Sequence and/or Expression

ARF3 expression in pear can be assessed by qRT-PCR to determine if "dwarfish" individuals from the pear rootstock population have higher expression of ARF3 than vigorous individuals. To determine if the same non-synonymous SNP exists "dwarfish" individuals, the pear ARF3 gene can be amplified and sequenced.

Example 9: Examination of the Phenotype of Apple Seedlings Genotyped for Dw1 and Dw2

Seedlings derived from controlled crosses can be genotyped for Dw1 and Dw2 to identify individuals that have zero, one or two copies of Dw1, and either zero or one copy of Dw2. ARF3 expression in apple seedlings and young trees can be assessed. Seedlings/trees can be measured for differences in metamer number of primary and secondary axes, the outgrowth of axillary shoots, and the time to flowering. Stem vascular development can also be assessed histologically.

Example 10: Tree Dry Weight Accumulation During the First Year of Growth

Figure 24:
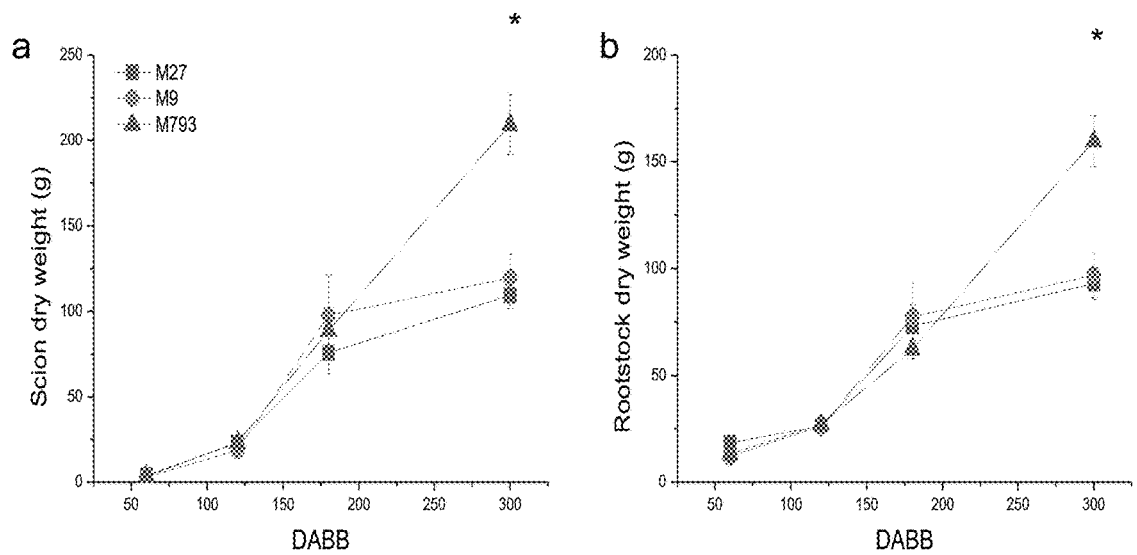
FIG. 24 shows tree dry weight accumulation during the first year of growth. 'Royal Gala' scions were grafted to 'M793' (vigorous), 'M9' (dwarfing) or 'M27' (very dwarfing). At each time point, six composite trees of each rootstock genotype were severed at the graft junction, a) scion and b) rootstock were dried and weighed. Values were compared by ANOVA and the only significant differences detected between vigorous and dwarfing rootstocks was at the final time point (*=p-value<0.001). Error bars are SE.

'Royal Gala' scions were grafted to 'M793' (vigorous), 'M9' (dwarfing) or 'M27' (very dwarfing). At each time point (60, 120, 180 and 300 days after bud break [DABB]), four to six composite trees of each rootstock genotype were severed at the graft junction. Scion and rootstock material was oven dried at 60° C. to a constant mass and weighed. Dry weights of scion include scion budwood, primary axis, sylleptic shoots and leaves, whilst dry weights of rootstock include roots and rootstock stem. Values were compared by ANOVA and the only significant differences detected between vigorous and dwarfing rootstocks was at the final time point (*=p-value<0.001). The results are shown in FIG. 24. Error bars are SE.

Example 11: Grafting Experiments

Methods of Grafting

Tobacco plants were grown in pots until plants had 10-15 leaves. In this experiment, all scions were wild-type tobacco, the "rootstocks" were wild-type, M9 ARF3 (2 independent lines, 2 and 6) and 35S: 793 (wt) ARF3 (line 4). We note M27 has the same ARF3 allele as M9, thus M27 contains the M9 allele of ARF3. In FIGS. 20 to 23, the M9 ARF3 rootstock lines are labelled M27 2-1 and M27 6-16 and the WT ARF3 rootstock line is labelled M793 4-3.

At the time of grafting, a horizontal cut was made through the "rootstock" stem at the very top of node 4-5. A "V"-shaped notch was cut vertically into the stem, 5-10 mm deep. The wild-type scion was cut from the base of the plant such that the base was approximately the diameter of the "rootstock". Leaves and shoot tip were removed and a piece of stem containing 2 nodes (each with an axillary meristem) was cut into a wedge shape at the bottom end. The scion was inserted into the "rootstock" notch and the junction was secured with a small piece of parafilm. Plants were placed in a mist tent to recover. After one week, all leaves from the "rootstock" were removed. Once it became apparent that one or more axillary meristems of the scion was growing out, the other was removed.

The scion shoots were grown until the first flower was fully extended, this date was considered the flowering date. The time between grafting date and the flowering date is the days to flowering. Once plants had flowered, architectural data was collected from the scion. The shoot length and node number was measured from the axil to the uppermost leaf base, this does not include the original scion stem segment, only the shoot that grew from the axillary meristem. The scion shoot diameter was measured at the base of the shoot using an electronic calliper. Trunk circumference area (TCA) was calculated with the formula: $(diameter/2)^2 \pi$ and is given in $mm^2$. The area of each leaf was measured with an electronic leaf scanner, total leaf area is the sum of all leaves on a plant and is given in $cm^2$. The scions were dried and weighed to determine dry weight (gm). Each line was compared to WT/WT by one way-ANOVA to determine significant differences.

Results

As ungrafted plants, 35S: M9 ARF3 line 6, hereafter referred to as line 6, show the most extreme phenotype. 35S: M9 ARF3 line 2 (line 2) has the mildest phenotype and 35S:793 ARF3 line 4 is undistinguishable from wild-type.

Figure 20:
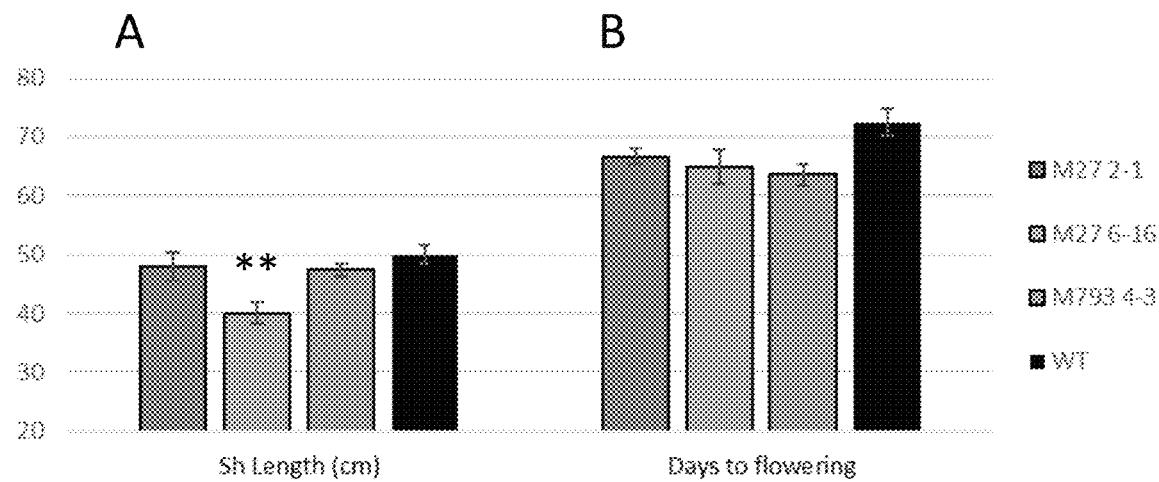
FIG. 20 shows the phenotypic characteristics of scions grafted onto 4 different "rootstocks" as indicated. Panel A (left side) shows shoot length of the grafted scion. Panel B (right side) shows days to flowering of the grafted scion. Values were compared to WT/WT by ANOVA, **=p-value<0.01, *=p-value<0.05.

Relative to the WT/WT homografts, the WT scions on line 6 rootstocks were significantly shorter (FIG. 20). Scions on line 2 and line 4 had slightly shorter lengths, but these were not significant.

Figure 21:
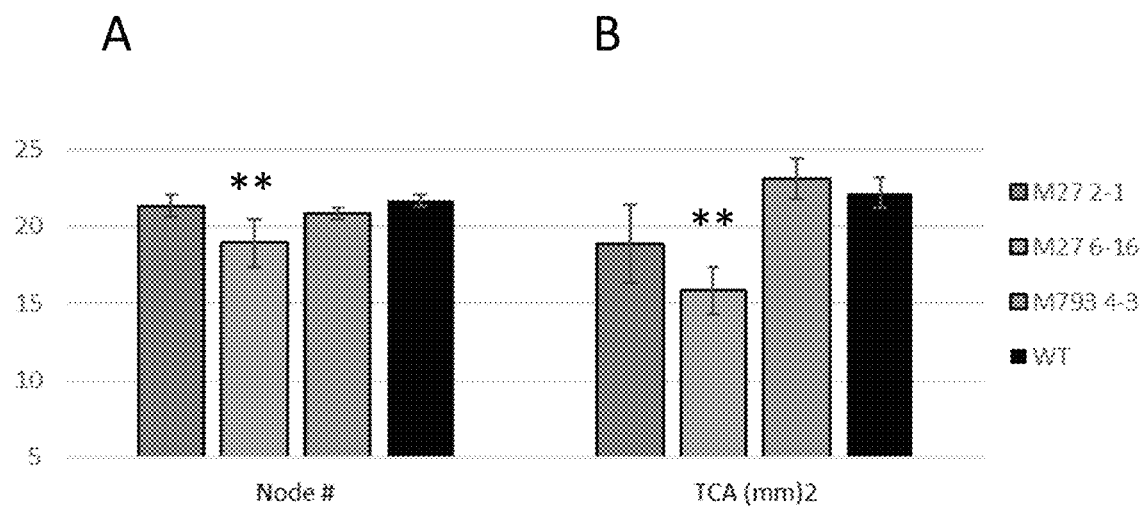
FIG. 21 shows the phenotypic characteristics of scions grafted onto 4 different "rootstocks" as indicated. Panel A (left side) shows number of nodes on the grafted scion. Panel B (right side) shows Trunk Cross-sectional Area (TCA) of the grafted scion. Values were compared to WT/WT by ANOVA, **=p-value<0.01, *=p-value<0.05.

Scions on all three transgenic rootstocks flowered slightly earlier than the WT/WT (FIG. 21).

Line 6 had significantly fewer nodes than WT/WT (FIG. 20).

Scions on both line 2 and line 6 had a smaller TCA than WT/WT. Line 6 was significantly different than WT/WT (FIG. 21).

Figure 22:
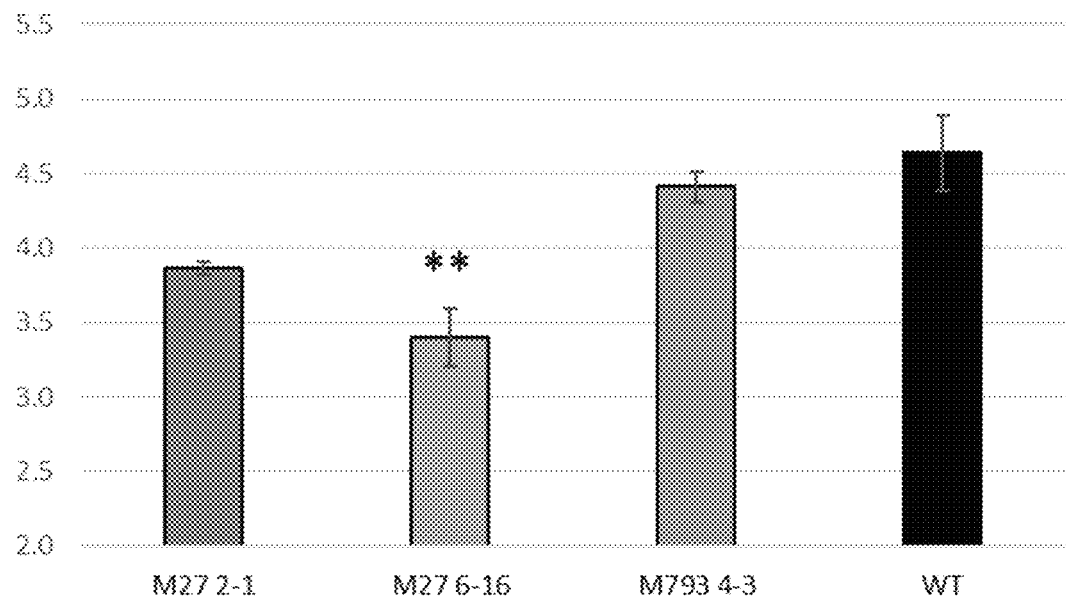
FIG. 22 shows the total scion dry weight of scions grafted onto 4 different "rootstocks" (same root stocks as in FIGS. 21 and 22). Values were compared to WT/WT by ANOVA, **=p-value<0.01, *=p-value<0.05.

Scions on line 2 and line 6 had a smaller dry weight than WT/WT. Line 6 was significantly different than WT/WT (FIG. 22).

Figure 23:
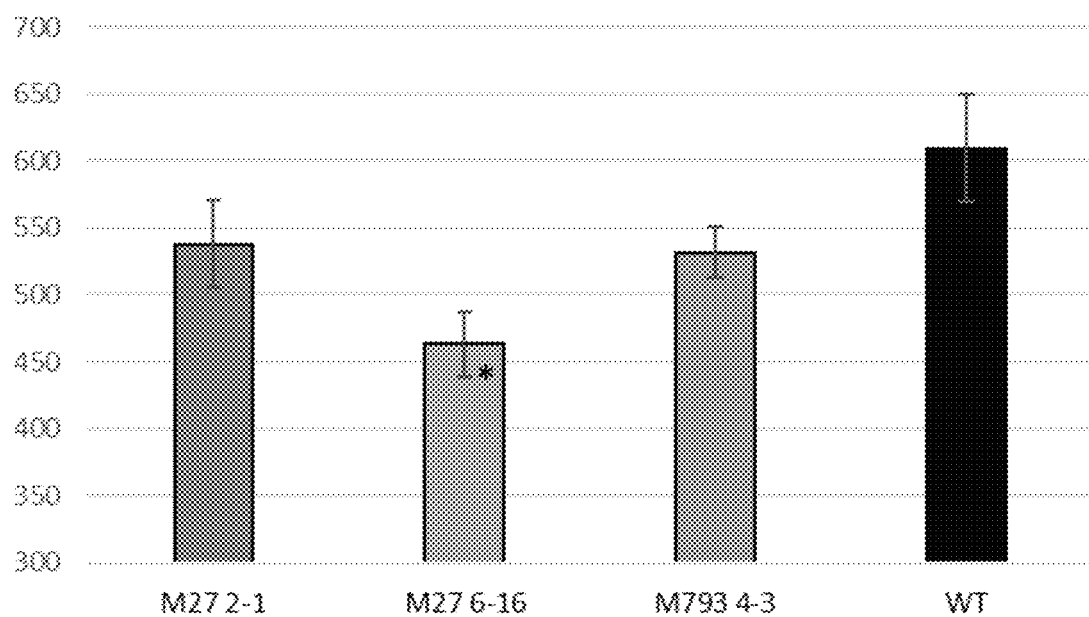
FIG. 23 shows the total leaf area of scions grafted onto 4 different "rootstocks" (same root stocks as in FIGS. 21 and 22). Values were compared to WT/WT by ANOVA, *=p-value<0.05.

Although lines 2, 6 and 4 had less total leaf area, only line 6 was significantly different from WT/WT (FIG. 23).

To our knowledge, there has been no report of dwarfing rootstocks causing smaller leaf size in scions.

Seedling Root Measurements

Figure 25:
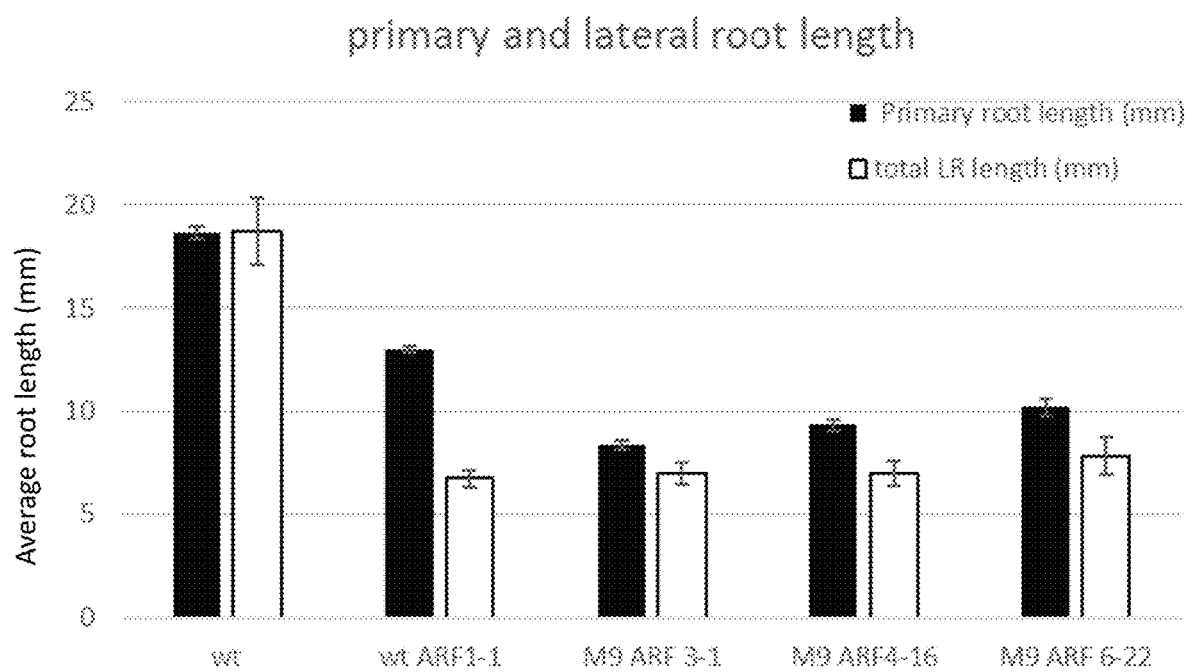
FIG. 25 shows average primary and total lateral root length of two week old seedlings. Seedlings were germinated on media, grown for two weeks, then harvested for photography. Digital images were measured using Image J. Error bars are standard error.

35S: M9 ARF3, 35S: wt ARF3 and wild-type tobacco seeds were sterilized in 2% bleach for 30 minutes, rinsed in distilled H2O, 3×, for 10 minutes each, then plated on MS media containing Kanamycin (for the transgenic seeds) or just MS (wild-type). Two weeks after plating, seedlings were removed from the media, excess media was removed and seedlings were photographed on a grid using a stereo microscope equipped with a digital camera. Primary and lateral root length were measured from digital images using Image J, total lateral root length is the sum of all lateral root lengths. (see FIG. 25).

In terms of shoot length, node number, TCA, scion dry weight, and scion mass, the effect of line 6 on the scion appears to replicate the effect of the 'M9' dwarfing rootstock.

Summary of Data Shown in Transgenic Plants, and Grafted Scions.

The phenotypes shown in transgenic plants over-expressing M9 ARF1 or WT ARF1, and in WT plants grafted onto transgenic plants over-expressing M9 ARF1 or WT ARF1, in comparison to the known phenotypes in known root stock and dwarfed grafted scions are summarised in the tables below.

TABLE 2

Phenotypes shown in transgenic plants over-expressing M9 ARF1 or WT ARF1

| Known dwarfing-associated phenotypes found in dwarfing rootstock plants (previous data) | Shown in plants over-expressing M9 ARF1 (this study) | Shown in plants over-expressing WT ARF1 (this study) |
| --- | --- | --- |
| bushier | Yes | No |
| altered xylem/phloem ratio | Yes | No |
| more phloem elements | Yes | No |
| reduced apical dominance | Yes | No |
| reduced root mass | Yes | Yes |

TABLE 3

Phenotypes shown in WT plants grafted onto transgenic plants over-expressing M9 ARF1 or WT ARF1

| Known dwarfing-associated phenotypes found in scions grafted onto dwarfing rootstock plants (previous data) | Shown in WT "scions" grafted on to "rootstock" plants over-expressing M9 ARF1 (this study) | Shown in WT "scions" grafted on to "rootstock" plants over-expressing M9 ARF1 (this study) |
|---|---|---|
| reduced vigour | Yes | Yes |
| less vegetative growth | Yes | Yes |
| earlier termination of shoot growth | Yes | Yes |
| smaller canopy | Yes | No |
| reduced stem circumference | Yes | No |
| reduced scion mass | Yes | No |

Materials and Methods

Plant Material

A rootstock population derived from crosses between *Malus x domestica* 'Malling9' ('M9') and *Malus robusta* 5 ('R5') was used for QTL analysis. For the first population, 135 seedlings were planted in 1998 and grown as stoolbeds to produce multiple rooted stocks of each genotype. The rootstocks were cleft grafted with 'Braeburn' scions, grown in the nursery for two years, then transplanted into the Plant & Food Research orchard (Havelock North, New Zealand) as described by Pilcher et al. (Pilcher, Celton et al. 2008) Replicates of the original 135 rootstocks were propagated in 2000 and planted in the orchard as one-year-old grafted trees. Of the replicated trees, 112 individuals from replicate two, and 57 individuals from replicate three were phenotyped for QTL analysis. The second population consisted of 350 seedlings, which were grafted as described above and planted in the orchard as one-year-old trees in 2004. From the second population, 81 individuals were evaluated for the QTL analysis and 314 survived until final phenotypic assessment in year seven. Trees were grown with in-row spacing of 1.5 m between trees and a double wire trellis as support, in a complete randomized block design. Scions grafted onto 'M9' and 'R5' were planted throughout as controls. Trees were not pruned, to allow full expression of the rootstock effects on scion growth. Once trees began fruiting, chemical thinning sprays were applied to avoid over-cropping and limb breakage.

Forty-one (41) apple rootstock accessions (*Malus* spp.) representing rootstock varieties used in major apple-growing regions in the world were used for pedigree analysis of Dw1 and Dw2.

Phenotypic Analysis

Rootstock effects on the development of 'Braeburn' scions were assessed using multiple methods, over seven years, within the two populations. Table 1 presents the specific traits that were assessed for the QTL analysis in each population/replicate and the sample size phenotyped. Height, internode number, and average internode length of the scion were recorded at the end of the first year of growth after grafting (year one). Flowering was scored by estimating the total number of flower clusters on each tree in the spring of year two, and placing them into quartiles relative to the most highly floral trees, i.e., 1-25% had the fewest flowers, 75-100% had the most flowers. Trees without any flowers in year two were recorded as "0". Trunk Cross-sectional Area (TCA) was measured 20 cm above the graft junction at the end of each year from year two to year seven. From year two to year seven, the overall vigour of each tree was assessed annually by comparing trunk size, crown height and spread, branch density and vigour. For the QTL analysis, an overall dwarfing phenotype (DW %) was assigned in year seven, with 100%=very vigorous, 80%=vigorous, 60%=intermediate, 40%=semi-dwarfed, and 20%=dwarfed.

The 41 rootstocks accessions used for the pedigree analysis were classified according to their dwarfing effect in accordance with the literature and in-house Plant & Food Research professional expertise.

DNA Isolation and Genotyping of 'M9'×'R5' Rootstock Population and Rootstock Accessions Total genomic DNA was extracted from leaves and quantified according to Gardiner et al. (Gardiner, Bassett et al. 1996) Leaf material was collected from 135 seedlings from the first 'M9'×'R5' population and 350 from the second population. Leaves of the rootstock accessions were collected from the Plant & Food Research germplasm collection in Havelock North, NZ, or from the USDA-ARS collection in Geneva, N.Y., USA.

For Dw1 and Dw2 genotyping of the entire population of 'M9'×'R5' rootstocks, polymerase chain reaction (PCR) products containing single nucleotide polymorphisms (SNP) were amplified on a LightCycler480 instrument (Roche Diagnostics) and screened using the High Resolution Melting (HRM) technique as described by Chagné et al. (Chagné, Gasic et al. 2008) Supplementary Table 1 lists the position of markers on the 'Golden Delicious' genome (Velasco, Zharkikh et al. 2010) and primer sequence.

Markers detecting SSRs located on LG5 and LG11 were employed to genotype the 41 rootstock accessions. Hi01c04, Hi04a08, CH03a09 and CH02d08 were developed by Silfverberg-Dilworth et al. (Silfverberg-Dilworth, Matasci et al. 2006) and Liebhard et al. (Liebhard, Gianfranceschi et al. 2002). Two new SSR markers (MDP0000365711 and MDP00024370) located at the top of LG11 were developed using the Plant & Food Research *Malus* genome database (Newcomb, Crowhurst et al. 2006), with the programmes Sputnik and Primer3. The M13 sequence TGTAAAACGACGGCCAGT (SEQ ID NO. 34) was added to the 5' end of the forward primer to enable the use of Schuelke's (Schueike 2000) approach to fluorescent labelling. PCR reactions were performed and analysed on an ABI 3500 Genetic Analyzer (Applied Biosystems) as described by Hayden et al. (Hayden, Nguyen et al. 2008).

QTL Analysis

The parental genetic maps for 'M9' and 'R5' were constructed using a total of 316 loci amplified from 296 primer pairs as described in Celton et al. (Celton, Tustin et al. 2009) The maps span a total of 1,175.7 and 1,086.7 cM for 'M9' and 'R5' respectively. (Celton, Tustin et al. 2009) The linkage phase of the markers was determined using Join-Map® 3.0 (Kyazma, NL). QTL analysis was performed for all growth traits using MapQTL® 5 Software (Kyazma, NL). Traits evaluated over multiple years and replicates were analysed separately. Interval mapping (IM), followed by multiple QTL model (MQM) analysis using the best markers obtained by IM as co-factors, was used for normally quantitative traits. Only additive models were considered for the QTL analysis. The threshold for QTL genome-wide significance was calculated after 1,000 permutations. Kruskal-Wallis analysis was used for ordinal traits such as the estimated number of flower clusters and expert assessment of dwarfing.

RNA Purification

For RNA-seq, tissue was collected from the rootstock stem of two M.793 and two M.9 individuals in November (60 DABB, ~90 days after grafting). M.27 was not included in the RNA-seq experiment because suitable material was not available. For qRT-PCR expression analysis, 30 'Royal Gala' trees grafted onto M.9, M.27 and M.793 rootstocks were grown as previously described. Tissue was collected for RNA purification in November, January, March and July (60, 120, 180 and 300 DABB respectively). For each time point, four to six trees of each genotype were selected for uniform scion growth to minimize any effects due to differential tree size. RNA was pooled from four shoots from each of the rootstock accessions shown in FIG. 5. For all other experiments, RNA from each individual was extracted and analysed separately. For all collections, the outer bark was removed, vascular tissue was scraped off with a scalpel, and snap frozen in liquid nitrogen. Tissue was harvested between four and five hours after sunrise for all time points. Total RNA was isolated and cDNA generated as described in (Janssen et al. 2008). The quality and concentration of the RNA samples was assessed with an RNA Nano kit (Agilent) and only samples with a RIN value of 8 or higher were further analyzed by sequencing or qRT-PCR.

RNA Sequencing and Data Processing

RNA was sent to Axeq/Macrogen for library preparation and sequencing using an Illumina Hiseq 2000 instrument. Individual samples were run as a multiplexed sample on one lane to produce 100 nucleotide paired end sequence reads. The first 13 bases of all RNAseq reads were trimmed using an in-house perl script. Adapters were removed using fastq-mcf from the ea-utils package (Aronesty 2011) using a minimum read retention length of 50 and a minimum quality score threshold of 20. Quality score analysis was performed using fastqc (http://www. bioinformatics. babraham.ac.uk/projects/fastqc/) both before and after trimming. Trimmed reads were mapped to the reference using bowtie2 (Langmead and Salzberg 2012) using the following settings: -a-end_to_end-sensitive. SAM file to BAM file conversion was undertaken using samtools (Li et al. 2009). Raw read counts and reads per kilobase per million (RPKM) values were extracted from BAM files using the multicov option of bedtools (Quinlan and Hall 2010) and either an in-house R script or cufflinks (Trapnell et al. 2010). Apple homologues of *Arabidopsis* flowering genes were determined by BLASP value and tested by reciprocal BLASTP. Differentially expressed genes were selected using the Limma package (Smyth 2005) in BioConductor, genes were selected using an adjusted P value of <0.05 and fold change cutoff>6 (Smyth 2005).

Transformation of ARF3 into Plants

Primers were designed to amplify the MdARF3 gene, from from 100 bp upstream of the start codon to 50 bp 5' of the stop codon. Single products were amplified from cDNA derived from 'Royal Gala' or 'M9' meristem enriched tissue. These products were cloned into an expression vector (pHEX), which uses the cauliflower mosaic virus (CaMV) 35S promoter to drive expression and contains the neomycin phoshotransferase II gene (NPTII) to confer kanamycin resistance. *Agrobacterium tumefaciens* strain GV3-101 transformed with either the 'Royal Gala' ("wt") or the 'M9' ARF3 was used to transform leaf discs from *N. tabacum* (Samsun), *petunia* ('Mitchell') or apple transformation cell lines. Callus formation and regeneration of plantlettes are as described in (Kotoda and Wada 2005).

Histology

Stem and petiole sections were fixed overnight in FAA (3.7% Formaldehyde, 50% EtOH, 5% Acetic Acid), processed and embedded in paraffin as described in Ruzin (Ruzin 1999). Tissue was sectioned to 100m on a rotary microtome, and slides were stained using a safranin/fast green procedure to distinguish xylem from phloem.

Grafting

Scions can be grafted onto rootstocks using cleft grafting or chip-budding depending on the material (Stoltz and Strang 1982; Webster and Wertheim 2003; Crasweller 2005).

REFERENCES

Bennett, T., T. Sieberer, et al. (2006). "The *Arabidopsis* MAX Pathway Controls Shoot Branching by Regulating Auxin Transport." *Current Biology* 16(6): 553-563.

Böhlenius, H., T. Huang, et al. (2006). "CO/FT Regulatory Module Controls Timing of Flowering and Seasonal Growth Cessation in Trees." *Science* 312(5776): 1040-1043.

Carriére, E. A. (1897). "Un nouveau sujet pour greffer les pommes." *Revue Horticole:* 436-437.

Celton, J. M., D. S. Tustin, et al. (2009). "Construction of a dense genetic linkage map for apple rootstocks using SSRs developed from *Malus* ESTs and *Pyrus* genomic sequences." *Tree Genetics & Genomes* 5(1): 93-107.

Chagné, D., K. Gasic, et al. (2008). "Development of a set of SNP markers present in expressed genes of the apple." *Genomics* 92(5): 353-358.

Costes, E. and Y. Guedon (1997). "Modelling the sylleptic branching of one-year-old trunks of apple cultivars." *Journal of American Society for Horticultural Science* 122: 53-62.

Costes, E. and Y. Guedon (2002). "Modelling branching patterns on 1-year-old trunks of six apple cultivars." *Annals of Botany* 89(5): 513-524.

Fahlgren, N., T. A. Montgomery, et al. (2006). "Regulation of AUXIN RESPONSE FACTOR3 by TAS3 ta-siRNA Affects Developmental Timing and Patterning in *Arabidopsis.*" *Current Biology* 16(9): 939-944.

Fazio, G., Y. Wan, et al. (2014). "Dw2, a New Dwarfing Locus in Apple Rootstocks and Its Relationship to Induction of Early Bearing in Apple Scions." *Journal of the American Society for Horticultural Science* 139(2): 87-98.

Ferree, D. C. and R. F. Carlson (1987). Apple rootstocks. *Rootstocks for Fruit Crops*. R. C. Rom and R. F. Carlson. New York, USA, John Wiley and Sons: 107-143.

Fulford, R. M. (1966). "The Morphogenesis of Apple Buds: II. The Development of the Bud." *Annals of Botany* 30(1): 25-38.

Gardiner, S., H. Bassett, et al. (1996). "A detailed linkage map around an apple scab resistance gene demonstrates that two disease resistance classes both carry the V f gene." *Theoretical and Applied Genetics* 93(4): 485-493.

Gregory, P. J. and T. S. George (2011). "Feeding nine billion: the challenge to sustainable crop production." *Journal of Experimental Botany* 62(15): 5233-5239.

Hatton, R. G. (1917). "'Paradise' apple socks." *Journal of the Royal Horticultural Society* 42: 361-399.

Hayden, M., T. Nguyen, et al. (2008). "Multiplex-Ready PCR: A new method for multiplexed SSR and SNP genotyping." *BMC Genomics* 9(1): 80.

Hirst, P. M. and D. C. Ferree (1995). "Rootstock Effects on the Flowering of 'Delicious' Apple. I. Bud Development." *Journal of the American Society for Horticultural Science* 120(6): 1010-1017.

Hooijdonk, B. v., D. Woolley, et al. (2011). "Rootstocks Modify Scion Architecture, Endogenous Hormones, and Root Growth of Newly Grafted 'Royal Gala' Apple Trees." *Journal of the American Society for Horticultural Science* 136(2): 93-102.

Hsu, C.-Y., Y. Liu, et al. (2006). "Poplar FT2 Shortens the Juvenile Phase and Promotes Seasonal Flowering." *The Plant Cell* 18(8): 1846-1861.

Hsu, C. Y., J. P. Adams, et al. (2011). "FLOWERING LOCUS T duplication coordinates reproductive and vegetative growth in perennial poplar." *Proceedings of the National Academy of Sciences of the United States of America* 108(26): 10756-10761.

Huijser, P. and M. Schmid (2011). "The control of developmental phase transitions in plants." *Development* 138(19): 4117-4129.

Hunter, C., M. R. Willmann, et al. (2006). "Trans-acting siRNA-mediated repression of ETTIN and ARF4 regulates heteroblasty in *Arabidopsis.*" *Development* 133(15): 2973-2981.

Imamura, T., T. Nakatsuka, et al. (2011). "The Gentian Orthologs of the FT/TFL1 Gene Family Control Floral Initiation in *Gentiana.*" *Plant and Cell Physiology* 52(6): 1031-1041.

Izhakia, A. and J. L. Bowman (2007). "KANADI and Class III HD-Zip Gene Families Regulate Embryo Patterning and Modulate Auxin Flow during Embryogenesis in *Arabidopsis.*" *The Plant Cell* 19: 495-508.

Kelley, D. R., A. Arreola, et al. (2012). "ETTIN (ARF3) physically interacts with KANADI proteins to form a functional complex essential for integument development and polarity determination in *Arabidopsis.*" *Development* 139(6): 1105-1109.

Kotoda, N. and M. Wada (2005). "MdTFL1, a TFL1-like gene of apple, retards the transition from the vegetative to reproductive phase in transgenic *Arabidopsis.*" *Plant Science* 168(1): 95-104.

Liebhard, R., L. Gianfranceschi, et al. (2002). "Development and characterisation of 140 new microsatellites in apple (*Malus x domestica* Borkh.)." *Molecular Breeding* 10(4): 217-241.

Ljung, K., A. K. Hull, et al. (2005). "Sites and Regulation of Auxin Biosynthesis in *Arabidopsis* Roots." *The Plant Cell Online* 17(4): 1090-1104.

Manhart, W. (1995). *Apples for the Twenty-First Century*. Portland, Oreg., North American Tree.

Martin, K., K. Kopperud, et al. (2009). "Transient expression in *Nicotiana benthamiana* fluorescent marker lines provides enhanced definition of protein localization, movement and interactions in planta." *Plant J* 59(1): 150-162.

Napoli, C. A., C. A. Beveridge, et al. (1999). "Reevaluating concepts of apical dominance and the control of axillary bud outgrowth." *Curr Top Dev Biol* 44: 127-169.

Newcomb, R. D., R. N. Crowhurst, et al. (2006). "Analyses of Expressed Sequence Tags from Apple." *Plant Physiology* 141(1): 147-166.

Pekker, I., J. P. Alvarez, et al. (2005). "Auxin Response Factors Mediate *Arabidopsis* Organ Asymmetry via Modulation of KANADI Activity." *The Plant Cell Online* 17(11): 2899-2910.

Pilcher, R. L. R., J.-M. Celton, et al. (2008). "Genetic Markers Linked to the Dwarfing Trait of Apple Rootstock 'Mailing 9'." *Journal of the American Society for Horticultural Science* 133(1): 100-106.

Ruzin, S. E. (1999). *Plant Microtechnique and Microscopy*. New York, N.Y., USA, Oxford University Press.

Schuelke, M. (2000). "An economic method for the fluorescent labeling of PCR fragments." *Nat Biotech* 18(2): 233-234.

Seleznyova, A. N., T. G. Thorp, et al. (2003). "Application of architectural analysis and AMAPmod methodology to study dwarfing phenomenon: the branch structure of 'Royal Gala" apple grafted on dwarfing and non-dwarfing rootstock/interstock combinations." *Annals of Botany* 91: 665-672.

Seleznyova, A. N., D. S. Tustin, et al. (2008). "Apple dwarfing rootstocks and interstocks affect the type of growth units produced during the annual growth cycle: Precocious transition to flowering affects the composition and vigour of annual shoots." *Annals of Botany* 101(5): 679-687.

Sessions, A., J. L. Nemhauser, et al. (1997). "ETTIN patterns the *Arabidopsis* floral meristem and reproductive organs." *Development* 124(22): 4481-4491.

Sessions, R. A. and P. C. Zambryski (1995). "*Arabidopsis* gynoecium structure in the wild and in ettin mutants." *Development* 121(5): 1519-1532.

Shimizu-Sato, S. and H. Mori (2001). "Control of Outgrowth and Dormancy in Axillary Buds." *Plant Physiology* 127(4): 1405-1413.

Silfverberg-Dilworth, E., C. L. Matasci, et al. (2006). "Microsatellite markers spanning the apple (*Malus x domestica* Borkh.) genome." *Tree Genetics & Genomes* 2(4): 202-224.

Soumelidou K, M. D., Battey N H, Barnett J R, John P (1994). "Auxin transport capacity in relation to the dwarfing effect of apple rootstocks." *Journal of Horticultural Science* 69: 719-725.

Steeves, T. A. and I. M. Sussex (1989). *Patterns in Plant Development*. New York, N.Y., Cambridge University Press.

Sussex, I. M. and N. M. Kerk (2001). "The evolution of plant architecture." *Current Opinion in Plant Biology* 4(1): 33-37.

Ulmasov, T., J. Murfett, et al. (1997). "Aux/IAA proteins repress expression of reporter genes containing natural and highly active synthetic auxin response elements." *The Plant Cell Online* 9(11): 1963-1971.

van Hooijdonk, B., D. Woolley, et al. (2011). "Rootstocks Modify Scion Architecture, Endogenous Hormones, and Root Growth of Newly Grafted 'Royal Gala' Apple Trees." *Journal of the American Society for Horticultural Science* 136(2): 93-102.

van Hooijdonk, B. M., D. J. Woolley, et al. (2010). "Initial alteration of scion architecture by dwarfing apple rootstocks may involve shoot-root-shoot signalling by auxin, gibberellin, and cytokinin." *Journal of Horticultural Science & Biotechnology* 85(1): 59-65.

van Hooijdonk, B. M., Woolley, D. J., Warrington, I. J. and Tustin, D. S. (2010). "Initial alteration of scion architecture by dwarfing apple rootstocks may involve shoot-root-shoot signalling by auxin, gibberellin, and cytokinin." *The Journal of Horticultural Science & Biotechnology* 85(1): 59-65.

Velasco, R., A. Zharkikh, et al. (2010). "The genome of the domesticated apple (*Malus x domestica* Borkh.)." *Nat Genet* 42: 833-839.

Webster, A. D. (1995). "Rootstock and interstock effects on deciduous fruit tree vigour, precocity and yield productivity." *New Zealand Journal of Crop and Horticultural Science* 23: 373-382.

Webster, A. D. and S. J. Wertheim (2003). Apple Rootstocks. *Apples: Botany, Production and Uses*. D. C. Ferree and I. J. Warrington. Wallingford, UK, CABI Publishing, CAB International.

Willmann, M. R. and R. S. Poethig (2011). "The effect of the floral repressor FLC on the timing and progression of vegetative phase change in *Arabidopsis*." *Development* 138(4): 677-685.

The invention claimed is:

1. A method for producing a plant with at least one dwarfing-associated phenotype the method comprising increasing the expression of an ARF3 polypeptide in the plant by transforming the plant with an ARF3 gene encoding the ARF3 polypeptide or genetically modifying an endogenous ARF3 gene to encode the ARF3 polypeptide in the plant, wherein the ARF3 polypeptide comprises a Leucine residue at a position corresponding to amino acid residue 72 in SEQ ID NO:1 or 28, and wherein the dwarfing-associated phenotype is selected from:

i) one of the following phenotypes in the plant:
  a) altered auxin transport,
  b) slower auxin transport,
  c) reduced apical dominance,
  d) an altered xylem/phloem ratio, e) an increased number of phloem elements,
f) smaller phloem elements,
g) thicker bark,
h) a bushier habit,
i) reduced root mass, and
ii) competence to induce one of the following phenotypes in a scion grafted on to the plant:
j) reduced vigour,
k) less vegetative growth,
l) earlier termination of shoot growth,
m) earlier competence to flower,
n) precocity,
o) earlier phase change,
p) smaller canopy,
q) reduced stem circumference,
r) reduced branch diameter,
s) fewer sylleptic branches,
t) shorter sylleptic branches,
u) more axillary flowers,
v) an earlier terminating primary axis,
w) earlier terminating secondary axes, and
x) shorter internode length
y) reduced scion mass, wherein the increased expression and the phenotypes a) to y) are relative to a control plant of the same type which has not been transformed or genetically modified to increase the expression of the ARF3 polypeptide.

2. The method of claim 1 wherein the ARF3 gene is operably linked to a heterologous promoter.

3. The method of claim 1 wherein the dwarfing-associated phenotype in the plant is at least one of reduced apical dominance, a bushier habit, an altered xylem/phloem ratio, an increased number of phloem elements and reduced root mass.

4. The method of claim 1 wherein the dwarfing-associated phenotype is the competence to induce at least one of: reduced vigour, less vegetative growth, earlier termination of shoot growth, a smaller canopy, reduced stem circumference, and reduced scion mass, in a scion grafted on to the plant.

5. The method of claim 1 wherein the method includes the step of grafting a scion on to a plant produced by the method.

6. A method for producing a plant with at least one dwarfing-associated phenotype selected from:
j) reduced vigour,
k) less vegetative growth
l) earlier termination of shoot growth
m) earlier competence to flower
n) precocity
o) earlier phase change
p) smaller canopy,
q) reduced stem circumference
r) reduced branch diameter
s) fewer sylleptic branches
t) shorter sylleptic branches
u) more axillary flowers
v) an earlier terminating primary axis,
w) earlier terminating secondary axes,
x) shorter internode length
y) reduced scion mass the method comprising the steps:
A. providing a plant produced by the method of claim 1,
B. grafting a scion onto the plant in A wherein at least one of j) to y) is exhibited in the scion grafted on to the plant in A, and wherein the phenotypes j) to y) are relative to a control plant of the same type which has not been transformed or genetically modified to increase the expression of the ARF3 polypeptide according to the method of claim 1.

7. The method of claim 6 wherein the phenotype exhibited in the scion is at least one of: reduced vigour, less vegetative growth, earlier termination of shoot growth, a smaller canopy, reduced stem circumference, and reduced scion mass.

8. The method of claim 1 in which the ARF3 polypeptide has a sequence with at least 70% identity to any one of SEQ ID NO:1 to 11, 28 and 29.

9. The method of claim 8 in which the ARF3 polypeptide has a sequence with at least 70% identity to SEQ ID NO:1 or 28 (MdARF3).

10. The method of claim 8 in which the ARF3 polypeptide comprises the sequence of SEQ ID NO:2 or 29 (M9 MdARF3).

* * * * *